United States Patent [19]

Klintz et al.

[11] Patent Number: 5,817,603
[45] Date of Patent: Oct. 6, 1998

[54] SUBSTITUTED CYCLOHEXENE-1,2-DICARBOXYLIC ACID DERIVATIVES AND INTERMEDIATES FOR THEIR PREPARATION

[75] Inventors: Ralf Klintz, Bochum; Elisabeth Heistracher, Ludwigshafen; Peter Schaefer, Bad Durkheim; Gerhard Hamprecht, Weinheim; Peter Plath, Frankenthal; Uwe Kardorff, Mannheim; Matthias Gerber, Limburgerhof; Karl-Otto Westphalen, Speyer; Helmut Walter, Obrigheim, all of Germany

[73] Assignee: BASF Aktiengesellschaft, Ludwigshafen, Germany

[21] Appl. No.: 798,539

[22] Filed: Feb. 11, 1997

Related U.S. Application Data

[63] Continuation of Ser. No. 325,220, filed as PCT/EP93/00953, Apr. 20, 1993, abandoned.

[30] Foreign Application Priority Data

Apr. 25, 1992 [DE] Germany .......................... 42 13 715.2
Nov. 11, 1992 [DE] Germany .......................... 42 38 001.4

[51] Int. Cl.$^6$ .......................... A01N 37/34; C07C 255/46
[52] U.S. Cl. .......................... 504/312; 504/310; 504/315; 504/335; 504/336; 504/337; 558/386; 558/426; 558/431; 558/414; 558/440; 558/441; 558/442; 560/39; 560/41; 564/153; 564/155
[58] Field of Search .......................... 564/155, 156, 564/158; 558/310, 386, 426, 414, 431, 440, 441, 442; 504/335, 310, 312, 315, 336, 337; 560/39, 41

[56] References Cited

U.S. PATENT DOCUMENTS

| | | | |
|---|---|---|---|
| 4,148,625 | 4/1979 | Nagase | 71/88 |
| 4,362,546 | 12/1982 | Nagase | 71/88 |
| 4,613,675 | 9/1986 | Lee | 71/86 |
| 5,045,105 | 9/1991 | Grossmann et al. | 71/74 |
| 5,062,884 | 11/1991 | Plath et al. | 71/95 |
| 5,089,042 | 2/1992 | Rueb et al. | 71/74 |
| 5,237,089 | 8/1993 | Plath et al. | 560/15 |

FOREIGN PATENT DOCUMENTS

| | | |
|---|---|---|
| 97 056 | 12/1983 | European Pat. Off. . |
| 240 659 | 10/1987 | European Pat. Off. . |
| 320 677 | 6/1989 | European Pat. Off. . |
| 385 231 | 9/1990 | European Pat. Off. . |
| 77 22652 | 2/1978 | France . |
| 77 22652 | 5/1979 | Germany . |
| 29 21 002 | 11/1979 | Germany . |
| 30 19 758 | 1/1981 | Germany . |
| 2 023 137 | 12/1978 | United Kingdom . |
| WO 87/07602 | 12/1987 | WIPO . |

OTHER PUBLICATIONS

JP 58/216 181—Dec. 15, 1983—Patent Abstracts of Japan.
JP 58/210 056—Dec. 7, 1983—Patent Abstracts of Japan.
Derwent Abstrs. JP 8 188–848, Nov. 4, 1983.
Derwent Abstrs. JP 61/043 160 Mar. 1, 1986.
Derwent Abstrs. JP 48/096 722 Dec. 10, 1973.
Derwent Abstrs. JP 55/157 547, Dec. 8, 1980.
Derwent Abstrs. JP 55/157 552, Dec. 8, 1980.
Derwent Abstrs. JP 55/162 756 Dec. 18, 1980.
Derwent Abstrs. JP 55/154 949, Dec. 2, 1980.
Derwent Abstrs. JP 55/157 545, Dec. 8, 1980.
Derwent Abstrs. JP 59/051 250, Mar. 24, 1984.
Derwent Abstrs. JP 60/252 457. Dec. 13, 1985.

*Primary Examiner*—Shailendra Kumar
*Attorney, Agent, or Firm*—Keil & Weinkauf

[57] ABSTRACT

Substituted cyclohexene-1,2-dicarboxylic acid derivatives I

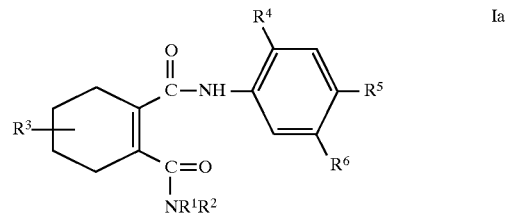

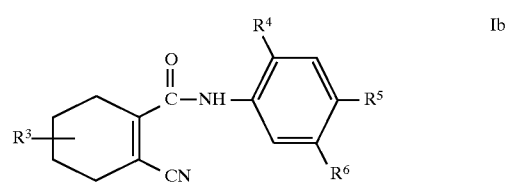

where $R^1$, $R^2$, $R^3$, $R^4$, $R^5$ and $R^6$ are herein defined, or the agriculturally useful salts of Ia and Ib and intermediates for their preparation, which compounds are useful as herbicides and for the desiccation/defoliation of plants.

6 Claims, No Drawings

SUBSTITUTED CYCLOHEXENE-1,2-DICARBOXYLIC ACID DERIVATIVES AND INTERMEDIATES FOR THEIR PREPARATION

This application is a continuation of application Ser. No. 08/325,220, filed as PCT/EP93/00953, Apr. 20, 1993, now abandoned.

Substituted cyclohexene-1,2-dicarboxylic acid derivatives of the general formulae Ia and Ib

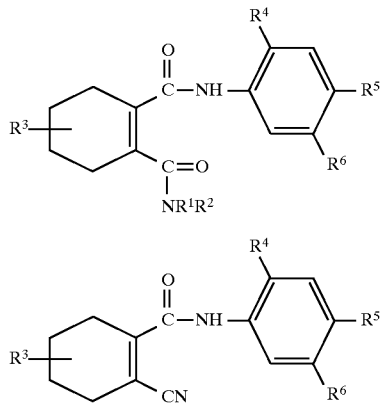

in which the variables have the following meaning:

$R^1$, $R^2$ hydrogen, a $C_1$–$C_6$-alkyl, $C_3$–$C_6$-alkenyl or $C_3$–$C_6$-alkynyl group, each of which three groups may furthermore carry from one to three radicals selected from a group consisting of halogen, cyano, amino, thio, hydroxyl, $C_1$–$C_6$-alkoxy, $C_1$–$C_6$-alkylsulfinyl, $C_1$–$C_6$-alkylsulfonyl, $C_1$–$C_6$-alkylcarbonyl, carboxyl, $C_1$–$C_6$-alkoxycarbonyl, $C_1$–$C_6$-alkylamino, $C_1$–$C_6$-dialkylamino, $C_1$–$C_6$-alkylaminocarbonyl, $C_1$–$C_6$-dialkylamino-carbonyl, $C_1$–$C_6$-alkylphosphono, $C_1$–$C_6$-dialkylphosphono, phenyl, 3-membered to 8-membered heterocyclyl which may be saturated or partially or completely unsaturated, it being possible for the heterocycles to carry from one to four hetero atoms selected from a group consisting of from one to four nitrogen atoms, one oxygen atom and one sulfur atom, and it being possible for the phenyl and heterocyclic radicals in turn to carry one of the following substituents on each substitutable atom: hydroxyl, halogen, cyano, nitro, trifluoromethyl, $C_1$–$C_6$-alkyl or $C_1$–$C_6$-alkoxy, a $C_3$–$C_8$-cycloalkyl group, the phenyl group or a saturated or partially or completely unsaturated 3-membered to 8-membered hetero-cyclyl group, each of which may carry from one to four hetero atoms selected from a group consisting of from one to four nitrogen atoms, one or two oxygen atoms and one or two sulfur atoms, it being possible for the phenyl and heterocyclic groups in turn to carry one of the following radicals on each substitutable carbon atom: hydroxyl, halogen, cyano, nitro, trifluoromethyl, halogen or $C_1$–$C_6$-alkyl, and, if $R^1$ is hydrogen or a $C_1$–$C_6$-alkyl group, $R^2$ may additionally be hydroxyl, a $C_1$–$C_6$-alkoxy, $C_3$–$C_6$-alkenyloxy or $C_3$–$C_6$-alkynyloxy group, a $C_3$–$C_7$-cycloalkoxy or $C_5$–$C_7$-cycloalkenyloxy group, a $C_1$–$C_6$-haloalkoxy or $C_3$–$C_6$-haloalkenyloxy group, a $C_3$–$C_7$-cycloalkyl-$C_3$–$C_6$-alkoxy group, a $C_1$–$C_6$-alkylcarbonyloxy group, a $C_1$–$C_6$-cyanoalkoxy group, a hydroxy-$C_1$–$C_6$-alkoxy, $C_1$–$C_6$-alkoxy-$C_1$–$C_6$-alkoxy or C–$C_6$-alkoxycarbonyl-$C_1$–$C_6$-alkoxy group, a $C_1$–$C_6$-alkylthio-$C_1$–$C_6$-alkoxy group, a $C_1$–$C_6$-alkylamino-$C_1$–$C_6$-alkoxy or $C_1$–$C_6$-dialkylamino-$C_1$–$C_6$-alkoxy group, a phenyl-$C_1$–$C_6$-alkoxy, phenyl-$C_3$–$C_6$-alkenyloxy or phenyl-$C_3$–$C_6$-alkynyloxy group, where in each case one or two methylene groups of the alkoxy, alkenyloxy or alkynyloxy chains may be replaced by oxygen, sulfur and/or a $C_1$–$C_6$-alkylamino chain, and each phenyl ring may be unsubstituted or may carry from one to three radicals selected from a group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, a group —$NR^7R^8$, where $R^7$ and $R^8$, independently of one another are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkyl-carbonyl, $C_1$–$C_6$-alkoxycarbonyl, $C_1$–$C_6$-alkoxy-$C_1$–$C_6$-alkyl or phenyl which may be unsubstituted or may carry from one to three radicals selected from a group consisting of $C_1$–$C_6$-alkyl, halogen, cyano, nitro, $C_1$–$C_6$-alkoxy and $C_1$–$C_6$-alkoxycarbonyl, or $R^7$ and $R^8$ together with the common nitrogen atom may form a saturated or partially or completely unsaturated 4-membered to 7-membered ring which may also contain a further nitrogen atom or an oxygen or sulfur atom as a second ring member, or $R^1$ and $R^2$, together with the nitrogen atom to which they are bonded, may form a three-membered to eight-membered saturated or unsaturated, nonaromatic heterocyclic structure which may carry from one to three nitrogen atoms and/or one oxygen or sulfur atom and one or two carbonyl groups, it being possible for the heterocyclic structure to be unsubstituted or to carry from one to three $C_1$–$C_6$-alkyl radicals;

$R^3$ is hydrogen or a $C_1$–$C_6$-alkyl group;

$R^4$ is hydrogen or halogen;

$R^5$ is hydrogen, halogen, nitro, cyano or trifluoromethyl;

$R^6$ is a saturated or partially or completely unsaturated 3-membered to 8-membered heterocyclic group which may carry from one to four hetero atoms selected from a group consisting of from one to four nitrogen atoms, one or two oxygen atoms and one or two sulfur atoms, it being possible for one or two methylene groups of the heterocyclic group to be replaced by carbonyl and for the heterocyclic structure to carry one of the following radicals on each substitutable carbon atom:

$C_1$–$C_6$-alkyl, $C_2$–$C_6$-alkenyl, $C_2$–$C_6$-alkynyl, $C_1$–$C_6$-alkoxy, $C_1$–$C_6$-alkylthio, $C_3$–$C_6$-alkenyloxy, $C_3$–$C_6$-alkynyloxy, $C_3$–$C_6$-alkenylthio, $C_3$–$C_6$-alkynylthio, $C_1$–$C_6$-alkoxycarbonyl, nitro, amino, halogen, $C_1$–$C_4$-alkylamino, di-($C_1$–$C_4$-alkyl)-amino, cyano, $C_1$–$C_6$-cyanoalkyl, $C_1$–$C_6$-haloalkyl or $C_1$–$C_6$-haloalkoxy, one of the following groups:

—A—CN or —A—CO—B, —$OR^9$, —$C(R^{10})$=O, —$C(R^{10})$=S, —$C(R^{10})$=N—$R^{16}$, —$CHR^{10}$— $CHR^{11}$—CO—B, —$C(X^1R^{14})(X^2R^{15})R^{10}$ or —$P(R^{12})(R^{13})$=O, where A is a straight-chain $C_2$–$C_4$-alkenylene or $C_2$–$C_4$-alkynylene chain, both of which may be unsubstituted or may carry one or two radicals selected from a group consisting of halogen, cyano, $C_1$–$C_6$-alkyl, $C_1$–$C_6$-haloalkyl, hydroxyl, $C_1$–$C_6$-alkoxy, $C_1$–$C_6$-alkylcarbonyloxy, $C_1$–$C_6$-alkoxycarbonyl and $C_1$–$C_6$-alkylcarbonyl;

B is hydrogen, $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, —OR$^{17}$ or —SR$^{17}$, where R$^{17}$ is hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, phenyl which may be unsubstituted or may carry from one to three radicals selected from a group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, $C_1$–$C_6$-cyanoalkyl, $C_3$–$C_6$-haloalkenyl, $C_1$–$C_6$-alkoxy-carbonyl, $C_1$–$C_6$-alkoxy-$C_1$–$C_6$-alkyl, $C_1$–$C_6$-alkoxy-carbonyl-$C_1$–$C_6$-alkyl or $C_1$–$C_6$-alkoximino-$C_1$–$C_6$-alkyl;

phenyl which may be unsubstituted or may carry from one to three radicals selected from a group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, $C_1$–$C_6$-alkoxy-$C_1$–$C_6$-alkyl, di-($C_1$–$C_6$-alkoxy)-$C_1$–$C_6$-alkyl, $C_1$–$C_6$-alkylthio-$C_1$–$C_6$-alkyl, or —NR$^{18}$R$^{19}$, where R$^{18}$ and R$^{19}$, independently of one another, are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkyl-carbonyl, $C_1$–$C_6$-alkoxycarbonyl, $C_1$–$C_6$-alkoxy-$C_1$–$C_6$-alkyl or phenyl which may be unsubstituted or may carry from one to three radicals selected from a group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl, or R$^{18}$1 and R$^{19}$, together with the common nitrogen atom, form a saturated or partially or completely unsaturated 4-membered to 7-membered ring which may also contain a further nitrogen atom or an oxygen or sulfur atom as a second ring member;

R$^9$ is $C_1$–$C_6$-cyanoalkyl, $C_1$–$C_6$-alkoxy-$C_1$–$C_6$-alkyl, $C_1$–$C_6$-haloalkyl, $C_3$–$C_6$-haloalkenyl, $C_3$–$C_6$-alkynyl or $C_3$–$C_6$-haloalkynyl;

phenyl, phenyl-$C_1$–$C_6$-alkyl, 3-membered to 8-membered heterocyclyl or heterocyclyl-$C_1$–$C_6$-alkyl, where the heterocyclic structures may be saturated or partially or completely unsaturated and may carry from one to four hetero atoms selected from a group consisting of from one to four nitrogen atoms, one or two oxygen atoms and one or two sulfur atoms, it being possible for the phenyl and heterocyclic radicals in turn to carry one of the following substituents on each substitutable carbon atom: $C_1$–$C_6$-alkyl, $C_2$–$C_6$-alkenyl, halogen, cyano, nitro, $C_1$–$C_6$-haloalkyl, $C_1$–$C_6$-alkoxy or $C_1$–$C_6$-alkoxycarbonyl, $C_1$–$C_6$-alkoxycarbonyl-$C_2$–$C_6$-alkyl, $c_1$–$C_6$-alkoxy-$C_1$–$C_6$-alkoxycarbonyl-$C_1$–$C_6$-alkyl, $C_1$–$C_6$-alkoximino-$C_1$–$C_6$-alkyl;

R$^{10}$ is hydrogen or cyano,
$C_1$–$C_6$-alkyl, $C_3$–$C_6$-alkenyl, $C_3$–$C_6$-alkynyl,
$C_1$–$C_6$-haloalkyl,
$C_3$–$C_7$-cycloalkyl, $C_1$–$C_6$-alkoxycarbonyl or $C_1$–$C_6$-alkoxycarbonyl-$C_1$–$C_6$-alkyl, phenyl which may be unsubstituted or may carry from one to three radicals selected from a group consisting of halogen, nitro, cyano, $C_1$–$C_6$-alkyl, $C_3$–$C_6$-alkenyl, $C_1$–$C_6$-haloalkyl, $C_1$–$C_6$-alkoxy and $C_1$–$C_6$-alkoxycarbonyl;

R$^{11}$ is halogen, trifluoromethyl, hydroxyl, $C_1$–$C_6$-alkoxy or $C_1$–$C_6$-alkoxycarbonyloxy;

R$^{12}$ and R$^{13}$ are each $C_1$–$C_6$-alkoxy or phenyl which may be unsubstituted or may carry from one to three radicals selected from a group consisting of $C_1$–$C_6$-alkyl, $C_1$–$C_6$-haloalkyl, $C_3$–$C_6$-alkenyl, halogen, cyano, nitro, $C_1$–$C_6$-alkoxy and $C_1$–$C_6$-alkoxycarbonyl;

X$^1$ and X$^2$ are each oxygen or sulfur;

R$^{14}$ and R$^{15}$ are each $C_1$–$C_6$-alkyl, $C_3$–$C_6$-alkenyl, $C_3$–$C_6$-alkynyl or $C_1$–$C_6$-alkoxy-$C_1$–$C_6$-alkyl or R$^{14}$ and R$^{15}$ together form a two-membered to four-membered carbon chain which may be unsaturated and which, if desired, may contain a carbonyl group as a ring member, it being possible for the carbon chain to be unsubstituted or to carry from one to three radicals selected from the group consisting of $C_1$–$C_6$-alkyl, $C_2$–$C_6$-alkenyl, halogen, cyano, nitro, amino, $C_3$–$C_6$-alkoxy, $C_3$–$C_6$-alkenyloxy, $C_3$–$C_6$-alkynyloxy, carboxyl, $C_1$–$C_6$-alkoxycarbonyl, $C_1$–$C_6$-haloalkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-hydroxyalkyl, $C_1$–$C_6$-thioalkyl, $C_1$–$C_6$-alkylthio-$C_1$–$C_6$-alkyl and $C_1$–$C_6$-cyanoalkyl;

R$^{16}$ is hydrogen, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, phenyl which may be unsubstituted or may carry from one to three radicals selected from a group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, $C_1$–$C_6$-alkoxy-$C_1$–$C_6$-alkyl, hydroxyl, $C_1$–$C_6$-alkoxy, $C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, $C_3$–$C_7$-cycloalkyl-$C_1$–$C_6$-alkoxy, $C_1$–$C_6$-alkylcarbonyloxy, $C_1$–$C_6$-cyanoalkoxy, $C_1$–$C_6$-alkoxy-$C_{,1}$–$C_6$-alkoxy, $C_1$–$C_6$-alkoxycarbonyl-$C_1$–$C_6$-alkoxy, hydroxy-$C_1$–$C_6$-alkoxy, $C_1$–$C_6$-alkylthio-$C_1$–$C_6$-alkoxy, $C_1$–$C_6$-alkylamino-$C_1$–$C_6$-alkoxy, di-($C_1$–$C_6$-alkyl)-amino-$C_1$–$C_6$-alkoxy, phenyl-$C_1$–$C_6$-alkoxy, phenyl-$C_3$–$C_6$-alkenyloxy or phenyl-$C_3$–$C_6$-alkynyloxy, it being possible in each case for one or two methylene groups of the alkoxy, alkenyloxy and alkynyloxy chains to be replaced by oxygen, sulfur and/or a $C_1$–$C_6$-alkylamino chain, and for each phenyl ring to be unsubstituted or to carry from one to three substituents selected from a group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl,

—NR$^{18}$R$^{19}$;

or R$^5$ and R$^6$ together form a saturated or partially or completely unsaturated three-membered to five-membered carbon chain which, if desired, may contain one or two oxygen, sulfur or nitrogen atoms and/or one carbonyl or $C_1$–$C_6$-alkoximino group as a ring member, it being possible for the chain to be unsubstituted or in turn to carry one or two radicals selected from a group consisting of cyano, nitro, amino, halogen, $C_1$–$C_6$-alkyl, $C_1$–$C_6$-haloalkyl, $C_2$–$C_6$-alkenyl, $C_2$–$C_6$-alkynyl, $C_1$–$C_6$-cyanoalkyl, $C_1$–$C_6$-alkoxycarbonyl-$C_1$–$C_6$-alkyl, phenyl-$C_1$–$C_6$-alkyl and three-membered to eight-membered heterocyclyl-$C_3$–$C_6$-alkyl, where the heterocyclic structure may be saturated or partially or completely unsaturated and may carry from one to four hetero atoms selected from a group consisting of from one to four nitrogen atoms, one or two oxygen atoms and one or two sulfur atoms, with the proviso that, in the formula Ia, $R^9$ is not $C_1$–$C_6$-alkynyl and $R^{16}$ is not $C_1$–$C_6$-alkoxy and, in the formula Ib, $R^9$ is not $C_1$–$C_1$-haloalkyl, and the agriculturally useful salts of the compounds Ia and Ib.

The present invention furthermore relates to novel intermediates of the formulae IIa, IIIa and VIIIa.

The present invention also relates to herbicides and plant growth regulators which contain these compounds as active substances.

EP-A 097 056 discloses herbicidal cyclohexene-1,2-dicarboxylic acid derivatives Ia'

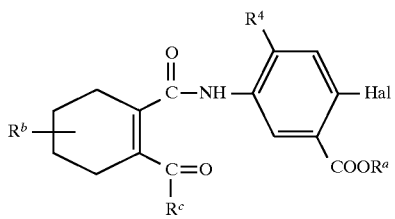

where $R^a$ is hydrogen or $C_1$–$C_1$-alkyl which is substituted by halogen or by $C_1$–$C_4$-alkoxy, Hal is halogen, $R^b$ is hydrogen or $C_1$–$C_4$-alkyl and $R^c$ is amino.

Furthermore, JO 60/252 457 describes cyclohexenedicarboxylic derivatives of the formula Ia''

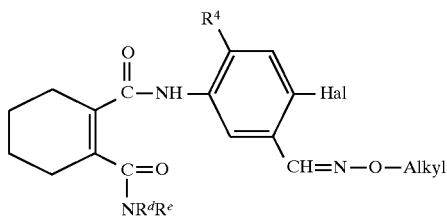

where $R^d$ and $R^e$ are each hydrogen, alkyl, alkenyl, alkynyl or cycloalkyl or, together with the nitrogen atom, form a heterocyclic ring, and their use as herbicides.

Furthermore, WO-A 87/107 602 describes, inter alia, compounds of the formula Ia'''

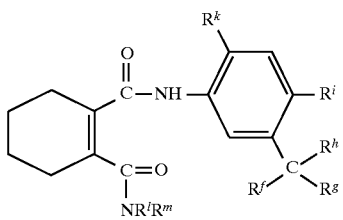

where $R^f$ and $R^g$ are each alkyl, alkenyl, alkynyl or halogen and $^h$ is, inter alia, cyano or a substituted alkylcarbonyl, carbonyl or alkoxycarbonylalkyl group.

Moreover, JO 59/051 250 discloses herbicidal N-phenyltetrahydrophthalamide derivatives of the formula Ia''''

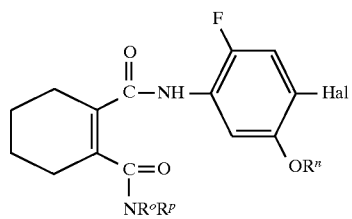

where $R^n$ is alkyl, alkenyl, alkynyl, carbamoylmethyl or alkoxycarbonylmethyl and $R^o$ and $R^p$ are each hydrogen, alkyl, alkenyl or phenyl or, together with the nitrogen atom, form a heterocyclic ring.

U.S. Pat. No. 4,613,675 discloses further compounds of the type of the formula Ia'''' which carry a radical $R^4$ instead of the fluorine atom and a radical —$CHR^qP(=)(OR^r)R^s$ instead of $R^n$, where $R^q$ is hydrogen or alkyl, $R^r$ is alkyl, alkoxyalkyl or alkoxycarbonyl and $R^s$ is hydrogen, alkyl, cycloalkyl or alkoxyalkyl.

JO 55/157 545, DE-A 30 19 758 and JO 55/154 949 likewise disclose compounds of the type of the formula Ia'''' which carry the radical $R^4$ instead of the fluorine atom and, inter alia, alkyl or alkenyl instead of $R^n$.

Further cyclohexene-1,2-dicarboxylic acid derivatives of the type of compounds Ia are described, for example, in the following publications:

DE-A 28 51 379, DE-A 29 21 002, JO 48/096 722, JO 55/157 547, JO 55/157 552, JO 55 162 756, JO 58/188 848, JO 58/210 056, JO 58/216 181 and JO 61/043 160.

JO 58/210 056 discloses cyclohexene-1,2-dicarboxylic acid derivatives of the general formula Ib'

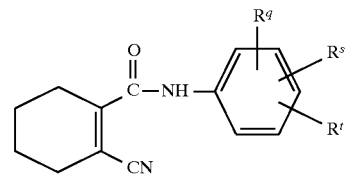

where $R^q$, $R^s$ and $R^t$ are each H, halogen, cyano, alkoxy, alkenyloxy, unsubstituted or substituted aralkoxy, unesterified or esterified carboxyl or haloalkyl.

However, the selectivity of these known herbi- cides with respect to the weeds is satisfactory only to a limited extent, so that it is an object of the present invention to provide novel herbicidal compounds, by means of which the weeds can be selectively controlled more effectively than to date (in conjunction with good compatibility for the crop plants).

We have found that this object is achieved by the substituted cyclohexene-1,2-carboxylic acid derivatives Ia and Ib defined at the outset.

We have also found herbicides which contain these substances and have a good herbicidal action.

We have furthermore found that the novel compounds Ia and Ib are suitable as defoliants and desiccants, for example in the crops cotton, potato, rape, sunflower, soybean or field beans.

The meanings stated above for the substituents $R^1$ to $R^{20}$ are general terms for individual lists of the individual group members. All alkyl, alkenyl, alkynyl, haloalkyl and haloalkoxy moieties may be straight-chain or branched, unless stated otherwise. The haloalkyl and haloalkoxy radicals may carry identical or different halogen atoms.

Examples of specific meanings are: halogen: fluorine, chlorine, bromine or iodine, preferably fluorine or chlorine; $C_1$–$C_6$-alkyl and $C_1$–$C_6$-alkyl moieties in the radicals di-($C_1$–$C_6$-alkoxy)-$C_1$–$C_6$-alkyl, $C_3$–$C_6$-alkenyloxy- $C_1$–$C_6$-alkyl, $C_3$–$C_6$-alkynyloxy-$C_1$–$C_6$-alkyl, $C_1$–$C_6$-alkoxy-$C_1$–$C_6$-alkoxy-carbonyl-$C_1$–$C_6$-alkyl and heterocyclyl-$C_1$–$C_6$-alkyl: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-methyl-propyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, isopropyl or tert-butyl;

$C_2$–$C_6$-alkenyl: ethenyl, and $C_3$–$C_6$-alkenyl, such as prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methyl-prop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-mehylpent-1-en-1-yl, 3-methyl-pent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methyl-pent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methyl-pent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1, 1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl, preferably ethenyl or prop-2-en-1-yl;

$C_2$–$C_6$-alkynyl: ethynyl and $C_3$–$C_6$-alkynyl, such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pentyn-5-yl, pent-2-yn-1-yl, pent-2-yn-4-yl, pent-2-yn-5-yl, 3-methylbut-1-yn-3-yl, 3-methyl-but-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, preferably prop-2-ynyl;

$C_1$–$C_1$–cycloalkyl: cyclopropyl, cyclobutyl, cylcopentyl, cyclohexyl, cycloheptyl or cyclooctyl, preferably $C_3$–$C_6$-cycloalkyl, such as cyclopropyl, cyclopentyl or cyclohexyl;

$C_1$–$C_6$-haloalkyl: chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 3-chloropropyl, preferably trifluoromethyl;

$C_1$–$C_6$-hydroxyalkyl: hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl or 2-hydroxymethylprop-2-yl, preferably hydroxymethyl;

$C_1$–$C_6$-thioalkyl: thiomethyl, 1-thioeth-1-yl, 2-thioeth-1-yl, 1-thioprop-1-yl, 2-thioprop-1-yl, 3-thioprop-1-yl, 1-thioprop-2-yl, 2-thioprop-2-yl, 1-thiobut-1-yl, 2-thiobut-1-yl, 3-thiobut-1-yl, 4-thiobut-1-yl, 1-thiobut-2-yl, 2-thiobut-2-yl, 1-thiobut-3-yl, 2-thiobut-3-yl, 1-thio-2-methylprop-3-yl, 2-thio-2-methylpropy-3-yl, 3-thio-2-methylprop-3-yl or 2-thiomethylprop-2-yl, preferably thiomethyl;

$C_1$–$C_6$-cyanoalkyl: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, preferably cyanomethyl or 1-cyanoeth-1-yl;

$C_1$–$C_1$–cyanoalkoxy: cyanomethoxy, 1-cyanoeth-1-oxy, 2-cyanoeth-1-oxy, 1-cyanoprop-1-oxy, 2-cyanoprop-1-oxy, 3-cyanoprop-1-oxy, 1-cyanoprop-2-oxy, 2-cyanoprop-2-oxy, 1-cyanobut-1-oxy, 2-cyanobut-1-oxy, 3-cyanobut-1-oxy, 4-cyanobut-1-oxy, 1-cyanobut-2-oxy, 2-cyanobut-2-oxy, 1-cyanobut-3-oxy, 2-cyanobut-3-oxy, 1-cyano-2-methylprop-3-oxy, 2-cyano-2-methylprop-3-oxy, 3-cyano-2-methylprop-3-oxy or 2-cyanomethylprop-2-oxy, preferably cyanomethoxy or 1-cyanoeth-1-oxy;

phenyl-$C_1$–$C_6$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)-eth-1-yl, 1-(phenylmethyl)-1-(methyl)-eth-1-yl or 1-(phenylmethyl)prop-1-yl, preferably benzyl;

$C_1$–$C_6$-alkoxy and the $C_1$–$C_6$-alkoxy moieties in the radicals $C_3$–$C_7$-cycloalkyl-$C_1$–$C_6$-alkoxy, di-($C_1$–$C_6$-alkoxy)-$C_1$–$C_6$-alkyl, $C_1$–$C_6$-alkoxycarbonyl-$C_1$–$C_6$-alkoxy and $C_1$–$C_6$-alkoxy-$C_1$–$C_6$-alkoxycarbonyl-$C_1$–$C_6$-alkyl:

methoxy, ethoxy, n-propoxy, 1-methylethoxy, n-butoxy, 1-methylpropoxy, 2-methylpropoxy, 1,1-dimethylethoxy, n-pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, preferably $C_1$–$C_4$-alkoxy, such as methoxy or ethoxy;

$C_1$–$C_6$-haloalkoxy: chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, preferably Cl-$C_2$-haloalkoxy, such as trifluoromethoxy;

$C_1$–$C_6$-alkylthio: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, n-hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, preferably $C_1$–$C_4$-alkylthio, such as methylthio or ethylthio;

phenyl-$C_1$–$C_6$-alkoxy: benzyloxy, 1-phenylethoxy, 2-phenyl-ethoxy, 1-phenylprop-1-yloxy, 2-phenylprop-1-yloxy, 3-phenylprop-1-yloxy, 1-phenylbut-1-yloxy, 2-phenylbut-1-yloxy, 3-phenylbut-1-yloxy, 4-phenylbut-1-yloxy, 1-phenylbut-2-yloxy, 2-phenylbut-2-yloxy, 3-phenylbut-2-yloxy, 3-phenylbut-2-yloxy, 4-phenylbut-2-yloxy, 1-(phenylmethyl)-eth-1-yloxy, 1-(phenoxymethyl)-1-(methyl)-eth-1-yloxy or 1-(phenylmethyl)-prop-1-yloxy, preferably benzyloxy;

$C_3$–$C_6$-alkenyloxy and the $C_3$–$C_6$-alkenyloxy moiety in $C_3$–$C_6$-alkenyloxy-$C_1$–$C_6$-alkyl: prop-2-en-1-yloxy, n-buten-4-yloxy, n-buten-3-yloxy, 1-methylprop-2-en-1-yloxy, 2-methylprop-2-en-1-yloxy, n-penten-3-yloxy, n-penten-4-yloxy, n-penten-5-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-2-en-1-yloxy, 1-ethylprop-2-en-1-yloxy, n-hex-2-en-1-yloxy, n-hex-3-en-1-yloxy, n-hex-4-en-1-yloxy, n-hex-5-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-2-en-1-yloxy, 1,2-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-2-en-1-yloxy, 2,3-dimethylbut-3-en-1-yloxy, 3,3-dimethylbut-2-en-1-yloxy, 1-ethylbut-2-en-1-yloxy, 1-ethylbut-3-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy or 1-ethyl-2-methylprop-2-en-1-yloxy, preferably prop-2-en-1-yloxy;

$C_3$–$C_6$-alkenylthio: prop-2-en-1-ylthio, n-buten-4-ylthio, n-buten-3-ylthio, 1-methylprop-2-en-1-ylthio, 2-methylprop-2-en-1-ylthio, n-penten-3-ylthio, n-penten-4-ylthio, n-penten-5-ylthio, 1-methylbut-2-en-1-ylthio, 2-methylbut-2-en-1-ylthio, 3-methylbut-2-en-1-ylthio, 1-methyl-but-3-en-1-ylthio, 2-methylbut-3-en-1-ylthio, 3-methylbut-3-en-1-ylthio, 1,1-dimethylprop-2-en-1-ylthio, 1,2-dimethylprop-2-en-1-ylthio, 1-ethylprop-2-en-1-ylthio, n-hex-2-en-1-ylthio, n-hex-3-en-1-ylthio, n-hex-4-en-1-ylthio, n-hex-5-en-1-ylthio, 1-methylpent-2-en-1-ylthio, 2-methylpent-2-en-1-ylthio, 3-methylpent-2-en-1-ylthio, 4-methylpent-2-en-1-ylthio, 1-methylpent-3-en-1-ylthio, 2-methylpent-3-en-1-ylthio, 3-methylpent-3-en-1-ylthio, 4-methylpent-3-en-1-ylthio, 1-methylpent-4-en-1-ylthio, 2-methylpent-4-en-1-ylthio, 3-methylpent-4-en-1-ylthio, 4-methylpent-4-en-1-ylthio, 1,1-dimethylbut-2-en-1-ylthio, 1,1-dimethylbut-3-en-1-ylthio, 1,2-dimethylbut-2-en-1-ylthio, 1,2-dimethylbut-3-en-1-ylthio, 1,3-dimethylbut-2-en-1-ylthio, 1,3-dimethylbut-3-en-1-ylthio, 2,2-dimethylbut-3-en-1-ylthio, 2,3-dimethylbut-2-en-1-ylthio, 2,3-dimethylbut-3-en-1-ylthio, 3,3-dimethylbut-2-en-1-ylthio, 1-ethylbut-2-en-1-ylthio, 1-ethylbut-3-en-1-ylthio, 2-ethylbut-2-en-1-ylthio, 2-ethylbut-3-en-1-ylthio, 1,1,2-trimethylprop-2-en-1-ylthio, 1-ethyl-1-methylprop-2-en-1-ylthio or 1-ethyl-2-methylprop-2-en-1-ylthio, preferably prop-2-en-1-ylthio;

$C_3$–$C_6$-alkynyloxy or the $C_3$–$C_6$-alkynyloxy moiety in $C_3$–$C_6$-alkynyloxy-$C_1$–$C_6$-alkyl: prop-2-yn-3-yloxy, n-but-1-yn-4-yloxy, n-but-2-yn-1-yloxy, n-pent-1-yn-3-yloxy, n-pent-1-yn-4-yloxy, n-pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-3-yloxy, 3-methylpent-1-yn-4-yloxy, 3-methylpent-1-yn-5-yloxy, 4-methylpent-2-yn-4-yloxy or 4-methylpent-2-yn-5-yloxy, preferably prop-2-yloxy;

$C_3$–$C_6$-alkynylthio: prop-2-yn-3-ylthio, n-but-1-yn-4-ylthio, n-but-2-yn-1-ylthio, n-pent-1-yn-3-ylthio, n-pent-1-yn-4-ylthio, n-pent-1-yn-5-ylthio, pent-2-yn-1-ylthio, pent-2-yn-4-ylthio, pent-2-yn-5-ylthio, 3-methylbut-1-yn-3-ylthio, 3-methylbut-1-yn-4-ylthio, n-hex-1-yn-3-ylthio, n-hex-1-yn-4-ylthio, n-hex-1-yn-5-ylthio, n-hex-1-yn-6-ylthio, n-hex-2-yn-1-ylthio, n-hex-2-yn-4-ylthio, n-hex-2-yn-5-ylthio, n-hex-2-yn-6-ylthio, n-hex-3-yn-1-ylthio, n-hex-3-yn-2-ylthio, 3-methylpent-1-yn-3-ylthio, 3-methylpent-1-yn-4-ylthio, 3-methylpent-1-yn-5-ylthio, 4-methylpent-2-yn-4-ylthio or 4-methylpent-2-yn-5-ylthio, preferably prop-2-ynylthio; $C_3$–$C_6$- haloalkenyloxy, 2-chloroprop-2-enyloxy, 3-chloroprop-2-enyloxy, 2,3-dichloroprop-2-enyloxy, 3,3-dichloroprop-2-enyloxy, 2,3,3-trichloroprop-2-enyloxy, 2,3-dichlorobut-2-enyloxy, 2-bromoprop-2-enyloxy, 3-bromoprop-2-enyloxy, 2,3-dibromoprop-2-enyloxy, 3,3-dibromoprop-2-enyloxy, 2,3,3-tribromoprop-2-enyloxy or 2,3-dibromobut-2-enyloxy;

phenyl-$C_3$–$C_6$-alkenyloxy: 2-phenylprop-2-enyloxy, 3-phenylprop-2-enyloxy or 4-phenylbut-2-en-1-yloxy;

phenyl-$C_3$–$C_6$-alkynyloxy: 2-phenylprop-2-ynyloxy, 3-phenylprop-2-yn-1-yloxy or 4-phenylbut-2-yn-1-yloxy;

$C_3$–$C_7$-cycloalkoxy: cyclopropoxy, cyclobutoxy, cyclopentyloxy, cyclohexyloxy or cycloheptyloxy;

$C_5$–$C_7$-cycloalkenyloxy, such as cyclopent-1-enyloxy, cylcopent-2-enyloxy, cyclopent-3-enyloxy, cyclohex-1-enyloxy, cyclohex-2-enyloxy, cyclohex-3-enyloxy, cyclohept-1-enyloxy, cyclohept-2-enyloxy, cyclohept-3 or cyclohept-4-enyloxy;

$C_1$–$C_4$-alkylamino: methylamino, ethylamino, n-propylamino, 1-methylethylamino, n-butylamino, 1-methylpropylamino, 2-methylpropylamino or 1,1-dimethylethylamino;

$C_1$–$C_6$-alkylamino: methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutyl-amino, 2,2-dimethylpropylamino, 1-ethylpropylamino, n-hexylamino, 1,1-dimethylpropylamino, 1,2-dimethylpropyl-amino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2'-trimethylpropylamino, 1,2, 2-trimethylpropylamino, 1-ethyl-1-methylpropylamino or 1-ethyl-2-methylpropylamino, preferably $C_1$–$C_4$-alkylamino, such as methylamino or ethylamino;

di-$C_1$–$C_6$-alkylamino: N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)-amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl) amino, N-(1,1-dimethylethyl)-N-(1-methylpropyl) amino amino or N-(1,1-dimethylethyl)-N-(2-methylpropyl)amino, preferably dimethylamino or diethylamino;

$C_1$–$C_6$-alkylphosphono: methylphosphono, ethylphosphono, n-propylphosphono, 1-methylethylphosphono, n-butylphosphono, 1-methylpropylphosphono, 2-methyl-propylphosphono, 1,1-dimethylethylphosphono, n-pentylphosphono, 1-methylbutylphosphono, 2-methylbutylphosphono, 3-methylbutylphosphono, 2,2-dimethylpropylphosphono, 1-ethyl-propylphosphono, n-hexylphosphono, 1,1-dimethylpropylphosphono, 1,2-dimethyl-propylphosphono, 1-methylpentylphosphono, 2-methylpentylphosphono, 3-methylphenyl-phosphono, 4-methylpentylphosphono, 1,1-dimethylbutylphosphono, 1,2-dimethyl-butylphosphono, 1,3-dimethylbutylphosphono, 2,2-dimethylbutylphosphono, 2,3-dimethyl-butylphosphono, 3,3-dimethylbutylphosphono, 1-ethylbutylphosphono, 2-ethylbutylphosphono, 1,1, 2-trimethylpropylphosphono, 1,2,2-trimethyl-propylphosphono, 1-ethyl-1-methylpropyl-phosphono or 1-ethyl-2-methylphosphono, preferably $C_3$–$C_4$-alkylphosphono, such as methylphosphono or ethylphosphono;

di-$C_1$–$C_1$-alkylphosphono: N,N-dimethylphosphono, N,N-diethylphosphono, N,N-dipropylphosphono, N,N-di-(1-methylethyl )phosphono, N,N-dibutylphosphono, N,N-di-(1-methylpropyl) phosphono, N,N-di-(2-methylpropyl)phosphono, N,N-di-(1,1-dimethylethyl)phosphono, N-ethyl-N-methylphosphono, N-methyl-N-propylphosphono, N-methyl-N-(1-methylethyl)phosphono, N-butyl-N-methylphosphono, N-methyl-N-(1-methylpropyl) phosphono, N-methyl-N-(2-methylpropyl) phosphono, N-(1,1-dimethylethyl)-N-methylphosphono, N-ethyl-N-propylphosphono, N-ethyl-N-(1-methylethyl)phosphono, N-butyl-N-ethylphosphono, N-ethyl-N-(1-methylpropyl) phosphono, N-ethyl-N-(2-methylpropyl)phosphono, N-ethyl-N-(1,1-dimethylethyl)phosphono, N-(1-methylethyl)-N-propylphosphono, N-butyl-N-propylphosphono, N-(1-methylpropyl)-N-propylphosphono, N-(2-methylpropyl)-N-propylphosphono, N-(1,1-dimethylethyl)-N-propylphosphono, N-butyl-N-(1-methylethyl)-phosphono, N-(1-methylethyl)-N-(1-methylpropyl) phosphono, N-(1-methylethyl)-N-(2-methylpropylphosphono, N-(1,1-dimethylethyl)-N-(1-methylethyl)phosphono, N-buty-N-(1-methylpropyl)phosphono, N-butyl-N-(2-methylpropyl)phosphono, N-butyl-N-(1,1-dimethylethyl)phosphono, N-(1-methylpropyl)-N-(2-methylpropyl)phosphono, N-(1,1-dimethylethyl)-N-(1-methylpropyl)phosphono or N-(1,1-dimethylethyl)-N-(2-methylpropyl)phosphono, preferably dimethylphosphono or diethylphosphono;

$C_1$–$C_6$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethyl-propylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, preferably $C_1$–$C_4$-alkylsulfonyl, such as methylsulfonyl or ethylsulfonyl;

$C_1$–$C_6$-alkoxy-$C_1$–$C_6$-alkyl: methoxymethyl, ethoxymethyl, n-propoxymethyl, (1-methylethoxy) methyl, n-butoxymethyl, (1-methylpropoxy)methyl, (2-methylpropoxy)methyl, (1,1-dimethylethoxy) methyl, n-pentyloxymethyl, (1-methylbutoxy) methyl, (2-methylbutoxy)methyl, (3-methylbutoxy) methyl, (2,2-dimethylpropoxy)methyl, (1-ethylpropoxy)methyl, n-hexyloxymethyl, (1,1-dimethylpropoxy)methyl, (1,2-dimethylpropoxy) methyl, (1-methylpentyloxy)methyl, (2-methylpentyloxy)methyl, (3-methylpentyloxy) methyl, (4-methylpentyloxy)methyl, (1,1-dimethylbutoxy)methyl, (1,2-dimethylbutoxy) methyl, (1,3-dimethylbutoxy)methyl, (2,2-dimethylbutoxy)methyl, (2,3-dimethylbutoxy) methyl, (3,3-dimethylbutoxy)methyl, (1-ethylbutoxy)methyl, (2-ethylbutoxy)methyl, (1,1,2-trimethylpropoxy)methyl, (1,2,2-trimethylpropoxy)methyl, (1-ethyl-1-methylpropoxy)methyl, (1-ethyl-2-methylpropoxy) methyl, methoxyethyl, ethoxyethyl, n-propoxyethyl, (1-methylethoxy)ethyl, n-butoxyethyl, (1-methylpropoxy)ethyl, (2-methylpropoxy)ethyl, (1,1-dimethylethoxy) ethyl, n-pentyloxyethyl, (1-methylbutoxy)ethyl, (2-methylbutoxy)ethyl, (3-methylbutoxy)ethyl, (2,2-dimethylpropoxy)ethyl, (1-ethylpropoxy)ethyl, n-hexyloxyethyl, (1,1-dimethylpropoxy)ethyl, (1,2-dimethylpropoxy) ethyl, (1-methylpentyloxy)ethyl, (2-methylpentyloxy) ethyl, (3-methylpentyloxy)ethyl, (4-methylpentyloxy)ethyl, (1,1-dimethylbutoxy) ethyl, (1,2-dimethylbutoxy)ethyl, (1,3-dimethylbutoxy)ethyl, (2,2-dimethylbutoxy)ethyl, (2,3-dimethylbutoxy)ethyl, (3,3-dimethylbutoxy) ethyl, (1-ethylbutoxy)ethyl, (2-ethylbutoxy)ethyl, (1,1,2-trimethylpropoxy)ethyl, (1,2,2-trimethylpropoxy)ethyl, (1-ethyl-1-methylpropoxy) ethyl, (1-ethyl-2-methylpropoxy)ethyl, 2-methoxypropyl, 3-methoxypropyl or 2-ethoxypropyl, preferably $C_1$–$C_6$-alkoxy-$C_1C_2$-alkyl, such as methoxymethyl, ethoxymethyl, 2-methoxyethyl or 2-ethoxyethyl;

$C_1$–$C_6$-alkylthio-$C_1$–$C_6$-alkyl: methylthiomethyl, ethylthiomethyl, n-propylthiomethyl, (1-methylethylthio)methyl, n-butylthiomethyl, (1-methylpropylthio)methyl, (2-methylpropylthio) methyl, (1,1-dimethylethylthio)methyl, n-pentylthiomethyl, (1-methylbutylthio)methyl, (2-methylbutylthio)methyl, (3-methylbutylthio) methyl, (2,2-dimethylpropylthio)methyl, (1-ethylpropylthio)methyl, n-hexylthiomethyl, (1,1-dimethylpropylthio)methyl, (1,2-dimethylpropylthio)methyl, (1-methylpentylthio) methyl, (2-methylpentylthio)methyl, (3-methylpentylthio)methyl, (4-methylpentylthio) methyl, (1,1-dimethylbutylthio)methyl, (1,2-dimethylbutylthio)methyl, (1,3-dimethylbutylthio) methyl, (2,2-dimethylbutylthio)methyl, (2,3-dimethylbutylthio)methyl, (3,3-dimethylbutylthio) methyl, (1-ethylbutylthio)methyl, (2-ethylbutylthio) methyl, (1,1,2-trimethylpropylthio)methyl, (1,2,2-trimethylpropylthio)methyl, (1-ethyl-1-methylpropylthio)methyl, (1-ethyl-2-methylpropylthio)methyl, methylthioethyl, ethylthioethyl, n-propylthioethyl, (1-methylethylthio)ethyl, n-butylthioethyl, (1-methylpropylthio)ethyl, (2-methylpropylthio)ethyl, (1,1-dimethylethylthio)ethyl, n-pentylthioethyl, (1-methylbutylthio) ethyl, (2-methylbutylthio)ethyl, (3-methylbutylthio)ethyl, (2,2-dimethylpropylthio) ethyl, (1-ethylpropylthio)ethyl, n-hexylthioethyl, (1,1-dimethyhlpropylthio)ethyl, (1,2-dimethylpropylthio)ethyl, (1-methylpentylthio) ethyl, (2-methylpentylthio)ethyl, (3-methylpentylthio)ethyl, (4-methylpentylthio)ethyl, (1,1-dimethylbutylthio)ethyl, (1,2-dimethylbutylthio) ethyl, (1,3-dimethylbutylthio)ethyl, (2,2-dimethylbutylthio)ethyl, (2,3-dimethylbutylthio) ethyl, (3,3-dimethylbutylthio)ethyl, (1-ethylbutylthio)ethyl, (2-ethylbutylthio)ethyl, (1,1,2-trimethylpropylthio)ethyl, (1,2,2-trimethylpropylthio)ethyl, (1-ethyl-1-methylpropylthio)ethyl, (1-ethyl-2-methylpropylthio)ethyl, 2-(methylthio) proypl, 3-(methylthio)propyl or 2-(ethylthio)propyl, preferably $C_1$–$C_6$-alkylthio-$C_1$–$C_2$-alkyl, such as methylthiomethyl, ethylthiomethyl, 2-methylthioethyl or 2-ethylthioethyl;

$C_1$–$C_6$-alkoximino: methoximino, ethoximino, n-propoximino, 1-methylethoximino, n-butoximino, 1-methylpropoximino, 2-methylpropoximino, 1,1-dimethylethoximino, n-pentyloximino, 1-methylbutoximino, 2-methylbutoximino, 3-methylbutoximino, 1,1-dimethylpropoximino, 1,2-dimethylpropoximino, 2,2-dimethylpropoximino, 1-ethylpropoximino, n-hexyloximino, 1-methylpentyloximino, 2-methylpentyloximino, 3-methylpentyloximino, 4-methylpentyloximino, 1,1-dimethylbutoximino, 1,2-dimethylbutoximino, 1,3-dimethylbutoximino, 2,2-dimethylbutoximino, 2,3-dimethylbutoximino, 3,3-dimethylbutoximino, 1-ethylbutoximino, 2-ethylbutoximino, 1,1,2-trimethylpropoximino, 1,2,2-trimethylpropoximino, 1-ethyl-1-methylpropoximino or 1-ethyl-2-methylpropoximino, preferably $C_1$–$C_4$-alkoximino, such as methoximino or ethoximino;

$C_1$–$C_6$-alkoximino-$C_1$–$C_6$-alkyl: methoximinomethyl, ethoximinomethyl, n-propoximinomethyl, (1-methylethoximino)methyl, n-butoximinomethyl, (1-methylpropoximino)methyl, (2-methylpropoximino)methyl, (1,1-dimethylethoximino) methyl, n-pentyloximinomethyl, (1-methylbutoximino)methyl, (2-methylbutoximino)methyl, (3-methylbutoximino)methyl, (2,2-dimethylpropoximino)methyl, (1-ethylpropoximino)methyl, n-hexyloximinomethyl, (1,1-dimethylpropoximino) methyl, (1,2-dimethylpropoximino)methyl, (1-methylpentyloximino)methyl, (2-methylpentyloximino)methyl, (3-methylpentyloximino) methyl, (4-methylpentoximino)methyl, (1,1-dimethylbutoximino)methyl, (1,2-dimethylbutoximino)methyl, (1,3-dimethylbutoximino methyl, (2,2-dimethylbutoximino)methyl, (2,3-dimethylbutoximino)methyl, (3,3-dimethylbutoximino)methyl, (1-ethylbutoximino)methyl, (2-ethylbutoximino)methyl, (1,1,2-trimethylpropoximino)methyl, (1,2,2-trimethylpropoximino)methyl, (1-ethyl-1-methylpropoximino)methyl, (1-ethyl-2-methylpropoximino)methyl, methoximinoethyl, ethoximinoethyl, n-propoximinoethyl, (1-methylethoximino)ethyl, n-butoximinoethyl, (1-methylpropoximino)ethyl, (2-methylpropoximino)ethyl, (1,1-dimethylethoximino)ethyl, n-pentyloximinoethyl, (1-methylbutoximino)ethyl, (2-methylbutoximino)ethyl, (3-methylbutoximino)ethyl, (2,2-dimethylpropoximino)ethyl, (1-ethylpropoximino)ethyl, n-hexyloximinoethyl, (1,1-dimethylpropoximino)ethyl, (1,2-dimethylpropoximino)ethyl, (1-methylpentyloximino)ethyl, (2-methylpentyloximino)ethyl, (3-methylpentyloximino)ethyl, (4-methylpentoximino)ethyl, (1,1-dimethylbutoximino)ethyl, (1,2-dimethylbutoximino)ethyl, (1,3-dimethylbutoximino)ethyl, (2,2-dimethylbutoximino)ethyl, (2,3-dimethylbutoximino)ethyl, (3,3-diethylbutoximino)ethyl, (1-ethylbutoximino)ethyl, (2-ethylbutoximino)ethyl, (1,1,2-trimethylpropoximino)ethyl, (1,2,2-trimethylpropoximino)ethyl, (1-ethyl-1-methylpropoximino)ethyl, (1-ethyl-2-methylpropoximino)ethyl, 2-(methoximino)propyl, 3-(methoximino)propyl or 2-(ethoximino)propyl, preferably $C_1$–$C_6$-alkoximino, $C_1$–$C_2$-alkyl, such as methoximinomethyl, ethoximinomethyl, 2-methoximinoethyl or 2-ethoximinoethyl;

$C_1$–$C_6$-alkoxy-$C_1$–$C_6$-alkoxy: methoxymethoxy, ethoxymethoxy, n-propoxymethoxy, (1-methylethyl)methoxy, n-butoxymethoxy, (1-methylpropoxy)methoxy, (2-methylpropoxy)methoxy, (1,1-dimethylethoxy) methoxy, n-pentyloxymethoxy, (1-methylbutoxy)methoxy, (2-methylbutoxy)methoxy, (3-methylbutoxy)methoxy, (2,2-dimethylpropoxy)methoxy, (1-ethylpropoxy)methoxy, n-hexyloxymethoxy, (1,1-dimethylpropoxy)methoxy, (1,2-dimethylpropoxy)methoxy, (1-methylpentyloxy)methoxy, (2-methylpentyloxy)methoxy, (3-methylpentyloxy)methoxy, (4-methylpentyloxy)methoxy, (1,1-dimethylbutoxy)methoxy, (1,2-dimethylbutoxy)methoxy, (1,3-dimethylbutoxy)methoxy, (2,2-dimethylbutoxy)methoxy, (2,3-dimethylbutoxy)methoxy, (3,3-dimethylbutoxy)methoxy, (1-ethylbutoxy)methoxy, (2-ethylbutoxy)methoxy, (1,1,2-trimethylpropoxy)methoxy, (1,2,2-trimethylpropoxy)methoxy, (1-ethyl-1-methylpropoxy)methoxy, (1-ethyl-2-methylpropoxy)methoxy, methoxyethoxy, ethoxyethoxy, n-propoxyethoxy, (1-methylethoxy)ethoxy, n-butoxyethoxy, (1-methylpropoxy)ethoxy, (2-methylpropoxy)ethoxy, (1,1-dimethylethoxy)ethoxy, n-pentyloxyethoxy, (1-methylbutoxy)ethoxy, (2-methylbutoxy)ethoxy, (3-methylbutoxy)ethoxy, (2,2-dimethylpropoxy)ethoxy, (1-ethylpropoxy)ethoxy, n-hexyloxyethoxy, (1,1-dimethylpropoxy)ethoxy, (1,2-dimethylpropoxy)ethoxy, (1-methylpentyloxy)ethoxy, (2-methylpentyloxy)ethoxy, (3-methylpentyloxy)ethoxy, (4-methylpentyloxy)ethoxy, (1,1-dimethylbutoxy)ethoxy,(1,2-dimethylbutoxy)ethoxy, (1,3-dimethylbutoxy)ethoxy, (2,2-dimethylbutoxy)ethoxy, (2,3-dimethylbutoxy)ethoxy, (3,3-dimethylbutoxy)ethoxy, (1-ethylbutoxy)ethoxy, (2-ethylbutoxy)ethoxy, (1,1,2-trimethylpropoxy)ethoxy, (1,2,2-trimethylpropoxy)ethoxy, (1-ethyl-1-methylpropoxy)ethoxy, (1-ethyl-2-methylpropoxy)ethoxy, 3-(methoxy)propoxy, 2-(methoxy)propoxy or 2-(ethoxy)propoxy, preferably $C_1$–$C_6$-alkoxy-$C_1$–$C_2$-alkoxy, such as methoxymethoxy, ethoxymethoxy, 2-methoxyethoxy or 2-ethoxyethoxy;

$C_1$–$C_6$-alkylthio-$C_1$–$C_6$-alkoxy; methylthiomethoxy, ethylthiomethoxy, n-propylthiomethoxy, (1-methylethylthio)methoxy, n-butylthiomethoxy, (1-methylpropylthio)methoxy, (2-methylpropylthio)methoxy, (1,1-dimethylethylthio)methoxy, n-pentylthiomethoxy, (1-methylbutylthio)methoxy, (2-methylbutylthio)methoxy, (3-methylbutylthio)methoxy, (2,2-dimethylpropylthio)methoxy, (1-ethylpropylthio)methoxy, n-heyxylthiomethoxy, (1,1-dimethylpropylthio)methoxy, (1,2-dimethylpropylthio)methoxy, (1-methylpentylthio)methoxy, (2-methylpentylthio)methoxy, (3-methylpentylthio)methoxy, (4-methylpentylthio)methoxy, (1,1-dimethylbutylthio)methoxy, (1,2-dimethylbutylthio)methoxy, (1,3-dimethylbutylthio)methoxy, (2,2-dimethylbutylthio)methoxy, (2,3-dimethylbutylthio)methoxy, (3,3-dimethylbutylthio)methoxy, (1-ethylbutylthio)methoxy,(2-ethylbutylthio)methoxy, (1,1,2-trimethylpropylthio)methoxy, (1,2,2-trimethylpropylthio)methoxy, (1-ethyl-1-methylpropylthio)methoxy, (1-ethyl-2-methylpropylthio)methoxy, methylthioethoxy, ethylthioethoxy, n-propylthioethoxy, (1-methylethylthio)ethoxy, n-butylthioethoxy, (1-methylpropylthio)ethoxy, (2-methylpropylthio)ethoxy, (1,1-dimethylethylthio)ethoxy, n-pentylthio)ethoxy, (1-methylbutylthio)ethoxy, (2-methylbutylthio)ethoxy, (3-methylbutylthio)ethoxy, (2,2-dimethylpropylthio)ethoxy, (1-ethylpropylthio)ethoxy, n-hexylthioethoxy, (1,1-dimethylpropylthio)ethoxy, (1,2-dimethylpropylthio)ethoxy, (1-methylpentylthio)ethoxy, (2-methylpentylthio)ethoxy, (3-methylpentylthio)ethoxy, (4-methylpentylthio)ethoxy, (1,1-dimethylbutylthio)ethoxy, (1,2-dimethylbutylthio)ethoxy, (1,3-dimethylbutylthio)ethoxy, (2,2-dimethylbutylthio)ethoxy, (2,3-dimethylbutylthio)ethoxy, (3,3-dimethylbutylthio)ethoxy, (1-ethylbutylthio)ethoxy, (2-ethylbutylthio)ethoxy, (1,1,2-trimethylpropylthio)ethoxy, (1,2,2-trimethylpropylthio)ethoxy, (1-ethyl-1-methylpropylthio)ethoxy, (1-ethyl-2-methylpropylthio)ethoxy, 2-(methylthio)propoxy, 3-(methylthio)propoxy or 2-(ethylthio)propoxy, preferably $C_1$–$C_6$-alkylthio-$C_1$–$C_2$-alkoxy, such as methylthiomethoxy, ethylthiomethoxy, 2-methylthioethoxy or 2-ethylthioethoxy;

$C_1$–$C_6$-alkylamino-$C_1$–$C_6$-alkoxy: methylaminomethoxy, ethyl-aminomethoxy, n-propylaminoethoxy, (1-methylethylamino)methoxy, n-butylaminomethoxy, (1-methylpropylamino)methoxy, (2-methylpropylamino)methoxy, (1,1-dimethylethylamino)methoxy, n-pentylamino)methoxy, (1-methylbutylamino)methoxy, (2-methylbutylamino)methoxy, (3-methylbutylamino)methoxy, (2,2-dimethylpropylamino)methoxy, (1-ethylpropylamino) methoxy, n-hexylaminoethoxy, (1,1-dimethylpropylamino)methoxy, (1,2-dimethylpropylamino) methoxy, (1-methylpentylamino)methoxy, (2-methylpentylamino)methoxy, (3-methylpentylamino)methoxy, (4-methylpentylamino) methoxy, (1,1-dimethylbutylamino)methoxy, (1,2-dimethylbutylamino)methoxy, (1,3-dimethylbutylamino)methoxy, (2,2-dimethylbutylamino) methoxy, (2,3-dimethylbutylamino)methoxy, (3,3-dimethylbutylamino)methoxy, (1-ethylbutylamino) methoxy, (2-ethylbutylamino)methoxy, (1,1,2-trimethylpropylamino)methoxy, (1,2,2-trimethylpropylamino)methoxy, (1-ethyl-1-methylpropylamino)methoxy, (1-ethyl-2-methylpropylamino)methoxy, methylaminoethoxy, ethylaminoethoxy, n-propylaminoethoxy, (1-methylethylamino)ethoxy, n-butylaminoethoxy, (1-methylpropylamino)ethoxy, (2-methylpropylamino)ethoxy, (1,1-dimethylethylamino) ethoxy, n-pentylamino)ethoxy, (1-methylbutylamino)ethoxy, (2-methylbutylamino)ethoxy, (3-methylbutylamino)ethoxy, (2,2-dimethylpropylamino)ethoxy, (1-ethylpropylamino)ethoxy, n-hexylaminoethoxy, (1,1-dimethylpropylamino) ethoxy, (1,2-dimethylpropylamino)ethoxy, (1-methylpentylamino)ethoxy, (2-methylpentylamino)ethoxy, (3-methylpentylamino)ethoxy, (4-methylpentylamino)ethoxy, (1,1-dimethylbutylamino)ethoxy, (1,2-dimethylbutylamino) ethoxy, (1,3-dimethylbutylamino)ethoxy, (2,2-dimethylbutylamino)ethoxy, (2,3-dimethylbutylamino)ethoxy, (3,3-dimethylbutylamino) ethoxy, (1-ethylbutylamino)ethoxy, (2-ethylbutylamino)ethoxy, (1,1,2-trimethylpropylamino) ethoxy, (1,2,2-trimethylpropylamino)ethoxy, (1-ethyl-1-methylpropylamino)ethoxy, (1-ethyl-2-methylpropylamino)ethoxy, 2-(methylamino) propoxy, 3-(methylamino)propoxy or 2-(ethylamino)propoxy, preferably $C_1$–$C_6$-alkylamino-$C_1$–$C_2$-alkoxy, such as methylaminomethoxy, ethylaminomethoxy, 2-methylaminoethoxy or 2-ethylaminoethoxy;

di-$C_1$–$C_6$-alkylamino-$C_1$–$C_6$-alkoxy: N,N-dimethylamionomethoxy, N,N-diethylaminomethoxy, N,N-dipropylaminomethoxy, N,N-di-(1-methylethyl)aminomethoxy, N,N-dibutylaminomethoxy, N,N-di-(1-methylpropyl) aminomethoxy, N,N-di-(2-methylpropyl) aminomethoxy, N,N-di-(1,1-dimethylethyl) aminomethoxy, N-ethyl-N-methylaminomethoxy, N-methyl-N-propylaminomethoxy, N-methyl-N-(1-methylethyl)aminomethoxy, N-butyl-N-methylaminomethoxy, N-methyl-N-(1-methylpropyl)aminomethoxy, N-methyl-N-(2-methylpropyl)aminomethoxy, N-(1,1-dimethylethyl)-N-methylaminomethoxy, N-ethyl-N-propylaminomethoxy, N-ethyl-N-(1-methylethyl) aminomethoxy, N-butyl-N-ethylaminomethoxy, N-ethyl-N-(1-methylpropyl)aminomethoxy, N-ethyl-N-(2-methylpropyl)aminomethoxy, N-ethyl-N-(1,1-dimethylethyl)aminomethoxy, N-(1-methylethyl)-N-propylaminomethoxy, N-butyl-N-propylaminomethoxy, N-(1-methylpropyl)-N-propylaminomethoxy, N-(2-methylpropyl)-N-propylaminomethoxy, N-butyl-N-(1-methylethyl) aminomethoxy, N-(1-methylethyl)-N-(1-methylpropyl)aminomethoxy, N-(1-methylethyl)-N-(2-methylpropyl)aminomethoxy, N-(1,1-dimethylethyl)-N-(1-methylethyl)aminomethoxy, N-butyl-N-(1-methylpropyl)aminomethoxy, N-butyl-N-(2-methylpropyl)aminomethoxy, N-butyl-N-(1,1-dimethylethyl)aminomethoxy, N-(1-methylpropyl)-N-(2-methylpropyl)aminomethoxy, N-(1,1-dimethylethyl)-N-(1-methylpropyl) aminomethoxy, N-(1,1-dimethylethyl)-N-(2-methylpropyl)aminomethoxy, N,N-dimethylaminoethoxy, N,N-diethylaminoethoxy, N,N-di-(n-propyl)aminoethoxy, N,N-di-(1-methylethyl)aminoethoxy, N,N-dibutylaminoethoxy, N,N-di-(1-methylpropyl)aminoethoxy, N,N-di-(2-methylpropyl)aminoethoxy, N,N-di-(1,1-dimethylethyl)aminoethoxy, N-ethyl-N-methylaminoethoxy, N-methyl-N-propylaminoethoxy, N-methyl-N-(1-methylethyl) aminoethoxy, N-butyl-N-methylaminoethoxy, N-methyl-N-(1-methylpropyl)aminoethoxy, N-methyl-N-(2-methylpropyl)aminoethoxy, N-(1,1-dimethylethyl)-N-methylaminoethoxy, N-ethyl-N-propylaminoethoxy, N-ethyl-N-(1-methylethyl) aminoethoxy, N-butyl-N-ethylaminoethoxy, N-ethyl-N-(1-methylpropyl)aminoethoxy, N-ethyl-N-(2-methylpropyl)aminoethoxy, N-ethyl-N-(1,1-dimethylethyl)aminoethoxy, N-(1-methylethyl)-N-propylaminoethoxy, N-butyl-N-propylaminoethoxy, N-(1-methylpropyl)-N-propylaminoethoxy, N-(2-methylpropyl)-N-propylaminoethoxy, N-(1,1-dimethylethyl)-N-propylaminoethoxy, N-butyl-N-(1-methylethyl)aminoethoxy, N-(1-methylethyl)-N-(1-methylpropyl)aminoethoxy, N-(1-methylethyl)-N-(2-methylpropyl)aminoethoxy, N-(1,1-dimethylethyl)-N-(1-methylethyl)aminoethoxy, N-butyl-N-(1-methylpropyl)aminoethoxy, N-butyl-N-(2-methylpropyl)aminoethoxy, N-butyl-N-(1,1-dimethylethyl)aminoethoxy, N-(1-methylpropyl)-N-(2-methylpropyl)aminoethoxy, N-(1,1-dimethylethyl)-N-(1-methylpropyl)aminoethoxy or N-(1,1-dimethylethyl)-N-(2-methylpropyl) aminoethoxy;

$C_1$–$C_6$-alkylcarbonyl: methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropoxycarbonyl, preferably $C_1$–$C_4$-alkylcarbonyl, such as methylcarbonyl or ethylcarbonyl;

$C_1$–$C_6$-alkoxycarbonyl and the $C_1$–$C_6$-alkoxycarbonyl moieties in the radicals $C_1$–$C_6$-alkoxycarbonyl-$C_2$–$C_6$-alkyl, $C_1$–$C_6$-alkoxycarbonyl-$C_1$–$C_6$-alkoxy and $C_1$–$C_6$-alkoxy-$C_1$–$C_6$-alkoxycarbonyl-$C_1$–$C_6$-alkyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl,1,1-dimethylpropoxycarbonyl,1,2-dimethylpropoxycarbonyl, 2,2-dimethylpropoxycarbonyl, 1-ethylpropoxycarbonyl, hexyloxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, preferably $C_1$–$C_4$-alkoxycarbonyl, such as methoxycarbonyl or ethoxycarbonyl;

$C_1$–$C_6$-alkylaminocarbonyl: methylaminocarbonyl, ethylaminocarbonyl, n-propylaminocarbonyl, 1-methyhlethylaminocarbonyl, n-butylaminocarbonyl, 1-methylpropylaminocarbonyl, 2-methylpropylaminocarbonyl, 1,1-dimethylethylaminocarbonyl, n-pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, n-hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methyl- propylaminocarbonyl or 1-ethyl-2-methylpropylaminocarbonyl, preferably $C_1$–$C_4$-alkylaminocarbonyl, such as methylaminocarbonyl or ethylaminocarbonyl;

di-$C_1$–$C_6$-alkylaminocarbonyl: N,N-dimethyhlaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N--butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl) aminocarbonyl or N-(1,1-dimethylethyl)-N-(2-methylpropyl)aminocarbonyl, preferably dimethylaminocarbonyl or diethylaminocarbonyl;

$C_1$–$C_6$-alkylcarbonyloxy: acetoxy, propionyloxy, butyryloxy, alpha-methylpropionyloxy, n-butylcarbonyloxy, 1-methylpropylcarbonyloxy, 2-methylpropylcarbonyloxy, 1,1-dimethylethylcarbonyloxy, n-pentylcarbonyloxy, 1-methylbutylcarbonyloxy, 2-methylbutylcarbonyloxy, 3-methylbutylcarbonyloxy, 1,1-dimethylpropylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methylpentylcarbonyloxy, 3-methylpentylcarbonyloxy, 4-methylpentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropylcarbonyloxy, 1,2,2-trimethylpropylcarbonyloxy, 1-ethyl-1-methylpropylcarbonyloxy or 1-ethyl-2-methylpropylcarbonyloxy, preferably $C_1$–$C_4$-alkylcarbonyloxy, such as methylcarbonyloxy or ethylcarbonyloxy;

$C_1$–$C_6$-alkoxycarbonyl-$C_1$–$C_6$-alkyl: methoxycarbonylmethyl, ethoxycarbonylmethyl, n-propoxycarbonylmethyl, (1-meth- ylethoxycarbonyl)methyl, n-butoxycarbonylmethyl, (1-methylpropoxycarbonyl)methyl, (2-methylpropoxycarbonyl)methyl, (1,1-dimethylethoxycarbonyl)methyl, n-pentyloxycarbonylmethyl, (1-methylbutoxycarbonyl)methyl, (2-methylbutoxycarbonyl)methyl, (3-methylbutoxycarbonyl)methyl, (1,1-dimethylpropoxycarbonyl)methyl, (1,2-dimethylpropoxycarbonyl)methyl, (2,2-dimethylpropoxycarbonyl)methyl, (1-ethylpropoxycarbonyl)methyl, n-hexyloxycarbonylmethyl, (1-methyl- pentyloxycarbonyl)methyl, (2-methylpentyloxycarbonyl)methyl, (3-methylpentyloxycarbonyl)methyl, (4-methylpentyloxycarbonyl)methyl, (1,1-dimethylbutoxycarbonyl)methyl, (1,2-dimethylbutoxycarbonyl)methyl, (1,3-dimethylbutoxycarbonyl)methyl, (2,2-dimethylbutoxycarbonyl)methyl, (2,3-dimethylbutoxycarbonyl)methyl, (3,3-dimethylbutoxycarbonyl)methyl, (1-ethylbutoxycarbonyl)methyl, (2-ethylbutoxycarbonyl)methyl, (1,1,2-trimethylpropoxycarbonyl)methyl, (1,2,2-trimethylpropoxycarbonyl)methyl, (1-ethyl-1-methylpropoxycarbonyl)methyl, (1-ethyl-2- methylpropylcarbonyl)methyl, methoxycarbonylethyl, ethoxycarbonylethyl, n-propoxycarbonylethyl, (1-methylethoxycarbonyl) ethyl, n-butoxycarbonylethyl, (1-methylpropoxycarbonyl)ethyl, (2-methylpropoxycarbonyl)ethyl, (1,1-dimethylethoxycarbonyl)ethyl, n-pentyloxycarbonylethyl, (1-methylbutoxycarbonyl)ethyl, (2-methylbutoxycarbonyl)ethyl, (3-methylbutoxycarbonyl)ethyl, (1,1-dimethylpropoxycarbonyl)ethyl, (1,2-dimethylpropoxycarbonyl)ethyl, (2,2-dimethylpropoxycarbonyl)ethyl, (1-ethylpropoxycarbonyl)ethyl, n-hexyloxycarbonylethyl, (1-methylpentyloxycarbonyl)ethyl, (2-methylpentyloxycarbonyl) ethyl, (3-methylpentyloxycarbonyl)ethyl, (4-methylpentyloxycarbonyl)ethyl, (1,1-dimethylbutoxycarbonyl)ethyl, (1,2-dimethylbutoxycarbonyl)ethyl, (1,3-dimethylbutoxycarbonyl)ethyl, (2,2-dimethylbutoxycarbonyl) ethyl, (2,3-dimethylbutoxycarbonyl)ethyl, (3,3-dimethylbutoxycarbonyl)ethyl, (1-ethylbutoxycarbonyl)ethyl, (2-ethylbutoxycarbonyl) ethyl, (1,1,2-trimethylpropoxycarbonyl)ethyl, (1,2,2-trimethylpropoxycarbonyl)ethyl, (1-ethyl-1-methylpropoxycarbonyl)ethyl, (1-ethyl-2-methylpropylcarbonyl)ethyl, 3-(methoxycarbonyl) propyl, 2-(methoxycarbonyl)propyl or 2-(ethoxycarbonyl)propyl, preferably $C_1$–$C_4$-alkoxycarbonyl-$C_1$-or $C_2$-alkyl, such as methoxycarbonylmethyl, ethoxycarbonylmethyl, 2-methoxycarbonylethyl or 2-ethoxycarbonylethyl; heterocyclyl and the heterocyclyl radical in the heterocyclyl-$C_1$–$C_6$-alkyl group, where the heterocyclic structure in each case may be saturated or partially or completely unsaturated and may carry from one to four hetero atoms: Tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,3,4-oxadiazolidinyl, 1,2,4-thiadiazolidinyl, 1,3,4-thiadiazolidinyl, 1,2,4-triazolidinyl, 1,3,4-triazolidin-2-yl, 2,3-dihydrofuryl, 2,4-dihydrofuryl, 2,3-dihydrothienyl, 2,4-dihydrothienyl, 2,3-pyrrolin-2-yl, 2,4-pyrrolinyl, 2,3-isoxazolinyl, 3,4-isoxazolinyl, 4,5-isoxazolinyl,2,3-isothiazolinyl,3,4-isothiazolinyl, 4,5-isothiazolinyl, 2,3-dihydropyrazolyl, 3,4-dihydropyrazolyl, 4,5-dihydropyrazol-1-yl, 2,3-dihydrooxazolyl, 3,4-dihydrooxazolyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl or 1,2,4-tetrahydrotriazin-3-yl, furanyl, thienyl, pyrrolyl, isoxazolyl, isothiazolyl, pyrazolyl, oxazolyl, thiazolyl, imidazolyl, 1,2,4-oxadiazolyl, 1,3,4-oxadiazolyl, 1,2,4-thiadiazolyl, 1,3,4-thiadiazolyl, 1,2,4-triazolyl, 1,3,4-triazolyl, pyridyl, pyridazinyl, pyrimidinyl, pyrazinyl, 1,2,4-triazinyl, 1,3,5-triazinyl, dihydropyran-2-yl, dihydropyran-3-yl, dihydropyran-4-yl, dihydrothiopyran-2-yl, dihydrothiopyran-3-yl, dihydrothiopyran-4-yl, tetrahydropyran-2-yl, tetrahydropyran-3-yl, tetrahydropyran-4-yl, tetrahydrothiopyran-2-yl, tetrahydrothiopyran-3-yl or tetrahydrothiopyran-4-yl,

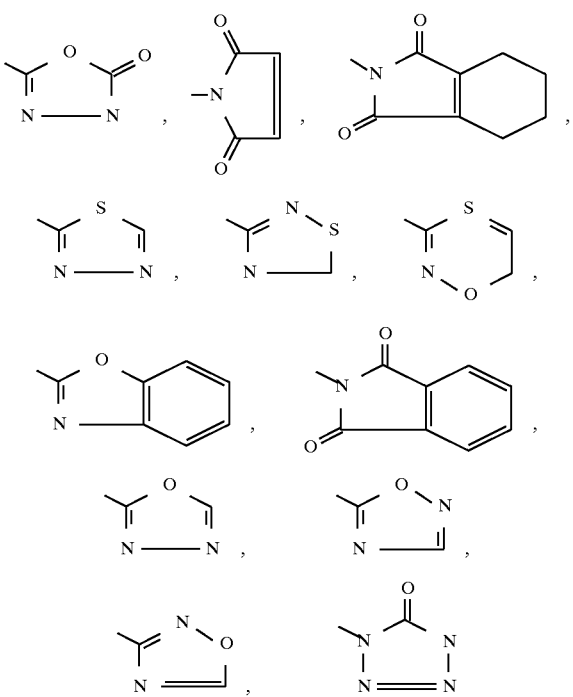

The substituted cyclohexene-1,2-dicarboxylic acid derivatives Ia and Ib may be present in the form of their agriculturally useful salts, suitable salts being in general those of bases which do not adversely affect the herbicidal action of Ia and Ib.

Particularly suitable basic salts are those of the alkali metals, preferably the sodium and potassium salts, those of the alkaline earth metals, preferably calcium, magnesium and barium salts, and those of the transition metals, preferably manganese, copper, zinc and iron salts, as well as the ammonium salts which may carry from one to three $C_1$–$C_4$-alkyl or hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl(2-hydroxyethyl)ammonium salts, the phosphonium salts, the sulfonium salts, preferably tri-$C_1$–$C_4$-alkylsulfonium salts, and the sulfoxonium salts, preferably tri-$C_1$–$C_4$-alkylsulfoxonium salts.

In view of the use of the novel cyclohexene-1,2-dicarboxylic acid derivatives Ia and Ib, tetrahydrophthalimides IIa, tetrahydroisophthalimides IIIa and tetrahydrophthalamic esters VIIIa as herbicidal and defoliant/desiccant compounds, the variables preferably have the following meanings:

$R^1$ and $R^2$, independently of one another, are each a radical from the group 1.01–1.179 or $R^1$ and $R^2$ together form a radical from the group 2.01–2.07, $R^3$ is a radical from the group 3.01–3.09, $R^4$ is a radical from the group 4.01–4.08, $R^5$ is a radical from the group 5.01–5.08, $R^5$ and $R^6$ together form a radical from the group 56.01–56.31, $R^6$ is a radical from the group 6.01–6.08, where $X^1$ and $X^2$ independently of one another are each oxygen or sulfur, A is a radical from the group A.01–A.32, B is a radical from the group B.01–B.138, $R^9$ is a radical from the group 9.01–9.109,
$R^{10}$ is a radical from the group 10.01–10.22,
$R^{11}$ is a radical from the group 11.01–11.08,
$R^{12}$ is a radical from the group 12.01–12.17,
$R^{16}$ is a radical from the group 16.01–16.161,
$R^{14}$ and $R^{15}$ independently of one another are each a radical from the group 14.01–14.17 or
$R^{14}$ and $R^{15}$ together form a radical from the group 15.01–15.60, it being possible for $R^1$, $R^2$, $R^3$, $R^4$, $R^5$ and $R^6$ to be freely combined with one another, with the proviso that $R^1$ may be only 1.01 to 1.08 when $R^2$ is 1.05 to 1.156.

TABLE 1

| No. | $R^1$, $R^2$ |
|---|---|
| 1.01 | H |
| 1.02 | $CH_3$ |
| 1.03 | $C_2H_5$ |
| 1.04 | $n-C_3H_7$ |
| 1.05 | $i-C_3H_7$ |
| 1.06 | $n-C_4H_9$ |
| 1.07 | $n-C_5H_{11}$ |
| 1.08 | $n-C_6H_{13}$ |
| 1.09 | $CH_2CH=CH_2$ |
| 1.10 | $CH(CH_3)-CH=CH_2$ |
| 1.11 | $CH_2-CH=CH-CH_2$ |
| 1.12 | $CH_2-C\equiv CH$ |
| 1.13 | $CH(CH_3)-C\equiv CH$ |
| 1.14 | $CH_2-C\equiv C-CH_3$ |
| 1.15 | Cyclopropyl |
| 1.16 | Cyclobutyl |
| 1.17 | Cyclopentyl |
| 1.18 | Cyclohexyl |
| 1.19 | Cycloheptyl |
| 1.20 | $(CH_2)_2Cl$ |
| 1.21 | $CH_2Cl$ |
| 1.22 | Phenyl |
| 1.23 | 2-F-phenyl |
| 1.24 | 3-F-phenyl |
| 1.25 | 4-F-phenyl |
| 1.26 | 2-Cl-phenyl |
| 1.27 | 3-Cl-phenyl |
| 1.28 | 4-Cl-phenyl |
| 1.29 | 2-Br-phenyl |
| 1.30 | 3-Br-phenyl |
| 1.31 | 4-Br-phenyl |
| 1.32 | $2-CH_3$-phenyl |
| 1.33 | $3-CH_3$-phenyl |
| 1.34 | $4-CH_3$-phenyl |
| 1.35 | $2-CF_3$-phenyl |
| 1.36 | $3-CF_3$-phenyl |
| 1.37 | $4-CF_3$-phenyl |
| 1.38 | $2-OCH_3$-phenyl |
| 1.39 | $3-OCH_3$-phenyl |
| 1.40 | $4-OCH_3$-phenyl |
| 1.41 | $4-NO_2$-phenyl |
| 1.42 | $4-CN$-phenyl |
| 1.43 | $2,4-Cl_2$-phenyl |
| 1.44 | $2,4-(CH_3)_2$-phenyl |
| 1.45 | $CH_2-OCH_3$ |
| 1.46 | $(CH_2)_2-OC_2H_5$ |
| 1.47 | OH |
| 1.48 | $OCH_3$ |
| 1.49 | $OC_2H_5$ |
| 1.50 | $O-n-C_3H_7$ |
| 1.51 | $O-i-C_3H_7$ |
| 1.52 | $O-n-C_4H_9$ |
| 1.53 | $O-i-C_4H_9$ |
| 1.54 | $O-s-C_4H_9$ |
| 1.55 | $O-tert.-C_4H_9$ |
| 1.56 | $O-CH_2CH=CH_2$ |
| 1.57 | $O-CH(CH_3)CH=CH_2$ |
| 1.58 | $O-CH_2C\equiv CH$ |
| 1.59 | $O-CH(CH_3)-C\equiv CH$ |
| 1.60 | $O-CH_2-C\equiv C-CH_3$ |
| 1.61 | $O-CH_2-CH=CH-CH_3$ |
| 1.62 | O-cyclopentyl |

TABLE 1-continued

| No. | $R^1$, $R^2$ |
|---|---|
| 1.63 | O-cyclohexyl |
| 1.64 | O-cyclopent-3-enyl |
| 1.65 | O-cyclohex-3-enyl |
| 1.66 | $O-(CH_2)_2-Cl$ |
| 1.67 | $O-(CH_2)_2-Cl$ |
| 1.68 | $O-(CH_2)-F$ |
| 1.69 | $O-CH_2-CF_3$ |
| 1.70 | $O-(CH_2)_2-Br$ |
| 1.71 | $O-CH_2-CH=CHCl$ |
| 1.72 | $O-CH_2-C(Cl)=CH_2$ |
| 1.73 | $O-CH_2-C(Br)=CH_2$ |
| 1.74 | $O-CH_2-CH=C(Cl)-CH_3$ |
| 1.75 | $O-CH_2-C(Cl)=CCl_2$ |
| 1.76 | $O-CH_2$-cyclopropyl |
| 1.77 | $O-CH_2$-cyclobutyl |
| 1.78 | $O-CH_2$-cyclopentyl |
| 1.79 | $O-CH_2$-cyclohexyl |
| 1.80 | $O-CH_2$-cycloheptyl |
| 1.81 | $O-CO-CH_3$ |
| 1.82 | $O-CO-C_2H_5$ |
| 1.83 | $O-CH_2-CN$ |
| 1.84 | $O-(CH_2)_3-CN$ |
| 1.85 | $O-CH_2-OCH_3$ |
| 1.86 | $O-CH_2-OC_2H_5$ |
| 1.87 | $O-(CH_2)_2-OCH_3$ |
| 1.88 | $O-(CH_2)_2-OC_2H_5$ |
| 1.89 | $O-(CH_2)_3-OC_2H_5$ |
| 1.90 | $O-(CH_2)_2-CO-OCH_3$ |
| 1.91 | $O-(CH_2)_2-CO-OC_2H_5$ |
| 1.92 | $O-C(CH_3)-CO-OCH_3$ |
| 1.93 | $O-C(CH_3)-CO-OC_2H_5$ |
| 1.94 | $O-(CH_2)_2-OH$ |
| 1.95 | $O-CH_2-SCH_3$ |
| 1.96 | $O-(CH_2)_2-N(CH_3)_2$ |
| 1.97 | $O-(CH_2)_2-N(C_2H_5)_2$ |
| 1.98 | $O-CH_2$-phenyl |
| 1.99 | $O-(CH_2)_2$-phenyl |
| 1.100 | $O-(CH_2)_3$-phenyl |
| 1.101 | $O-(CH_2)_4$-phenyl |
| 1.102 | $O-(CH_2)_4-(_4-Cl$-phenyl) |
| 1.103 | $O-(CH_2)_4-(4-CH_3$-phenyl) |
| 1.104 | $O-(CH_2)_4-(4-CH_3$-phenyl) |
| 1.105 | $O-(CH_2)_4-(4-F$-phenyl) |
| 1.106 | $O-CH_2CH=CH$-phenyl |
| 1.107 | $O-CH_2CH=CH(4-F$-phenyl) |
| 1.108 | $O-CH_2CH=CH-(4-Cl$-phenyl) |
| 1.109 | $O-CH_2CH=CH-(3-OCH_3$-phenyl) |
| 1.110 | $O-(CH_2)_2-CH=CH-(4-F$-phenyl) |
| 1.111 | $O-(CH_2)_2-CH=CH-(4-Cl$-phenyl) |
| 1.112 | $O-(CH_2)-CH=CH-(3,4-Cl_2$-phenyl) |
| 1.113 | $O-CH_2-CH=C(CH_3)-(4-F$-phenyl) |
| 1.114 | $O-CH_2-C\equiv C-CH_2$-phenyl |
| 1.115 | $O-(CH_2)_2-O$-phenyl |
| 1.116 | $O-(CH_2)_2-OCH_2$-phenyl |
| 1.117 | $O-(CH_2)_2-OCH_2-(4-F$-phenyl) |
| 1.118 | $O-CH_2CH=CH-CH_2-O$-phenyl |
| 1.119 | $O-CH_2-C\equiv C-CH_2-O$-phenyl |
| 1.120 | $O-CH_2-C\equiv C-CH_2-O-(4-F$-phenyl) |
| 1.121 | $O-(CH_2)_2-SCH_2$-phenyl |
| 1.122 | $O-(CH_2)_2-SCH_2-(4-Cl$-phenyl) |
| 1.123 | $O-(CH_2)_2-N(CH_3)-CH_2$-phenyl |
| 1.124 | $NH_2$ |
| 1.125 | $NHCH_3$ |
| 1.126 | $NH-C_2H_5$ |
| 1.127 | $NH-n-C_3H_7$ |
| 1.128 | $NH-i-C_3H_7$ |
| 1.129 | $NH-n-C_4H_9$ |
| 1.130 | $NH-i-C_4H_9$ |
| 1.131 | $NH-s-C_4H_9$ |
| 1.132 | $NH-tert.-C_4H_9-$ |
| 1.133 | NH-cyclopropyl |
| 1.134 | NH-cyclobutyl |
| 1.135 | NH-cyclopentyl |
| 1.136 | NH-cyclohexyl |
| 1.137 | NH-cycloheptyl |
| 1.138 | $N(CH_3)_2$ |
| 1.139 | $N(C_2H_5)_2$ |

TABLE 1-continued

| No. | $R^1, R^2$ |
|---|---|
| 1.140 | NH—CH$_2$CH=CH$_2$ |
| 1.141 | NH—CH$_2$C≡CH |
| 1.142 | NH—CH$_2$—CF$_3$ |
| 1.143 | NH—CO-CH$_3$ |
| 1.144 | NH—COC$_2$H$_5$ |
| 1.145 | NH—CO—OCH$_3$ |
| 1.146 | NH—CO—OC$_2$H$_5$ |
| 1.147 | NH—COO-tert.-C$_4$H$_9$ |
| 1.148 | NH-phenyl |
| 1.149 | NH-(4-Cl-phenyl) |
| 1.150 | NH-(4-F-phenyl) |
| 1.151 | NH-(4-OCH$_3$-phenyl) |
| 1.152 | NH-(2,4-Cl$_2$-phenyl) |
| 1.153 | CH$_2$—OCH$_3$ |
| 1.154 | (CH$_2$)$_2$—OCH$_3$ |
| 1.155 | CH$_2$COOCH$_3$ |
| 1.156 | CH$_2$COOC$_2$H$_5$ |
| 1.157 | CH(CH$_3$)—COOCH |
| 1.158 | CH(CH$_3$)—COOC$_2$H$_3$ |
| 1.159 | (CH$_2$)$_2$—COOCH$_3$ |
| 1.160 | (CH$_2$)$_3$—COOCH$_3$ |
| 1.161 | CH(COOH)CH$_3$ |
| 1.162 | CH(COOH)CH$_2$OH |
| 1.163 | CH(COOH)CH(CH$_3$)—OH |
| 1.164 | CH(COOH)CH$_2$-Phenyl |
| 1.165 | CH(COOH)CH$_2$-4-OH-Phenyl |
| 1.166 | CH(COOH)(CH$_2$)$_4$—NH$_2$ |
| 1.167 | CH(COOH)(CH$_2$)$_2$COOH |
| 1.168 | CH(COOH)(CH$_2$)$_3$COOH |
| 1.169 | CH(COOH)CH$_2$—CONH$_2$ |
| 1.170 | CH(COOH)(CH$_2$)$_2$—CONH$_2$ |
| 1.171 | CH(COOH)CH$_2$SH |
| 1.172 | CH(COOH)CH$_2$SCH$_3$ |
| 1.173 | CH(COOH)CH$_2$—CH(COOH)$_2$ |
| 1.174 | CH(COOH)CH$_2$-imidazol-3-yl |
| 1.175 | CH(COOH)CH$_2$-inden-3-yl |

TABLE 2

| No. | —NR$^1$R$^2$ |
|---|---|
| 2.01 | N-Pyrrolidinyl |
| 2.02 | N-Piperdinyl |
| 2.03 | N-Morpholino |
| 2.04 | N-Piperazinyl |
| 2.05 | N-Prolinyl |
| 2.06 | N-4-Hydroxyprolinyl |
| 2.07 | N-Prolinolyl |

TABLE 3

| No. | $R^3$ |
|---|---|
| 3.01 | CH$_3$ |
| 3.02 | C$_2$H$_5$ |
| 3.03 | n-C$_3$H$_7$ |
| 3.04 | i-C$_3$H$_7$ |
| 3.05 | n-C$_4$H$_9$ |
| 3.06 | i-C$_4$H$_9$ |
| 3.07 | s-C$_4$H$_9$ |
| 3.08 | tert.-C$_4$H$_9$ |
| 3.09 | H |

TABLE 4

| No. | $R^4$ |
|---|---|
| 4.01 | H |
| 4.02 | F |
| 4.03 | Cl |
| 4.04 | Br |
| 4.05 | I |

TABLE 5

| No. | $R^5$ |
|---|---|
| 5.01 | F |
| 5.02 | Cl |
| 5.03 | Br |
| 5.04 | I |
| 5.05 | CN |
| 5.06 | NO$_2$ |
| 5.07 | CF$_3$ |
| 5.08 | H |

TABLE 6

| No. | $R^5, R^6$ |
|---|---|
| 56.01 | —O—CH$_2$—CO—N(CH$_3$)— |
| 56.02 | —O—CH$_2$—CO—NH— |
| 56.03 | —O—CH$_2$CO—N(CH$_2$C≡CH)— |
| 56.04 | —O—CH(CH$_3$)—CO—N(CH$_2$C≡CH) |
| 56.05 | —O—CH(CH$_3$)—CO—N(i-C$_3$H$_7$)— |
| 56.06 | —O—CH$_2$—CO—N(i-C$_3$H$_7$)— |
| 56.07 | —S—CH$_2$—CO—N(CH$_2$C≡CH)— |
| 56.08 | —CH$_2$—CH$_2$—CO—N(CH$_2$C≡CH)— |
| 56.09 | —O—CO—N(CH$_3$)— |
| 56.10 | —O—CO—N(CH$_2$C≡CH)— |
| 56.11 | —S—CO—N(CH$_3$)— |
| 56.12 | —S—CO—N(CH$_2$C≡CH)— |
| 56.13 | —N=CH—CO—N(CH$_2$C≡CH)— |
| 56.14 | —N=CH—CO—N(CH$_3$)— |
| 56.15 | —N=CH—CO—N(i-C$_3$H$_7$) |
| 56.16 | —O—(CH$_2$)$_2$—C(=N—OCH$_3$)— |
| 56.17 | —O—(CH$_2$)$_2$—C(=N—OC$_2$H$_5$)— |
| 56.18 | —O—CO—CH$_2$—N(CH$_2$C≡CH)— |
| 56.19 | —O—CO—CH(CH$_3$)—N—(CH$_2$C≡CH)— |
| 56.20 | —O—CO—N(i-C$_3$H$_7$)— |
| 56.21 | —O—CO—CH(CH$_3$-N(i-C$_3$H$_7$)— |
| 56.22 | —CH=CH—N—(CH$_2$C≡CH)— |
| 56.23 | —CH=CH—N(iC$_3$H$_7$)— |
| 56.24 | —CH=C(CH$_3$)—N(CH$_2$C≡CH)— |
| 56.25 | —C(CH$_3$)=CH—N(CH$_2$C≡CH)— |
| 56.26 | —S—C(O-iC$_3$H$_7$)=N— |
| 56.27 | —S—C(OCH$_2$C≡CH)=N— |
| 56.28 | —O—CH$_2$—CH$_2$—N(CH$_2$C≡CH)— |
| 56.29 | —O—CH$_2$—CH(CH$_3$)—N(CH$_2$C≡CH)— |
| 56.30 | —O—CH$_2$—CH(CF$_3$)—N(CH$_2$C≡CH)— |
| 56.31 | —S—CH$_2$—CO—N(CH$_3$)— |

TABLE 7

| No. | $R^6$ |
|---|---|
| 6.1 | A—CO—B |
| 6.2 | OR$^9$ |
| 6.3 | C(R$^{10}$)=O |
| 6.4 | C(R$^{10}$)=S |
| 6.5 | C(R$^{10}$)=N—R$^{16}$ |
| 6.6 | C(X$^1$R$^{17}$)(X$^2$R$^{18}$)R$^{10}$ |
| 6.7 | P(R$^{12}$)(R$^{13}$)=O |
| 6.8 | CHR$^{10}$—CHR$^{11}$—CO—B |

TABLE 8

| No. | A | No. | A |
|---|---|---|---|
| A.1 | CH=CH— | A.12 | —CH=C(COCH$_3$)— |
| A.2 | —CH=CH—CH$_2$— | A.13 | —C≡C— |
| A.3 | —CH=CCl— | A.14 | —C≡C—CH$_2$— |
| A.4 | —CH=CBr— | A.15 | —C≡C—CH$_2$—CH$_2$— |
| A.5 | —CH=CI— | A.16 | —C≡C—CH(CH$_3$)— |
| A.6 | —CH=C(CH$_3$)— | A.17 | —C(CH$_3$)=CH— |
| A.7 | —CH=C(C$_2$H$_5$)— | A.18 | —C(CH$_3$)=CCl |
| A.8 | —CH=C(CN)— | A.19 | —C(CH$_3$)=CBr— |
| A.9 | —CH=C(COOCH$_3$)— | A.20 | —C(CH$_3$)=C(CH$_3$)— |
| A.10 | —CH=C(COOC$_2$H$_5$)— | A.21 | —C(CH$_3$)=C(CN)— |
| A.11 | —CH=C(OCOCH$_3$)— | A.22 | —CH=CF— |

TABLE 9

| No. | B |
|---|---|
| B.01 | H |
| B.02 | OH |
| B.03 | OCH$_3$ |
| B.04 | OC$_2$H$_5$ |
| B.05 | O-n-C$_3$H$_7$ |
| B.06 | O-i-C$_3$H$_7$ |
| B.07 | O-n-C$_4$H$_9$ |
| B.08 | O-i-C$_4$H$_9$ |
| B.09 | O-s-C$_4$H$_9$ |
| B.10 | O-tert.-C$_4$H$_9$ |
| B.11 | O-n-C$_5$H$_{11}$ |
| B.12 | O-n-C$_6$H$_{13}$ |
| B.13 | O—CH$_2$CH=CH$_2$ |
| B.14 | O—CH(CH$_3$)CH=CH$_2$ |
| B.15 | O—CH—CH=CH—CH$_2$ |
| B.16 | O—CH$_2$—C≡CH |
| B.17 | O—CH(CH$_3$)—C≡CH |
| B.18 | O—CH$_2$—C≡C—CH$_3$ |
| B.19 | O-cyclopropyl |
| B.20 | O-cyclobutyl |
| B.21 | O-cyclopentyl |
| B.22 | O-cyclohexyl |
| B.23 | O—CH$_2$—CF$_3$ |
| B.24 | O—CH$_2$—CCl$_3$ |
| B.25 | O—(CH$_2$)$_3$—Br |
| B.26 | O-phenyl |
| B.27 | O-(2-F-phenyl) |
| B.28 | O-(2-Cl-phenyl) |
| B.29 | O-(2-Br-phenyl) |
| B.30 | O-(3-F-phenyl) |
| B.31 | O-(3-Cl-phenyl) |
| B.32 | O-(3-Br-phenyl) |
| B.33 | O-(4-F-phenyl) |
| B.34 | O-(4-Cl-phenyl) |
| B.35 | O-(4-Br-phenyl) |
| B.36 | O-(4-OCH$_3$-phenyl) |
| B.37 | O-(4-CN-phenyl) |
| B.38 | O-(4-COOCH$_3$-phenyl) |
| B.39 | O—(CH$_3$-phenyl) |
| B.40 | O-(2,4-Cl$_2$-phenyl) |
| B.41 | O-(2,4-(CH$_3$)$_2$-phenyl) |
| B.42 | O—CH$_2$CN |
| B.43 | O—CH$_2$CH=CCl$_2$ |
| B.44 | O—CH$_2$CH=CHCl |
| B.45 | O—CH$_2$OCH$_3$ |
| B.46 | O—CH$_2$OC$_2$H$_5$ |
| B.47 | O—C$_2$H$_4$OCH$_3$ |
| B.48 | O—C$_2$H$_4$OC$_2$H$_5$ |
| B.49 | O—CH(CH$_3$)—OCH$_3$ |
| B.50 | O—CH(CH$_3$)—OC$_2$H$_5$ |
| B.51 | OCH$_2$C=NOCH$_3$ |
| B.52 | O—C$_2$H$_4$C=NOCH$_3$ |
| B.53 | O—CH$_2$C=NOC$_2$H$_5$ |
| B.54 | O—C(O)CH$_3$ |
| B.55 | O—C(O)C$_2$H$_5$ |
| B.56 | O—C$_2$H$_4$C=NOC$_2$H$_5$ |
| B.57 | SCH$_3$ |
| B.58 | SC$_2$H$_5$ |
| B.59 | S-n-C$_3$H$_7$ |
| B.60 | S-i-C$_3$H$_7$ |
| B.61 | S—CH$_2$CH=CH$_2$ |
| B.62 | S—CH$_2$C≡CH |
| B.63 | S-phenyl |
| B.64 | S—CH$_2$CN |
| B.65 | S—CH$_2$OCH$_3$ |
| B.66 | CH$_3$ |
| B.67 | C$_2$H$_7$ |
| B.68 | n-C$_3$H$_7$ |
| B.69 | i-C$_3$H$_7$ |
| B.70 | n-C$_4$H$_9$ |
| B.71 | i-C$_4$H$_9$ |
| B.72 | s-C$_4$H$_9$ |
| B.73 | tert.-C$_4$H$_9$ |
| B.74 | n-C$_5$H$_{11}$ |
| B.75 | n-C$_6$H$_{13}$ |
| B.76 | CH$_2$CH=CH$_2$ |
| B.77 | CH$_2$C≡CH |
| B.78 | CH(CH$_3$)CH=CH$_2$ |
| B.79 | CH(CH$_3$C≡CH |
| B.80 | CH$_2$Cl |
| B.81 | CH$_2$Br |
| B.82 | CHCl$_2$ |
| B.83 | CF$_3$ |
| B.84 | Cyclopropyl |
| B.85 | Cyclobutyl |
| B.86 | Cyclopentyl |
| B.87 | Cyclohexyl |
| B.88 | Phenyl |
| B.89 | 2-F-phenyl |
| B.90 | 3-F-phenyl |
| B.91 | 4-F-phenyl |
| B.92 | 2-Cl-phenyl |
| B.93 | 4-Cl-phenyl |
| B.94 | 2,4-Cl$_2$-phenyl |
| B.95 | CH$_2$—OCH$_3$ |
| B.96 | CH(OCH$_3$)$_2$ |
| B.97 | CH$_2$—SCH$_3$ |
| B.98 | NH$_2$ |
| B.99 | NHCH$_3$ |
| B.100 | NH-n-C$_3$H$_7$ |
| B.101 | NH-i-C$_3$H$_7$ |
| B.102 | NH-n-C$_4$H$_9$ |
| B.103 | N(CH$_3$)$_2$ |
| B.104 | N(C$_2$H$_5$)$_2$ |
| B.105 | N(CH$_3$)C$_2$H$_5$ |
| B.106 | N(n-C$_3$H$_7$)$_2$ |
| B.107 | NH-CH$_2$CH=CH$_2$ |
| B.108 | NH—CH(CH$_3$)—CH=CH$_2$ |
| B.109 | NH—CH$_2$—C≡CH |
| B.110 | NH—CH(CH$_3$)—C≡CH |
| B.111 | N(CH$_3$)—CH$_2$CH=CH |
| B.112 | N(CH$_3$)—CH$_2$C≡CH |
| B.113 | NH-cyclopropyl |
| B.114 | NH-cyclobutyl |
| B.115 | NH-cyclopentyl |
| B.116 | NH-cyclohexyl |
| B.117 | N(CH$_3$)-cyclohexyl |
| B.118 | N(C$_2$H$_5$)-cyclohexyl |
| B.119 | NH—COCH$_3$ |
| B.120 | NH—COC$_2$H$_5$ |
| B.121 | NH—COOCH$_3$ |
| B.122 | NH—CH$_2$OCH$_3$ |
| B.123 | NH—(CH$_2$)$_2$CCH$_3$ |
| B.124 | N-piperindinyl |
| B.125 | N-pyrrolidinyl |
| B.126 | N-morpholino |
| B.127 | N-Piperazinyl |
| B.128 | NH-phenyl |
| B.129 | NH-(2-CH$_3$-phenyl) |
| B.130 | NH-(2-F-phenyl) |
| B.131 | NH-(4-F-phenyl) |
| B.132 | NH-(2-Cl-phenyl) |
| B.133 | NH-(4-Cl-phenyl) |
| B.134 | NH-(2,4-Cl$_2$-phenyl) |
| B.135 | O—CO—OCH$_3$ |

TABLE 9-continued

| No. | B |
|---|---|
| B.136 | O—CO—OC$_2$H$_5$ |
| B.137 | O—CH$_2$—COOCH$_3$ |
| B.138 | O—CH(CH$_3$)—COOCH$_3$ |

TABLE 10

| No. | R$^9$ |
|---|---|
| 9.01 | CH$_2$CN |
| 9.02 | CH(CH$_3$)—CN |
| 9.03 | (CH$_2$)$_2$—CN |
| 9.04 | (CH$_2$)$_3$—CN |
| 9.05 | (CH$_2$)$_4$—CN |
| 9.06 | CH$_2$OCH$_3$ |
| 9.07 | (CH$_2$)$_2$OCH$_3$ |
| 9.08 | (CH$_2$)$_2$OC$_2$H$_5$ |
| 9.09 | CH$_2$OC$_2$H$_5$ |
| 9.10 | CH$_2$CH$_2$Cl |
| 9.11 | CH$_2$Cl |
| 9.12 | CCl$_3$ |
| 9.13 | CF$_3$ |
| 9.14 | CH$_2$CCl=CH |
| 9.15 | CH$_2$CH=CHCl |
| 9.16 | CH$_2$CH=CCl$_2$ |
| 9.17 | CH$_2$-furan-2-yl |
| 9.18 | CH$_2$-furan-3-yl |
| 9.19 | CH$_2$-thien-2-yl |
| 9.20 | CH$_2$-thien-3-yl |
| 9.21 | CH$_2$-pyrid-2-yl |
| 9.22 | CH$_2$-pyrid-3-yl |
| 9.23 | CH$_2$-pyrid-4-yl |
| 9.24 | CH$_2$-pyrrol-2-yl |
| 9.25 | CH$_2$-pyrrol-3-yl |
| 9.26 | CH$_2$-pyrimidin-2-yl |
| 9.27 | CH$_2$-pyrimidin-4-yl |
| 9.28 | CH$_2$-pyrimidin-5-yl |
| 9.29 | CH$_2$-pyrimidin-6-yl |
| 9.30 | CH$_2$-pyridazin-3-yl |
| 9.31 | CH$_2$-pyridazin-4-yl |
| 9.32 | CH$_2$-tetrahydrofuran-2-yl |
| 9.33 | CH$_2$-tetrahydrofuran-3-yl |
| 9.34 | CH$_2$-(2H)tetrahydropyran-2-yl |
| 9.35 | CH$_2$-(2H)tetrahydropyran-3-yl |
| 9.36 | CH$_2$-(2H)tetrahydropyran-4-yl |
| 9.37 | CH$_2$-pyrrolidin-2-yl |
| 9.38 | CH$_2$-pyrrolidin-3-yl |
| 9.39 | CH$_2$-piperdin-2-yl |
| 9.40 | CH$_2$-piperdin-3-yl |
| 9.41 | CH$_2$-piperdin-4-yl |
| 9.42 | CH$_2$-pyrazin-2-yl |
| 9.43 | CH$_2$-oxazol-2-yl |
| 9.44 | CH$_2$-oxazol-4-yl |
| 9.45 | CH$_2$-oxazol-5-yl |
| 9.46 | CH$_2$-isoxazol-3-yl |
| 9.47 | CH$_2$-isoxazol-4-yl |
| 9.48 | CH$_2$-isoxazol-5-yl |
| 9.49 | CH$_2$-pyrrazol-3-yl |
| 9.50 | CH$_2$-pyrrazol-4-yl |
| 9.51 | CH$_2$-1,2,4-oxadiazol-3-yl |
| 9.52 | CH$_2$-1,2,4-oxadiazol-5-yl |
| 9.53 | CH$_2$-1,3,4-oxadiazol-2-yl |
| 9.54 | CH$_2$-1,3,4-oxadiazol-5-yl |
| 9.55 | CH$_2$-1,2,4-thiadiazol-3-yl |
| 9.56 | CH$_2$-1,2,4-thiadiazol-5-yl |
| 9.57 | CH$_2$-1,3,4-thiadiazol-2-yl |
| 9.58 | CH$_2$-1,3,4-thiadiazol-5-yl |
| 9.59 | CH$_2$-5,6-(2H)-dihydropyran-2-yl |
| 9.60 | CH$_2$-5,6-(2H)-dihydropyran-3-yl |
| 9.61 | CH$_2$-5,6-(2H)-dihydropyran-4-yl |
| 9.62 | CH$_2$-5,6-(2H)-dihydropyran-5-yl |
| 9.63 | CH$_2$-5,6-(2H)-dihydropyran-6-yl |
| 9.64 | CH$_2$-3,4-(2H)-dihydropyran-2-yl |
| 9.65 | CH$_2$-3,4-(2H)-dihydropyran-3-yl |
| 9.66 | CH$_2$-3,4-(2H)-dihydropyran-4-yl |
| 9.67 | CH$_2$-3,4-(2H)-dihydropyran-5-yl |
| 9.68 | CH$_2$-3,4-(2H)-dihydropyran-6-yl |
| 9.69 | CH$_2$-phenyl |
| 9.70 | CH$_2$-(2-Cl-phenyl) |
| 9.71 | CH$_2$-(3-Cl-phenyl) |
| 9.72 | CH$_2$-(4-Cl-phenyl) |
| 9.73 | CH$_2$-(2-F-phenyl) |
| 9.74 | CH$_2$-(3-F-phenyl) |
| 9.75 | CH$_2$-(4-F-phenyl) |
| 9.76 | CH$_2$-(2-CF$_3$-phenyl) |
| 9.77 | CH$_2$-(3-CF$_3$-phenyl) |
| 9.78 | CH$_2$-(4-CF$_3$-phenyl) |
| 9.79 | CH$_2$-(2-CH$_3$-phenyl) |
| 9.80 | CH$_2$-(4-CH$_3$-phenyl) |
| 9.81 | CH(CH$_3$)—COOCH$_3$ |
| 9.82 | CH(CH$_3$)—COOC$_2$H$_5$ |
| 9.83 | CH(CH$_3$)-COO-isopropyl |
| 9.84 | CH$_2$—COO-isopropyl |
| 9.85 | (CH$_2$)$_2$—COOCH$_3$ |
| 9.86 | (CH$_2$)$_2$—COO-isopropyl |
| 9.87 | CH$_2$—COOCH$_2$—OCH$_3$ |
| 9.88 | CH$_2$—COO(CH$_2$)$_2$—OCH$_3$ |
| 9.89 | CH(CH$_3$)—COOCH$_2$—OCH$_3$ |
| 9.90 | CH(CH$_3$)—COO(CH$_2$)$_2$—OCH$_3$ |
| 9.91 | CH$_2$C=N—OCH$_3$ |
| 9.92 | CH$_2$C=N—OC$_2$H$_5$ |
| 9.93 | (CH$_2$)$_2$C=N—OCH$_3$ |
| 9.94 | (CH$_2$)$_2$C=N—OC$_2$H$_5$ |
| 9.95 | CH(CH$_3$)C=N—OCH$_3$ |
| 9.96 | CH(CH$_3$)C=N—OC$_2$H$_5$ |
| 9.97 | CH$_2$—(2H)-tetrahydrothiopyran-2-yl |
| 9.98 | CH$_2$—(2H)-tetrahydrothiopyran-3-yl |
| 9.99 | CH$_2$—(2H)-tetrahydrothiopyran-4-yl |
| 9.100 | 5,6-(2H)-dihydrothiopyran-2-yl |
| 9.101 | 5,6-(2H)-dihydrothiopyran-3-yl |
| 9.102 | 5,6-(2H)-dihydrothiopyran-4-yl |
| 9.103 | 5,6-(2H)-dihydrothiopyran-5-yl |
| 9.104 | 5,6-(2H)-dihydrothiopyran-6-yl |
| 9.105 | 3,4-(2H)-dihydrothiopyran-2-yl |
| 9.106 | 3,4-(2H)-dihydrothiopyran-3-yl |
| 9.107 | 3,4-(2H)-dihydrothiopyran-4-yl |
| 9.108 | 3,4-(2H)-dihydrothiopyran-5-yl |
| 9.109 | 3,4-(2H)-dihydrothiopyran-6-yl |

TABLE 11

| Nr. | R$^{10}$ |
|---|---|
| 10.01 | H |
| 10.02 | CH$_3$ |
| 10.03 | C$_2$H$_5$ |
| 10.04 | n-C$_3$H$_7$ |
| 10.05 | i-C$_3$H$_7$ |
| 10.06 | n-C$_4$H$_9$ |
| 10.07 | i-C$_4$H$_9$ |
| 10.08 | s-C$_4$H$_9$ |
| 10.09 | tert.-C$_4$H$_9$ |
| 10.10 | n-C$_5$H$_{11}$ |
| 10.11 | n-C$_6$H$_{13}$ |
| 10.12 | CH$_2$—CH=CH$_2$ |
| 10.13 | CH$_2$—C≡CH |
| 10.14 | CF$_3$ |
| 10.15 | CCl$_3$ |
| 10.16 | Cyclopropyl |
| 10.17 | Cyclobutyl |
| 10.18 | Cyclopentyl |
| 10.19 | Cyclohexyl |
| 10.20 | CN |
| 10.21 | CO—OCH$_3$ |
| 10.22 | CO—OC$_2$H$_5$ |

TABLE 12

| Nr. | $R^{11}$ |
|---|---|
| 11.01 | F |
| 11.02 | Cl |
| 11.03 | Br |
| 11.04 | I |
| 11.05 | $CF_3$ |
| 11.06 | OH |
| 11.07 | $OCOCH_3$ |
| 11.08 | $OCOC_2H_5$ |

TABLE 13

| No. | $R^{12}$, $R^{13}$ |
|---|---|
| 12.01 | $OCH_3$ |
| 12.02 | $OC_2H_5$ |
| 12.03 | $O\text{-}iC_3H_7$ |
| 12.04 | $O\text{-}nC_3H_7$ |
| 12.05 | $O\text{-}nC_4H_9$ |
| 12.06 | $O\text{-}iC_4H_9$ |
| 12.07 | $O\text{-}sC_4H_9$ |
| 12.08 | $O\text{-}tC_4H_9$ |
| 12.09 | Phenyl |
| 12.10 | 2-Cl-phenyl |
| 12.11 | 3-Cl-phenyl |
| 12.12 | 2-F-phenyl |
| 12.13 | 3-F-phenyl |
| 12.14 | 4-F-phenyl |
| 12.15 | $4\text{-}NO_2$-phenyl |
| 12.16 | $2,4\text{-}Cl_2$-phenyl |
| 12.17 | 2-F,4-CN-phenyl |

TABLE 14

| No. | $R^{16}$ |
|---|---|
| 16.01 | H |
| 16.02 | $CH_3$ |
| 16.03 | $C_2H_5$ |
| 16.04 | $n\text{-}C_3H_7$ |
| 16.05 | $i\text{-}C_3H_7$ |
| 16.06 | $n\text{-}C_4H_9$ |
| 16.07 | $n\text{-}C_5H_{11}$ |
| 16.08 | $n\text{-}C_6H_{13}$ |
| 16.09 | $CH_2CH=CH_2$ |
| 16.10 | $CH(CH_3)\text{—}CH=CH_2$ |
| 16.11 | $CH_2\text{—}CH=CH\text{—}CH_3$ |
| 16.12 | $CH_2\text{—}C\equiv CH$ |
| 16.13 | $CH(CH_3)\text{—}C\equiv CH$ |
| 16.14 | $CH_2\text{—}C\equiv C\text{—}CH_3$ |
| 16.15 | Cyclopropyl |
| 16.16 | Cyclobutyl |
| 16.17 | Cyclopentyl |
| 16.18 | Cyclohexyl |
| 16.19 | Cycloheptyl |
| 16.20 | $(CH_2)_2Cl$ |
| 16.21 | $CH_2Cl$ |
| 16.22 | Phenyl |
| 16.23 | 2-F-phenyl |
| 16.24 | 3-F-phenyl |
| 16.25 | 4-F-phenyl |
| 16.26 | 2-Cl-phenyl |
| 16.27 | 3-Cl-phenyl |
| 16.28 | 4-Cl-phenyl |
| 16.29 | 2-Br-phenyl |
| 16.30 | 3-Br-phenyl |
| 16.31 | 4-Br-phenyl |
| 16.32 | $2\text{-}CH_3$-phenyl |
| 16.33 | $3\text{-}CH_3$-phenyl |
| 16.34 | $4\text{-}CH_3$-phenyl |
| 16.35 | $2\text{-}CF_3$-phenyl |
| 16.36 | $3\text{-}CF_3$-phenyl |
| 16.37 | $4\text{-}CF_3$-phenyl |

TABLE 14-continued

| No. | $R^{16}$ |
|---|---|
| 16.38 | $2\text{-}OCH_3$-phenyl |
| 16.39 | $3\text{-}OCH_3$-phenyl |
| 16.40 | $4\text{-}OCH_3$-phenyl |
| 16.41 | $4\text{-}NO_2$-phenyl |
| 16.42 | 4-CN-phenyl |
| 16.43 | $2,4\text{-}Cl_2$-phenyl |
| 16.44 | $2,4\text{-}(CH_3)_2$-phenyl |
| 16.45 | $CH_2\text{—}OCH_3$ |
| 16.46 | $(CH_2)_2\text{—}OC_2H_5$ |
| 16.47 | OH |
| 16.48 | $OCH_2COOCH_3$ |
| 16.49 | $OCH_2COOC_2H_5$ |
| 16.50 | $OCH_2COOiPr$ |
| 16.51 | $OCH_2COOtBu$ |
| 16.52 | $O\text{—}CH_2CH=CH_2$ |
| 16.53 | $O\text{—}CH(CH_3)CH=CH_2$ |
| 16.54 | $O\text{—}CH_2C\equiv CH$ |
| 16.55 | $O\text{—}CH(CH_3)\text{—}C\equiv CH$ |
| 16.56 | $O\text{—}CH_2\text{—}C\equiv C\text{—}CH_3$ |
| 16.57 | $O\text{—}CH_2\text{—}CH=CH\text{—}CH_3$ |
| 16.58 | O-cyclopentyl |
| 16.59 | O-cyclohexyl |
| 16.60 | O-cyclopent-3-enyl |
| 16.61 | o-cyclohex-3-enyl |
| 16.62 | $O\text{—}(CH_2)_2\text{—}Cl$ |
| 16.63 | $O\text{—}(CH_2)_2\text{—}Cl$ |
| 16.64 | $O\text{—}(CH_2)\text{—}F$ |
| 16.65 | $O\text{—}CH_2\text{—}CF_3$ |
| 16.66 | $O\text{—}(CH_2)_2\text{—}Br$ |
| 16.67 | $O\text{—}CH_2\text{—}CH=CHCl$ |
| 16.68 | $O\text{—}CH_2\text{—}C(Cl)=CH_2$ |
| 16.69 | $O\text{—}CH_2\text{—}C(Br)=CH_2$ |
| 16.70 | $O\text{—}CH_2\text{—}CH=C(Cl)\text{—}CH_3$ |
| 16.71 | $O\text{—}CH_2\text{—}C(Cl)=CCl_2$ |
| 16.72 | $O\text{—}CH_2$-cyclopropyl |
| 16.73 | $O\text{—}CH_2$-cyclobutyl |
| 16.74 | $O\text{—}CH_2$-cyclopentyl |
| 16.75 | $O\text{—}CH_2$-cyclohexyl |
| 16.76 | $O\text{—}CH_2$-cycloheptyl |
| 16.77 | $O\text{—}CO\text{—}CH_3$ |
| 16.78 | $O\text{—}CO\text{—}C_2H_5$ |
| 16.79 | $O\text{—}CH_2\text{—}CN$ |
| 16.80 | $O\text{—}(CH_2)_3\text{—}CN$ |
| 16.81 | $O\text{—}CH_2\text{—}OCH_3$ |
| 16.82 | $O\text{—}CH_2\text{—}OC_2H_5$ |
| 16.83 | $O\text{—}(CH_2)_2\text{—}OCH_3$ |
| 16.84 | $O\text{—}(CH_2)_2\text{—}OC_2H_5$ |
| 16.85 | $O\text{—}(CH_2)_3\text{—}OC_2H_5$ |
| 16.86 | $O\text{—}(CH_2)_2\text{—}CO\text{—}OCH_3$ |
| 16.87 | $O\text{—}(CH_2)_2\text{—}CO\text{—}OC_2H_5$ |
| 16.88 | $O\text{—}C(CH_3)_2\text{—}CO\text{—}OCH_3$ |
| 16.89 | $O\text{—}C(CH_3)_2\text{—}CO\text{—}OC_2H_5$ |
| 16.90 | $O\text{—}(CH_2)_2\text{—}OH$ |
| 16.91 | $O\text{—}CH_2\text{—}SCH_3$ |
| 16.92 | $O\text{—}(CH_2)_2\text{—}N(CH_3)_2$ |
| 16.93 | $O\text{—}(CH_2)_2\text{—}N(C_2H_5)_2$ |
| 16.94 | $O\text{—}CH_2$-phenyl |
| 16.95 | $O\text{—}(CH_2)_2$-phenyl |
| 16.96 | $O\text{—}(CH_2)_3$-phenyl |
| 16.97 | $O\text{—}(CH_2)_4$-phenyl |
| 16.98 | $O\text{—}(CH_2)_4\text{-}(4\text{-}Cl\text{-}phenyl)$ |
| 16.99 | $O\text{—}(CH_2)_4\text{-}(4\text{-}CH_3\text{-}phenyl$ |
| 16.100 | $O\text{—}(CH_2)_4\text{-}(4\text{-}CH_3\text{-}phenyl)$ |
| 16.101 | $O\text{—}(CH_2)_4\text{-}(4\text{-}F\text{-}phenyl)$ |
| 16.102 | $O\text{—}CH_2CH=CH\text{-}phenyl$ |
| 16.103 | $O\text{—}CH_2CH=CH\text{-}(4\text{-}F\text{-}phenyl)$ |
| 16.104 | $O\text{—}CH_2CH=CH\text{-}(4\text{-}Cl\text{-}phenyl)$ |
| 16.105 | $O\text{—}CH_2CH=CH\text{-}(3\text{-}OCH_3\text{-}phenyl)$ |
| 16.106 | $O\text{—}(CH_2)_2\text{—}CH=CH\text{-}(4\text{-}F\text{-}phenyl)$ |
| 16.107 | $O\text{—}(CH_2)_2\text{—}CH=CH\text{-}(4\text{-}Cl\text{-}phenyl)$ |
| 16.108 | $O\text{—}(CH_2)\text{—}CH=CH\text{-}(3,4\text{-}Cl_2\text{-}phenyl)$ |
| 16.109 | $O\text{—}CH_2\text{—}CH=C(CH_3)\text{-}(4\text{-}F\text{-}phenyl)$ |
| 16.110 | $O\text{—}CH_2\text{—}C\equiv C\text{—}CH_2\text{-}phenyl$ |
| 16.111 | $O\text{—}(CH_2)_2\text{—}O\text{-}phenyl$ |
| 16.112 | $O\text{—}(CH_2)_2\text{—}OCH_2\text{-}phenyl$ |
| 16.113 | $O\text{—}(CH_2)_2\text{—}OCH_2\text{-}(4\text{-}F\text{-}phenyl)$ |
| 16.114 | $O\text{—}CH_2CH=CH\text{—}CH_2\text{—}O\text{-}phenyl$ |

TABLE 14-continued

| No. | $R^{16}$ |
|---|---|
| 16.115 | O—CH$_2$—C≡C—CH$_2$—O-phenyl |
| 16.116 | O—CH$_2$—C≡C—CH$_2$—O-(4-F-phenyl) |
| 16.117 | O—(CH$_2$)$_2$—SCH$_2$-phenyl |
| 16.118 | O—(CH$_2$)$_2$—SCH$_2$-(4-Cl-phenyl) |
| 16.119 | O—(CH$_2$)$_2$—N(CH$_3$)-CH$_2$-phenyl |
| 16.120 | NH$_2$ |
| 16.121 | NH—CH$_3$ |
| 16.122 | NH—C$_2$H$_5$ |
| 16.123 | NH-n-C$_3$H$_7$ |
| 16.124 | NH-i-C$_3$H$_7$ |
| 16.125 | NH-n-C$_4$H$_9$ |
| 16.126 | NH-i-C$_4$H$_9$ |
| 16.127 | NH-s-C$_4$H$_9$ |
| 16.128 | NH-tert.-C$_4$H$_9$ |
| 16.129 | NH-cyclopropyl |
| 16.130 | NH-cyclobutyl |
| 16.131 | NH-cyclopentyl |
| 16.132 | NH-cyclohexyl |
| 16.133 | NH-cycloheptyl |
| 16.134 | N(CH$_3$)$_2$ |
| 16.135 | N(C$_2$H$_5$)$_2$ |
| 16.136 | NH—CH$_2$CH=CH$_2$ |
| 16.137 | NH—CH$_2$C≡CH |
| 16.138 | NH—CH$_2$—CF$_3$ |
| 16.139 | NH—CO—CH$_3$ |
| 16.140 | NH—COC$_2$H$_5$ |
| 16.141 | NH—CO—OCH$_3$ |
| 16.142 | NH—CO—OC$_2$H$_5$ |
| 16.143 | NH—COO-tert.-C$_4$H$_9$ |
| 16.144 | N-Pyrrolidinyl |
| 16.145 | N-Piperdinyl |
| 16.146 | N-Morpholino |
| 16.147 | N-Piperazinyl |
| 16.148 | NH-phenyl |
| 16.149 | NH-(4-Cl-phenyl) |
| 16.150 | NH-(4-F-phenyl) |
| 16.151 | NH-(4-OCH$_3$-phenyl) |
| 16.152 | NH-(2,4-Cl$_2$-phenyl) |
| 16.153 | CH$_2$—OCH$_3$ |
| 16.154 | (CH$_2$)$_2$—OCH$_3$ |
| 16.155 | OCH$_3$ |
| 16.156 | O$_2$H$_5$ |
| 16.157 | O-n-C$_3$H$_7$ |
| 16.158 | O-i-C$_3$H$_7$ |
| 16.159 | O-n-C$_4$H$_9$ |
| 16.160 | O-i-C$_4$H$_9$ |
| 16.161 | O-i-C$_4$H$_9$ |
| 16.162 | tert.C$_4$H$_9$ |

TABLE 15

| No. | $R^{14}$, $R^{15}$ |
|---|---|
| 14.01 | CH$_3$ |
| 14.02 | C$_2$H$_5$ |
| 14.03 | n-C$_3$H$_7$ |
| 14.04 | i-C$_3$H$_7$ |
| 14.05 | n-C$_4$H$_9$ |
| 14.06 | i-C$_4$H$_9$ |
| 14.07 | s-C$_4$H$_9$ |
| 14.08 | tert.-C$_4$H$_9$ |
| 14.09 | n-C$_5$H$_{11}$ |
| 14.10 | n-C$_6$H$_{13}$ |
| 14.11 | CH$_2$CH=CH$_2$ |
| 14.12 | CH(CH$_3$)—CH=CH$_2$ |
| 14.13 | CH$_2$C≡CH |
| 14.14 | CH(CH$_3$)C≡CH |
| 14.15 | CH$_2$OCH$_3$ |
| 14.16 | C$_2$H$_5$OCH$_3$ |
| 14.17 | C$_2$H$_5$OC$_2$H$_5$ |

TABLE 16

| No. | $R^{14}$, $R^{15}$ |
|---|---|
| 15.01 | —(CH$_2$)$_2$— |
| 15.02 | —CH(CH$_3$)—CH$_2$— |
| 15.03 | —CH(C$_2$H$_5$)—CH$_2$— |
| 15.04 | —CH(CH$_3$)—CH—(CH$_3$)— |
| 15.05 | —C(CH$_3$)$_2$—CH$_2$— |
| 15.06 | —CH(CH=CH$_2$)—CH$_2$— |
| 15.07 | —CH(CH$_2$Cl)—CH$_2$— |
| 15.08 | —CH(CH$_2$Br)—CH$_2$— |
| 15.09 | —CH(CH$_2$OH)—CH$_2$— |
| 15.10 | —CH(CH$_2$OCH$_3$)—CH$_2$— |
| 15.11 | —CH(CH$_2$OC$_2$H$_5$)—CH$_2$— |
| 15.12 | —CH(CH$_2$OCH$_2$CH=CH$_2$)—CH$_2$— |
| 15.13 | —CH(CH$_2$OCH$_2$C≡CH)—CH$_2$— |
| 15.14 | —CH(COOH)—CH$_2$— |
| 15.15 | —CH(COOCH$_3$)—CH$_2$— |
| 15.16 | —CH(COOC$_2$H$_5$)—CH$_2$— |
| 15.17 | —CH(COO-n-C$_3$H$_7$)—CH$_2$— |
| 15.18 | —CH(COO-i-C$_3$H$_7$)—CH$_2$— |
| 15.19 | —CH(COO-n-C$_4$H$_9$)—CH$_2$— |
| 15.20 | —CH(COO-n-C$_5$H$_{11}$)—CH$_2$— |
| 15.21 | —CH(COO-n-C$_6$H$_{13}$)—CH$_2$— |
| 15.22 | —(CH$_2$)$_3$— |
| 15.23 | —CH(CH$_3$)—(CH$_2$)$_2$— |
| 15.24 | —CH$_2$—CH(CH$_3$)—CH$_2$— |
| 15.25 | —CH(C$_2$H$_5$)—(CH$_2$)$_2$— |
| 15.26 | —CH$_2$—CH(C$_2$H$_5$)—CH$_2$— |
| 15.27 | —CH(CH$_3$)—CH$_2$—CH(CH$_3$)— |
| 15.28 | —CH$_2$—C(CH$_3$)$_2$—CH$_2$— |
| 15.29 | —CH(CH$_2$OH)—(CH$_2$)$_2$— |
| 15.30 | —CH$_2$—CH(CH$_2$OH)—CH$_2$— |
| 15.31 | —CH(CH$_2$OCH$_3$)—(CH$_2$)$_2$— |
| 15.32 | —CH(CH$_2$OCH$_2$CH=CH2)—(CH$_2$)$_2$— |
| 15.33 | —CH(CH$_2$O—CO—CH$_3$)—CH$_2$— |
| 15.34 | —CH(CH$_2$OCH$_2$C≡CH)—(CH$_2$)$_2$— |
| 15.35 | —CH(CH$_2$OC(O)CH$_3$)—(CH$_2$)$_2$— |
| 15.36 | —CH$_2$—CH(CH$_2$OCH$_3$)—CH$_2$— |
| 15.37 | —CH$_2$—CH(CH$_2$OCH$_2$CH=CH$_2$)—CH$_2$— |
| 15.38 | —CH$_2$—CH(CH$_2$OCH$_2$C≡CH)—CH$_2$— |
| 15.39 | —CH2—CH(CH$_2$OC(O)CH$_3$)—CH$_2$— |
| 15.40 | —CH(CH$_2$Cl)—(CH$_2$)$_2$ |
| 15.41 | —CH$_2$—CH(CH$_2$Cl)—CH$_2$— |
| 15.42 | —C(CH$_3$)—(COOCH$_3$)—CH$_2$— |
| 15.43 | —C(CH$_3$)—(COOC$_2$H$_5$)—CH$_2$— |
| 15.44 | —C(CH$_3$)(COC-n-C$_3$H$_7$)—CH$_2$— |
| 15.45 | —C(CH$_3$)(COO-n-C$_4$H$_5$)—CH$_2$— |
| 15.46 | —CH(CH$_2$CN)—CH$_2$— |
| 15.47 | —CH(CH$_2$CN)—CH$_2$)$_2$— |
| 15.48 | —CH$_2$—CH(CH$_2$CN)—CH$_2$— |
| 15.49 | —CH$_2$—O—CH$_2$— |
| 15.50 | —CH$_2$—NH—CH$_2$— |
| 15.51 | —CH$_2$—N(CH$_3$)—CH$_2$— |
| 15.52 | —(CH$_2$)$_4$— |
| 15.53 | —CH$_2$—CH=CH—CH$_2$— |
| 15.54 | —CH$_2$—O—(CH$_2$)$_2$— |
| 15.55 | —CO—CH$_2$— |
| 15.56 | —CO—(CH$_2$)$_2$— |
| 15.57 | —CH$_2$—CO—CH$_2$— |
| 15.58 | —CO—C(CH$_3$)$_2$— |
| 15.59 | —CO—O—CH$_2$— |
| 15.60 | —CH$_2$—S—CH$_2$— |
| 15.61 | —CH(CH$_2$O—CO—CH$_3$)—CH$_2$— |

With regard to the herbicidal use, particularly preferred compounds are shown below in Tables 17–21:

TABLE 17

Cyclohexene-1,2-dicarboxylic acid derivatives having the structure Ib where $R^5$ is Cl

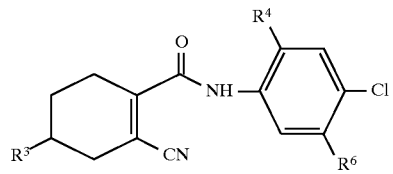

Ib

| No. | $R^3$ | $R^4$ | $R^6$ |
|---|---|---|---|
| Ib.001 | H | H | CH=CH—CN |
| Ib.002 | H | H | CH—CHCl—COOCH$_3$ |
| Ib.003 | H | H | CH—CHCl—COOC$_2$H$_5$ |
| Ib.004 | H | H | CH$_2$—CHBr—COOCH$_3$ |
| Ib.005 | H | H | CH$_2$—CHBr—COOC$_2$H$_5$ |
| Ib.006 | H | H | CH=CH—COOCH$_3$ |
| Ib.007 | H | H | CH=CH—COOC$_2$H$_5$ |
| Ib.008 | H | H | CH=CH—COOi—C$_3$H$_7$ |
| Ib.009 | H | H | CH=CCl—COOCH$_3$ |
| Ib.010 | H | H | CH=CCl—COOC$_2$H$_5$ |
| Ib.011 | H | H | CH=CBr—COOCH$_3$ |
| Ib.012 | H | H | CH=CBr—COOC$_2$H$_5$ |
| Ib.013 | H | H | CH=C(CN)-COOCH$_3$ |
| Ib.014 | H | H | 4-Methyl-1,3-dithiolan-2-yl |
| Ib.015 | H | H | 1,3-Dithiolan-2-yl |
| Ib.016 | H | H | 1,3-Dioxolan-2-yl |
| Ib.017 | H | H | 1,3-Dioxan-2-yl |
| Ib.018 | H | H | 4-Methyl-4-n-Butoxycarbonyl-1,3-dioxolan-2-yl |
| Ib.019 | H | H | O—CH$_2$-3-Tetrahydropyranyl |
| Ib.020 | H | H | O—CH$_2$-2-Tetrahydrofuranyl |
| Ib.021 | H | H | CH=NOCH$_2$C=CH$_2$ |
| Ib.022 | H | H | CH=NOCH$_2$COOCH$_3$ |
| Ib.023 | H | H | CH=NOCH(CH$_3$)-COOCH$_3$ |
| Ib.024 | H | H | CH=C(CH$_3$)-COOCH$_3$ |

Furthermore, the following cyclohexene-1,2-dicarboxylic acid derivatives Ib ($R^5$=Cl) are particularly preferred:

compounds No. Ib.101 to Ib.124, which differ from the corresponding compounds No. Ib.001 to Ib.024 in that $R^4$ in each case is fluorine;

compounds No. Ib.201 to Ib.224, which differ from the corresponding compounds No. Ib.001 to Ib.024 in that $R^3$ in each case is methyl;

compounds No. Ib.301 to Ib.324, which differ from the corresponding compounds No. Ib.001 to Ib.024 in that in each case $R^3$ is methyl and $R^4$ is fluorine.

TABLE 18

Cyclohexene-1,2-dicarboxylic acid derivatives having the structure Ib

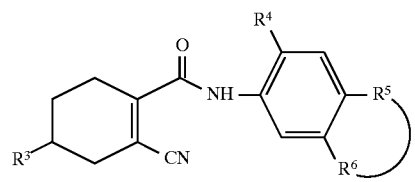

Ib

| No. | $R^3$ | $R^4$ | $-(R^5 + R^6)-$ |
|---|---|---|---|
| Ib.051 | H | H | —O—CH$_2$—CO—N(CH$_3$)- |
| Ib.052 | H | H | —O—CH$_2$—CO—N(CH$_2$—C≡CH)- |
| Ib.053 | H | H | —O—CH$_2$—CO—N(CH$_2$-Tetrahydropyran-3-yl)- |
| Ib.054 | H | H | —S—CH$_2$—CO—N(CH$_3$)- |

TABLE 18-continued

Cyclohexene-1,2-dicarboxylic acid derivatives having the structure Ib

| No. | $R^3$ | $R^4$ | $-(R^5 + R^6)-$ |
|---|---|---|---|
| Ib.055 | H | H | —S—CH$_2$—CO—N(CH$_2$C≡CH)- |
| Ib.056 | H | H | —CH$_2$—CH$_2$—CO—N(CH$_3$)- |
| Ib.057 | H | H | —CH$_2$—CH$_2$—CO—N(CH$_2$C≡CH)- |
| Ib.058 | H | H | —O—CO—N(CH$_3$)- |
| Ib.059 | H | H | —S—CO—N(CH$_3$)- |
| Ib.060 | H | H | —CH$_2$—CO—N(CH$_3$)- |
| Ib.061 | H | H | —O—CO—N(CH$_2$C≡CH)- |
| Ib.062 | H | H | —S—CO—N(CH$_2$C≡CH)- |
| Ib.063 | H | H | —CH$_3$—CO—N(CH$_2$C≡CH)- |

Furthermore, the following cyclohexene-1,2-dicarboxylic acid derivatives Ib are particularly preferred:

compounds No. Ib.151 to Ib.163 which correspond to the abovementioned compounds No. Ib.051 to Ib.063 in which however $R^4$ in each case is fluorine;

compounds No. Ib.251 to Ib.263 which correspond to the abovementioned compounds No. Ib.051 to Ib.063 in which however $R^3$ in each case is methyl;

compounds No. Ib.351 to Ib.363 which correspond to the abovementioned compounds No. Ib.051 to Ib.063 in which however $R^3$ in each case is methyl and $R^4$ is fluorine.

TABLE 19

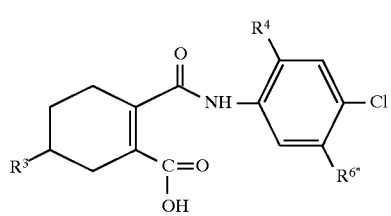

VIIIa {$R^{20}$ = H}

| No. | $R^3$ | $R^4$ | $R^{6"}$ |
|---|---|---|---|
| VIIIa.001 | H | H | CH$_2$—CHCl—COOCH$_3$ |
| VIIIa.002 | H | H | CH$_2$—CHBr—COOCH$_3$ |
| VIIIa.003 | H | H | CH$_2$—CHCl—COOC$_2$H$_5$ |
| VIIIa.004 | H | H | CH$_2$—CHBr—COOC$_2$H$_5$ |
| VIIIa.005 | H | H | CH=CH—COOCH$_3$ |
| VIIIa.006 | H | H | CH=C(CH$_3$)-CCOCH$_3$ |
| VIIIa.007 | H | H | CH=CH—COOC$_2$H$_5$ |
| VIIIa.008 | H | H | CH=C(CH$_3$)-COOC$_2$H$_5$ |
| VIIIa.009 | H | H | CH=CCl—COOCH$_3$ |
| VIIIa.010 | H | H | CH=CCl—COOC$_2$H$_5$ |
| VIIIa.011 | H | H | CH=CBr—COOCH$_3$ |
| VIIIa.012 | H | H | CH=CBr—COOC$_2$H$_5$ |
| VIIIa.013 | H | H | CH=C(CN)-COOCH$_3$ |
| VIIIa.014 | H | H | CH=C(CN)-COOC$_2$H$_5$ |
| VIIIa.015 | H | H | CH=CH—COOH |
| VIIIa.016 | H | H | CH=C(CH$_3$)-COOH |
| VIIIa.017 | H | H | O—CH$_2$—CN |

TABLE 19-continued

VIIIa {R$^{20}$ = H}

| No. | R$^3$ | R$^4$ | R$^{6''}$ |
|---|---|---|---|
| VIIIa.018 | H | H | O—CH$_2$-(1,3-dioxolan-2-yl) |
| VIIIa.019 | H | H | O—C(CH$_3$)-COOCH$_3$ |
| VIIIa.020 | H | H | O—C(CH$_3$)-COOC$_2$H$_5$ |
| VIIIa.021 | H | H | O—CH$_2$-(tetrahydrofuran-2-yl) |
| VIIIa.022 | H | H | O—CH$_2$-(tetrahydrofuran-3-yl) |
| VIIIa.023 | H | H | O—CH$_2$-(tetrahydropyran-2-yl) |
| VIIIa.024 | H | H | O—CH$_2$-(tetrahydropyran-3-yl) |
| VIIIa.025 | H | H | 1,3-dioxolan-3-yl |
| VIIIa.026 | H | H | 1,3-dithiolan-2-yl |
| VIIIa.027 | H | H | 4-methyl-4-butoxycarbonyl-1,3-dioxolan-2-yl |
| VIIIa.028 | H | H | 1,3-dioxan-2-yl |
| VIIIa.029 | H | H | 4-methyl-1,3-dithiolan-2-yl |
| VIIIa.030 | H | H | CH=N—OCH$_2$CH=CH$_2$ |
| VIIIa.031 | H | H | CH=N—OCH$_2$COOCH$_3$ |
| VIIIa.032 | H | H | CH=N—OCH(CH$_3$)-COOCH$_3$ |
| VIIIa.033 | H | H | CH=C(CH$_3$)-CONH(nC$_3$H$_7$) |
| VIIIa.034 | H | H | CH=C(CH$_3$)-CONH(iC$_3$H$_7$) |
| VIIIa.035 | H | H | CH=CCl—COOH |
| VIIIa.036 | H | H | CH=CBr—COOH |

Furthermore, the following tetrahydrophthalamic esters VIIIa (R$^{20}$=H) are particularly preferred:
  compounds No. VIIIa.101 to VIIIa.136, which differ from the corresponding compounds No. VIIIa.001 to VIIIa.036 in that R$^4$ in each case is fluorine;
  compounds No. VIIIa.201 to VIIIa.236, which differ from the corresponding compounds No. VIIIa.001 to VIIIa.036 in that R$^3$ in each case is methyl;
  compounds No. VIIIa.301 to VIIIa.336, which differ from the corresponding compounds No. VIIIa.001 to VIIIa.036 in that in each case R$^3$ is methyl and R$^4$ is fluorine.

TABLE 20

VIIIa {R$^{20}$ = H}

| No. | R$^3$ | R$^4$ | -(R$^5$ + R$^{6''}$)- |
|---|---|---|---|
| VIIIa.051 | H | H | —O—CH$_2$—CO—N(CH$_3$)- |
| VIIIa.052 | H | H | —O—CH$_2$—CO—N(CH$_2$C≡CH)- |
| VIIIa.053 | H | H | —O—CH$_2$—CO—N(CH$_2$-tetrahydropyran-3-yl)- |
| VIIIa.054 | H | H | —S—CH$_2$—CO—N(CH$_3$)- |
| VIIIa.055 | H | H | —S—CH$_2$—CO—N(CH$_2$C≡CH)- |
| VIIIa.056 | H | H | —CH$_2$—CH$_2$—CO—N(CH$_3$)- |
| VIIIa.057 | H | H | —CH$_2$—CH$_2$—CO—N(CH$_2$C≡CH)- |
| VIIIa.058 | H | H | —C—CO—N(CH$_3$)- |
| VIIIa.059 | H | H | —S—CO—N(CH$_3$)- |
| VIIIa.060 | H | H | —CH$_2$—CO—N(CH$_3$)- |

TABLE 20-continued

VIIIa {R$^{20}$ = H}

| No. | R$^3$ | R$^4$ | -(R$^5$ + R$^{6''}$)- |
|---|---|---|---|
| VIIIa.061 | H | H | —O—CO—N(CH$_2$C≡CH)- |
| VIIIa.062 | H | H | —S—CO—N(CH$_2$C≡CH)- |
| VIIIa.063 | H | H | —CH$_3$—CO—N(CH$_2$C≡CH)- |

Furthermore, the following tetrahydrophthalic esters VIIIa (R$^{20}$=H) are particularly preferred:
  compounds No. VIIIa.151 to VIIIa.163, which differ from the corresponding compounds No. VIIIa.051 to VIIIa.063 in that R$^4$ in each case is fluorine;
  compounds No. VIIIa.251 to VIIIa.263, which differ from the corresponding compounds No. VIIIa.051 to VIIIa.063 in that R$^3$ in each case is methyl;
  compounds No. VIIIa.351 to VIIIa.363, which differ from the corresponding compounds No. VIIIa.051 to VIIIa.063 in that in each case R$^3$ is methyl and R$^4$ is fluorine.

TABLE 21

Tetrahydroisophthalimides having the structure IIIa where R$^3$ and R$^4$ are each H IIIa {R$^3$, R$^4$ = H}

| No. | R$^{6'}$ |
|---|---|
| IIIa.001 | CH=CH—CN |
| IIIa.002 | CH—CHCl—COOCH$_3$ |
| IIIa.003 | CH—CHCl—COOC$_2$H$_5$ |
| IIIa.004 | CH$_2$—CHBr—COOCH$_3$ |
| IIIa.005 | CH$_2$—CHBr—COOC$_2$H$_5$ |
| IIIa.006 | CH=CH—COOCH$_3$ |
| IIIa.007 | CH=CH—COOC$_2$H$_5$ |
| IIIa.008 | CH=CH—CCOi—C$_3$H$_7$ |
| IIIa.009 | CH=CCl—COOCH$_3$ |
| IIIa.010 | CH=CCl—COOC$_2$H$_5$ |
| IIIa.011 | CH=CBr—COOCH$_3$ |
| IIIa.012 | CH=CBr—COOC$_2$H$_5$ |
| IIIa.013 | CH=C(CN)—COOCH$_3$ |
| IIIa.014 | 4-methyl-1,3-dithiolan-2-yl |
| IIIa.015 | 1,3-dithiolan-2-yl |
| IIIa.016 | 1,3-dioxolan-2-yl |
| IIIa.017 | 1,3-dioxan-2-yl |
| IIIa.018 | 4-Methyl-4-n-Butoxycarbonyl-1,3-dioxolan-2-yl |
| IIIa.019 | O—CH$_2$-3-tetrahydropyranyl |

TABLE 21-continued

Tetrahydroisophthalimides having the structure IIIa where
R³ and R⁴ are each H

IIIa {R³, R⁴ = H}

| No.      | R⁶'                                          |
|----------|----------------------------------------------|
| IIIa.020 | O—CH₂-2-tetrahydrofuranyl                    |
| IIIa.021 | CH=NOCH₂C=CH₂                                |
| IIIa.022 | CH=NOCH₂COOCH₃                               |
| IIIa.023 | CH=NOCH(CH₃)-COOCH₃                          |
| IIIa.024 | CH=C(CH₃)-COOCH₃                             |

Furthermore, the tetrahydroisophthalimides No. IIIa.001 to III.024 which correspond to compounds No. IIIa.001 to III.024 and in which $R^4$ in each case is fluorine are particularly preferred.

The substituted cyclohexene-1,2-dicarboxylic acid derivatives Ia are obtainable by various methods, preferably by one of the following processes:

a) Ring cleavage of a substituted 3,4,5,6-tetrahydrophthalimide of the formula II or of a 3,4,5,6-tetrahydroisophthalimide of the formula III with an amine, hydroxylamine or hydrazine IV:

As a rule, the reaction is carried out in an inert solvent or diluent, for example in an aliphatic or aromatic hydrocarbon, such as n-hexane, cyclohexane, toluene or o-, m- or p-xylene, in a halohydrocarbon, such as dichloromethane or chlorobenzene, in an aliphatic or cyclic ether, such as diethyl ether, 1,2-dimethoxyethane, tetrahydrofuran or dioxane, in an inert polar, organic solvent, such as dimethylformamide, dimethyl sulfoxide or acetonitrile, in an alcohol, such as methanol, ethanol or diethylene glycol, in acetone, ethyl acetate, methyl ethyl ketone, nitrobenzene or water or in a mixture of the stated solvents.

However, it is also possible to carry out the reaction in the absence of a solvent, in an excess of IV.

Depending on the starting materials used, the presence of a catalytic amount of a catalyst, for example of a Bronstedt acid, such as hydrogen chloride, or of a Lewis acid, such as aluminum trichloride or boron trifluoride, may increase the reaction rate.

The compounds of the formula IV can be used as free amine bases or in the form of their ammonium, hydroxylammonium or hydrazinium salts, salts with anions which are inert under the reaction conditions being suitable. Examples of suitable salts are those of the compounds IV with inorganic mineral acids, such as hydrohalic acids, in particular hydrochloric acid and hydrobromic acid, and sulfuric acid and nitric acid, or with organic acids, such as oxalic acid and acetic acid.

The ratios can usually be varied within wide ranges. In general, however, the amount of IV is from 10 mol % to a 10-fold molar excess, based on II or III. For the maximum possible conversion of II or III, at least equimolar amounts of IV are required. The relatively large excess of IV is present in particular when the compound simultaneously serves as reactant and solvent.

The reaction is usually carried out at from −40° C. to the boiling point of the reaction mixture, preferably from −20° to 40° C.

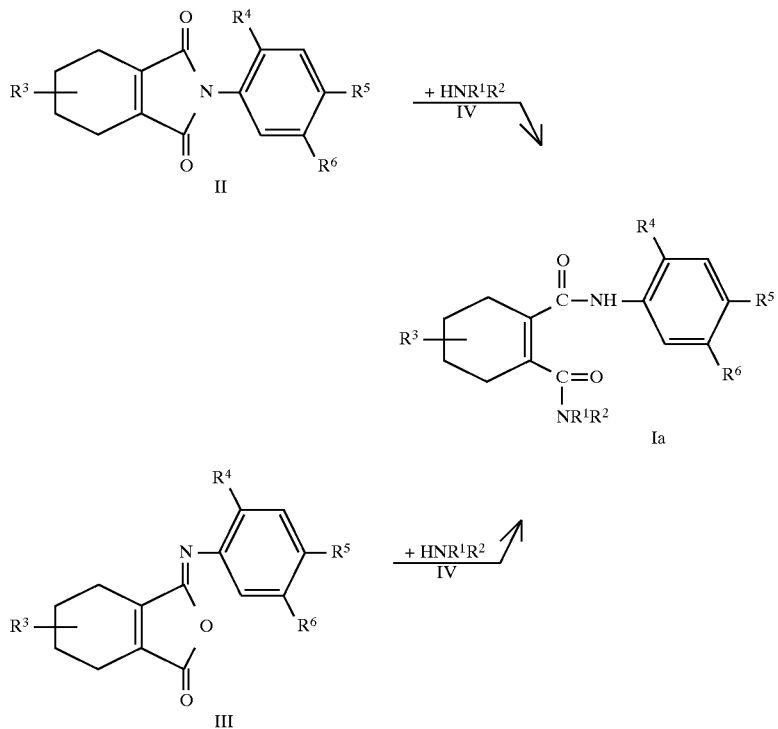

The reaction is not noticeably dependent on the pressure. It is therefore advantageously carried out at atmospheric pressure or under the autogenous pressure of the particular solvent.

b) Reaction of a substituted aniline of the formula V with a tetrahydrophthalimide of the formula VI or with a tetrahydroisophthalimide of the formula VII to give compounds I ($R^1$=hydrogen):

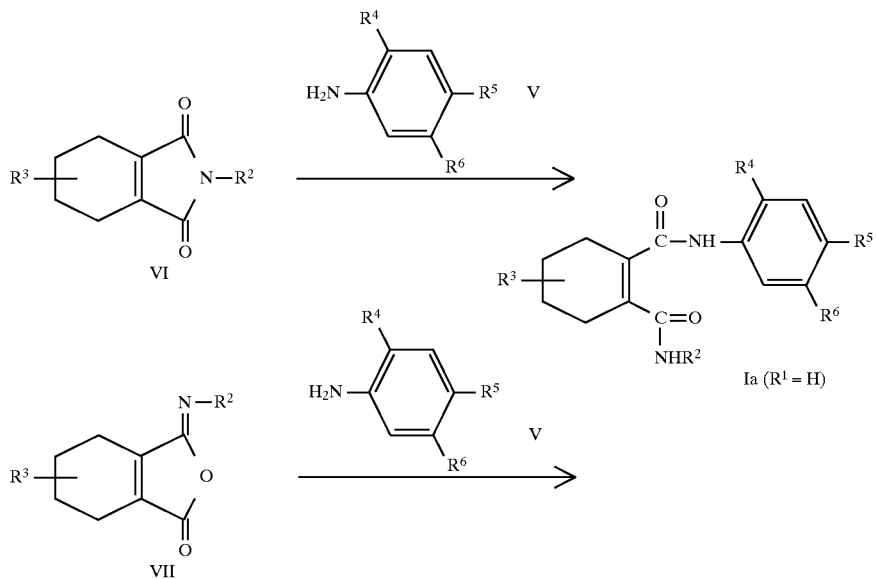

The amines V can be used as free amine bases or in the form of their ammonium salts, salts with anions which are inert under the reaction conditions being suitable. Examples of suitable salts are those of the compounds V with inorganic mineral acids, such as hydrohalic acids, in particular hydrochloric acid and hydrobromic acid, and sulfuric acid and nitric acid, or with organic acids, such as oxalic acid and acetic acid.

The reaction is carried out in an inert solvent or diluent or in an excess of V, and the presence of a catalyst may be advantageous.

Regarding the solvent, the catalyst, the ratios, the temperature and the pressure, the statements made for method (a) are applicable.

c) Condensation of a tetrahdyrophthalamic acid or of a tetrahydrophthalamic ester VIII ($R^{20}$=hydrogen or a hydrocarbon radical) with a primary amine IV ($R^1$=H) in a conventional manner (cf. for example Houben-Weyl, Methoden der Organischen Chemie, Volume E5/2, 1985, pages 941 et seq. and 983 et seq.):

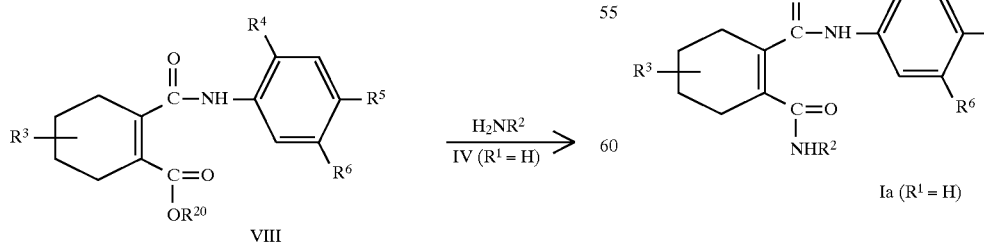

-continued

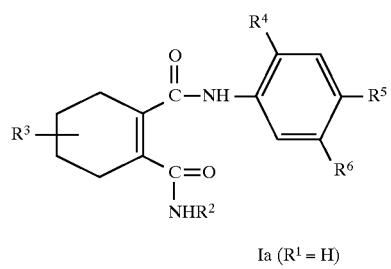

d) Reaction of tetrahydrophthalmic acid derivatives Ia ($R^1$=H) with electrophiles $R^1$—Y in the presence of a base:

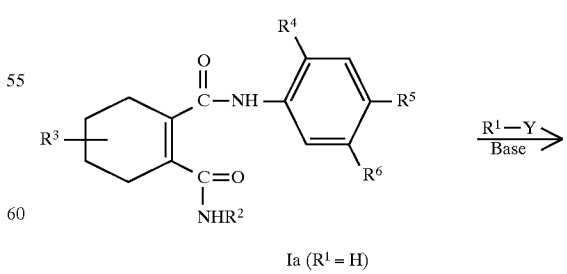

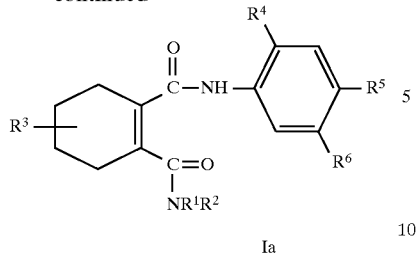

Ia

Y is a reactive substituent which ensures that $R^1$ acts as an electrophile on the nitrogen atom of an amido group. Particularly suitable radicals Y are halogen atoms, such as chlorine or bromine, or alkyl- or haloalkylsulfonyloxy groups.

The reaction is carried out in a conventional manner (cf. for example Houben-Weyl, Methoden der Organischen Chemie, Volume E 5/2, 1985, page 998 et seq.).

In addition to the stated methods of synthesis, it may be advantageous, depending on the particular substituents, to prepare the desired compound I from another substituted cyclohexene-1,2-dicarboxylic acid derivative Ia:

e) Oxidation of substituted cyclohexene-1,2-dicarboxamides I, in which $R^1$ is $C_1–C_4$-alkylthio-$C_1–C_4$-alkyl, to give substituted cyclohexene-1,2-dicarboxamides of the formula I, where $R^1$ is $C_1–C_4$-alkylsulfinyl-$C_1–C_4$-alkyl or Cl-$C_4$-alkylsulfonyl-Cl-$C_4$-alkyl.

The oxidation is carried out in a conventional manner (cf. for example Houben-Weyl, Methoden der Organischen Chemie, Volume 11/1, 4th Edition 1957, page 702 et seq., and Volume 11/2, 4th Edition 1958, page 1094 et seq.), m-chloroperbenzoic acid and hydrogen peroxide being particularly suitable oxidizing agents.

f) Acylation of a substituted cyclohexene-1,2-dicarboxylic acid derivative Ia, where $R^1$ is $C_1–C_4$-hydroxyalkyl, with an acylating agent, such as acetyl chloride, to give a substituted cyclohexene-1,2-dicarboxylic acid derivative Ia, where $R^1$ is $C_1$—$C_4$-alkylcarbonyloxy-$C_1–C_4$-alkyl.

The reaction is carried out in a conventional manner (cf. for example Houben-Weyl, Methoden der Organischen Chemie, Volume E 5/2, 1985, page 1126).

The substituted cyclohexene-1,2-dicarboxylic acid derivatives Ib are likewise obtainable by various methods, preferably by one of the following processes:

g) Dehydration of a substituted cyclohexene-1,2-dicarboxamide of the formula Ia, where $R^1$ and $R^2$ are each H, with a suitable dehydrating agent:

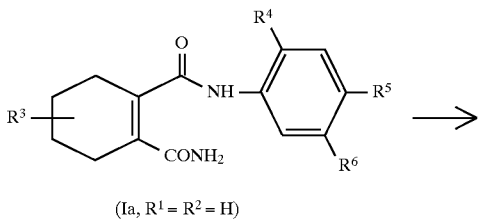

(Ia, $R^1 = R^2 = H$)

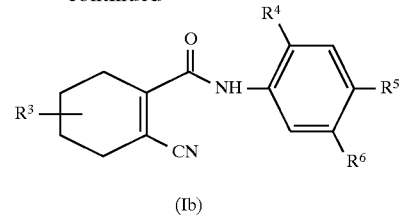

(Ib)

As a rule, the reaction is carried out in an inert solvent or diluent, for example in an aliphatic or aromatic hydrocarbon, such as n-hexane, cyclohexane, toluene or o-, m- or p-xylene, in a halohydrocarbon, such as dichloromethane or chlorobenzene, in an aliphatic or cyclic ether, such as diethyl ether, 1,2-dimethoxyethane, tetrahydrofuran or dioxane, in an inert polar, organic solvent, such as dimethylformamide, dimethyl sulfoxide or acetonitrile, or in an organic nitrogen base, eg. pyridine or triethylamine.

Particularly suitable dehydrating agents are cyanuric chloride, chlorosulfonyl isocyanate, p-toluenesulfonyl chloride pyridine, thionyl chloride or particularly preferably trifluoroacetic anhydride. Other dehydrating agents which are also suitable are described, for example, in Houben-Weyl, Methoden der Organischen Synthese, Vol. E5, page 1356 et seq. and Vol. VIII, page 300 et seq. and in the literature cited there.

The reaction is usually carried out at from −40° to 120° C., preferably from −20° C. to the reflux temperature of the solvent used.

The reaction is not noticeably dependent on the pressure. It is therefore advantageously carried out at atmospheric pressure or under the autogenous pressure of the particular solvent.

h) Reaction of an acyl chloride of the formula IX with an aniline of the formula V

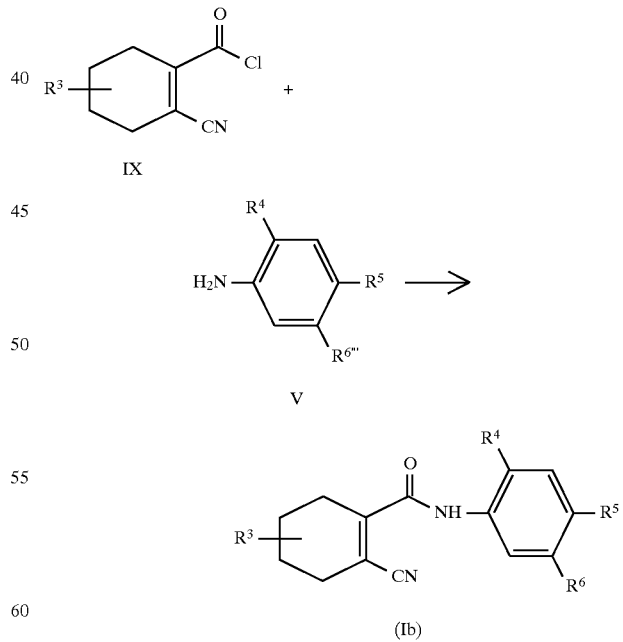

The conditions under which such a reaction is carried out are generally known and are described, for example, in Houben-Weyl, Methoden der organischen Chemie, Vol. VIII, page 655; Vol. XI/2, page 10 et seq.; Vol. E5, 5972 et seq.

Regarding the preparation of the acyl chlorides IX, reference may be made to Tetrahedron 32 (1976), 2379 et seq. and La Chimica e L' Industria 40 (1958), 887–995, and the literature cited there.

i) Reactions at the radicals $R^5$ and $R^6$ in the formulae Ia and Ib

Ester hydrolysis, amidation, esterification, transesterification, etherification, ether cleavage, olefination, reduction, oxidation or halogen or cyano exchange may be mentoined by way of example.

The reaction conditions are generally known and are described in standard chemical works, such as HoubenWeyl, Methoden der Organischen Chemie, or R. C. Larock, Comprehensive Organic Transforamtions, VCH Publishers, New York 1989.

The substituted 3,4,5,6-tetrahydrophthalimides of the formula IIa

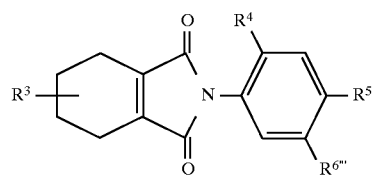

where $R^{6'''}$ is one of the following heterocycles: tetrahydropyran-2-yl, tetrahydropyran-3-yl, tetrahydropyran-4-yl, pyrrol-2-yl, pyrrol-3-yl, thien-3-yl, oxazol4-yl, oxazol-5-yl, thiazol-4-yl, thiazol-5-yl, furan-3-yl, tetrahydrothiopyran-2-yl, tetrahydrothiopyran-3-yl, tetrahydrothiopyran-4-yl, thiazolidin-2-yl,

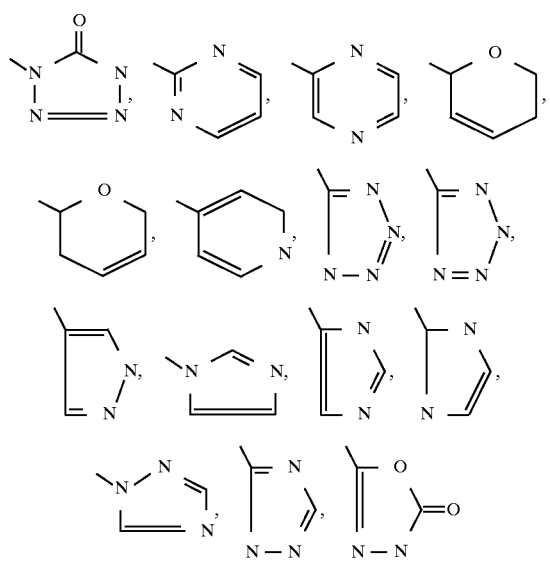

and these heterocycles may carry one of the following substituents on each substitutable ring member: nitro, amino, hydroxy, halogen, cyano, $C_1$–$C_6$-alkyl, $C_2$–$C_6$-alkenyl, $C_2$–$C_6$-alkynyl, $C_1$–$C_6$-haloalkyl, $C_1$–$C_6$-alkoxy-$C_1$–$C_6$-alkyl, $C_1$–$C_6$-alkoxy, $C_1$–$C_6$-haloalkoxy, $C_1$–$C_6$-alkylthio-$C_1$–$C_6$-alkyl, $C_1$–$C_6$-alkoxyalkyl, $C_1$–$C_6$-cyanoalkyl, $C_1$–$C_6$-alkoxycarbonyl and $C_1$–$C_6$-alkoxycarbonyl-$C_1$–$C_6$-alkyl, are novel.

The compounds II are prepared in general by condensation of the compounds XI with tetrahydrophthalic anhydrides XII. The presence of a protic acid, such as p-toluenesulfonic acid or benzenesulfonic acid, may be advantageous here:

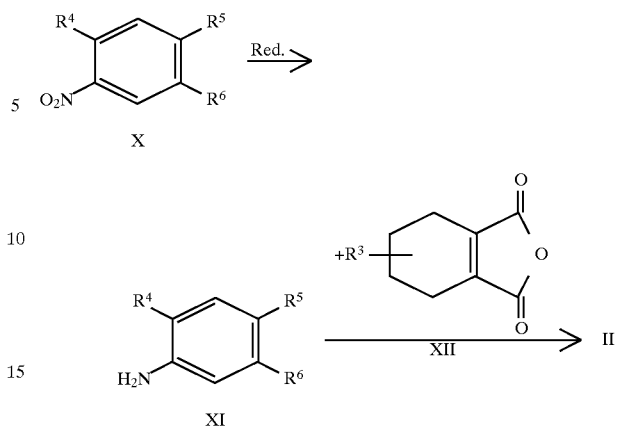

The condensation is advantageously carried out in an inert organic solvent, for example lower alkanoic acid, such as acetic acid, propionic acid and isobutyric acid, alkanoates, such as ethyl acetate, relatively high-boiling hydrocarbons, such as toluene and xylene, amides, such as dimethylformamide, or mixtures of the stated solvents being suitable.

When an aprotic solvent is used, it is advisable to remove the resulting water of reaction continuously.

For the maximum possible conversion, at least equimolar amounts of XI or XII are required. A small excess of one of the two components, up to about 10 mol %, is preferably used.

The reaction temperature is preferably from 0° C. to the boiling point of the particular reaction mixture, in particular from 20° to 140° C.

The reaction is usually carried out at atmospheric pressure or under the autogenous pressure of the particular solvent. Higher or lower pressure is possible but generally has no advantage.

The aniline derivatives XI are in turn obtainable from compounds X by conventional reduction (cf. for example Houben-Weyl, Methoden der Organischen Chemie, Volume XI/1, 4th Edition 1957, page 341 et seq.).

Examples of suitable reducing agents are elemental metals, such as iron, hydrogen in the presence of a suitable catalyst, preferably commercial noble metal catalysts, such as platinum on active carbon and Raney nickel, or complex metal hydrides, eg. sodium borohydride, in the presence of a suitable catalyst, preferably of a commercial noble metal catalyst (cf. for example T. Neilson et al., J. Chem. Soc. (1962), 371 and the literature cited there.

The reduced products XI can also be subjected to the condensation with XII without isolation.

Further intermediates II required for the synthesis of the compounds Ia are either known or can be prepared by methods known per se. For example, reference may be made to the following publications:

DE-A 36 03 789, DE-A 36 07 300, DE-A 37 41 237, EP-A 049 508, EP-A 083 055, EP-A 170 191, EP-A 177 032, EP-A 188 259, EP-A 207 894, EP-A 211 805, EP-A 218 972, EP-A 263 299, EP-A 271 170, EP-A 275 131, EP-A 288 960, EP-A 290 863, EP-A 296 416, EP-A 300 307, EP-A 300 387, EP-A 300 398, EP-A 313 963, EP-A 398 115, EP-A 400 427, U.S. Pat. No. 4,332,944,

U.S. Pat. No. 4,816,065, JO 57/056 403, JO 59/082 360, JO 59/095 203, JO 59/155 358, JO 59/181 256, JO 60/152 465, JO 60/246 367, JO 61/027 962, JO 61/165 383, JO 61/174 970, JO 61/280 471, JO 62/114 961, JO 63/267 779, Jo 63/275 580, JO 01/034 892, JO 01/047 784 and JO 01/066 182.

The present invention furthermore relates to novel substituted 3,4,5,6-tetrahydrophthalimides of the general formula IIb

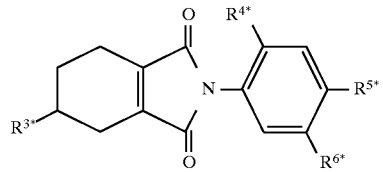

where $R^{3*}$ is hydrogen or methyl, $R^{4*}$ is hydrogen or fluorine, $R^{5*}$ is chlorine, $R^{6*}$ is —$CH_2$—$CHR^{22}CO_2R^{23}{}_1$, $R^{22}$ is chlorine or bromine and $R^{23}$ is methyl or ethyl.

It is known that substituted 3,4,5,6-tetrahydrophthalimides can be used as herbicides (cf. DE-A 36 03 789, EP-A 300 398) or as desiccants and defoliants (cf. DE-A 39 05 916). However, their action is unsatisfactory.

Accordingly, the 3,4,5,6-tetrahydrophthalimides defined above and of the general formula IIb have been found.

Herbicides and defoliants or desiccants which contain these substances IIb have also been found.

The substituted 3,4,5,6-tetrahydrophthalimides of the formula IIb may be present in the form of their environmentally compatible salts, suitable salts being in general the salts of bases which do not adversely affect the herbicidal action of IIb.

Particularly suitable basic salts are those of the alkali metals, preferably sodium salts and potassium salts, those of the alkaline earth metals, preferably calcium salts and magnesium salts, and those of the transition metals, preferably zinc salts and iron salts, and the ammonium salts which may carry from one to three $C_1$–$C_4$-alkyl or hydroxy-$C_1$–$C_4$-alkyl substituents and/or one phenyl or benzyl substituent, preferably diisopropylammonium, tetramethylammonium, tetrabutylammonium, trimethylbenzylammonium and trimethyl-(2-hydroxyethyl)ammonium salts and the phosphonium, sulfonium and sulfoxonium salts.

The compounds of the formula IIb may contain a center of chirality and are then in the form of enantiomer mixtures. The invention relates both to the pure enantiomers and to the mixtures thereof.

With regard to the use of the novel substituted 3,4,5,6-tetrahydrophthalimides of the formula IIb as herbicidal compounds and/or compounds having a defoliant/desiccant action, particularly preferred compounds are shown in Table 22 below:

TABLE 22

| $R^{3*}$ | $R^{4*}$ | $R^{5*}$ | $R^{22}$ | $R^{23}$ |
|---|---|---|---|---|
| H | H | Cl | Cl | $CH_3$ |
| H | F | Cl | Cl | $CH_3$ |
| $CH_3$ | H | Cl | Cl | $CH_3$ |
| $CH_3$ | F | Cl | Cl | $CH_3$ |
| H | H | Cl | Br | $CH_3$ |
| H | F | Cl | Br | $CH_3$ |
| $CH_3$ | H | Cl | Br | $CH_3$ |
| $CH_3$ | F | Cl | Br | $CH_3$ |
| H | H | Cl | Cl | $C_2H_5$ |
| H | F | Cl | Cl | $C_2H_5$ |
| $CH_3$ | H | Cl | Cl | $C_2H_5$ |
| $CH_3$ | F | Cl | Cl | $C_2H_5$ |
| H | H | Cl | Br | $C_2H_5$ |
| H | F | Cl | Br | $C_2H_5$ |
| $CH_3$ | H | Cl | Br | $C_2H_5$ |
| $CH_3$ | F | Cl | Br | $C_2H_5$ |

The compounds of the formula IIb are obtainable in various ways similarly to known reaction methods. Some processes are described below by way of example:

Process A

Compounds of the formula IIb are obtained in a conventional manner (H. P. Doyle, Siegfried, P. C. Elliott and J. F. Dellariar, J. Org. Chem. 42 (1977), 2431) by subjecting a compound of the formula XIII and a compound of the formula XIV to a Meerwein arylation reaction or a conventional modification thereof.

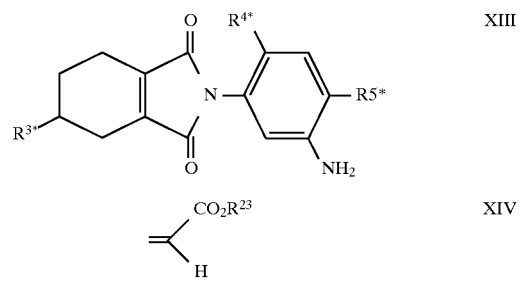

In this type of reaction, the amino compound is converted into a diazonium salt. The latter reacts with an olefin in the presence of a copper salt.

Advantageously, the phenyldiazonium salt is obtained in a conventional manner in aqueous acidic solution, for example in hydrochloric acid, hydrobromic acid or sulfuric acid, by reacting an amino compound of the formula XIII with a nitrite, eg. sodium nitrite, potassium nitrite, etc. The unsaturated component XIV in a suitable solvent, such as $H_2O$, acetone, diethyl ketone, methyl ethyl ketone, acetonitrile, dioxane, tetrahydrofuran, methanol, ethanol, etc., in the presence of a copper halide, eg. CuCl, CuBr, $CuCl_2$ or $CuBr_2$, is then added. The reactions can be carried out at from −30° to +50° C. The components of the diazotization reaction are usually used in a stoichiometric ratio, but an excess of one or other component may be advantageous.

As a rule, compounds of the formula XIV are used in a large excess, but it may also be advantageous to use them in a small excess, in a stoichiometric amount or in less than the stoichiometric amount.

The copper halide is generally used in a stoichiometric ratio, but an excess or less than the stoichiometric amount may be advantageous.

Alternatively, the phenyldiazonium salt may be obtained in a conventional manner in anhydrous systems, for example hydrochloric acid-containing glacial acid acetic, dioxane, absolute alcohol, tetrahydrofuran, acetonitrile or acetone, with a nitrite, eg. tert-butyl nitrite, isopentyl nitrite, etc. The diazotization may take place in the presence of the olefin component XIV and of the copper halide or prior to the addition of the two last-mentioned components.

Process B

Compounds of the formula IIb are obtained in a conventional manner by hydrogenation of compounds of the formula XV

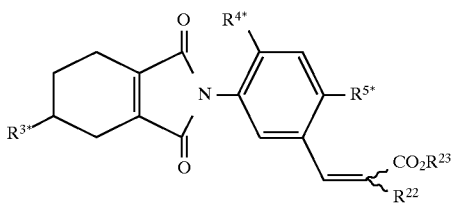

Examples of suitable reducing agents are elemental metals, eg. iron, tin, zinc, etc., hydrogen in the presence of suitable catalysts, eg. Pd/C, Pt/C, Raney Ni, etc., complex metal hydrides, eg. $LiAlH_4$, $NaBH_4$, etc., in the presence or absence of catalysts.

The solvents usually used are acids, eg. acetic acid, propionic acid, etc., alcohols, eg. methanol, ethanol, etc., ethers, eg. diethyl ether, methyl tertbutyl ether, tetrahydrofuran, dioxane, etc., aromatics, eg. benzene, toluene, etc., or corresponding mixtures, said solvents being matched with the reducing agents.

The reactions can be carried out at from $-100°$ C. to the reflux temperature of the particular solvent or solvent mixture.

Usually, the starting materials are used in a stoichiometric ratio, but in specific cases an excess of one or other component may be advantageous.

Process C

Compounds of the formula IIb are obtained by processes known from the literature or similar to processes known from the literature, from compounds of the formula $IIb^+$ by exchanging $R^{22+}$ for another halide, the starting materials being obtained by processes A, B and D.

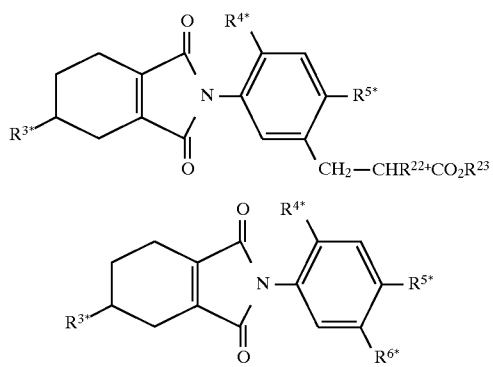

A suitable radical $R^{22+}$ is chlorine or bromine and a suitable radical $R^{22}$ is bromine or chlorine, nickel catalysts being used, in correspondingly matched aprotic solvents or solvent mixtures, such as acetone, diethyl ketone, methyl ethyl ketone, dimethylformamide, diethylformamide, N-methylpyrrolidone, dimethyl sulfoxide, sulfolane or chlorohydrocarbons, such as methylene chloride, chloroform, etc.

The reactions are usually carried out at from $-30°$ C. to the reflux temperature of the particular solvent or solvent mixture.

As a rule, the starting materials are used in a stoichiometric ratio, but an excess or less than the stoichiometric amount of one or other component may be advantageous.

Process D

Compounds of the formula IIb are obtained in a conventional manner by condensation of an anhydride of the formula XII and an aniline of the formula XVI

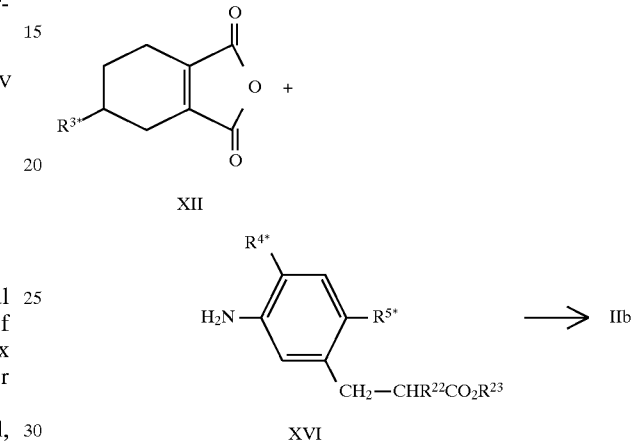

in an inert organic solvent. Alkanecarboxylic acids, eg. acetic acid, propionic acid or isobutyric acid, alkanecarboxylates, eg. ethyl acetate, aprotic solvents, eg. dimethylformamide, dimethyl sulfoxide, N-methylpyrrolidone, etc., aromatics, eg. toluene, xylene, etc. are suitable for this purpose. When an aprotic solvent is used, continuous removal of the resulting water of reaction or acid catalysis, for example by means of p-toluenesulfonic acid, trifluoromethanesulfonic acid, etc. is advisable.

The reactions are usually carried out at from $0°$ C. to the reflux temperature of the solvent or solvent mixture.

As a rule, the starting materials are used in a stoichiometric ratio. However, an excess or less than the stoichiometric amount of one or other component may be advantageous.

Process E

Compounds of the formula XVI are obtained in a conventional manner (Houben-Weyl, Vol. XI/1, page 341 et seq. (4th Edition)) by reducing the corresponding nitro compound XVII.

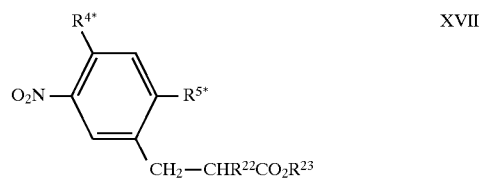

Examples of suitable reducing agents are elemental metals, eg. iron, tin, zinc, etc., hydrogen in the presence of suitable catalysts, eg. Pd/C, Pt/C, Raney Ni, etc., complex metal hydrides, eg. $LiAlH_4$, $NaBH_4$, etc., in the presence or absence of catalysts.

The solvents usually used are acids, eg. acetic acid, propionic acid, etc., alcohols, eg. methanol, ethanol, etc., ethers, eg. diethyl ether, methyl tertbutyl ether, tetrahydrofuran, dioxane, etc., aromatics, eg. benzene, toluene, etc., or corresponding mixtures, said solvents being matched with the reducing agent.

The reactions can be carried out at from −100° C. to the reflux temperature of the particular solvent or solvent mixture.

The starting materials are usually used in a stoichiometric ratio, but in specific cases an excess of one or other component may be advantageous.

Process F

Compounds of the formula XVII are obtained in a conventional manner (M. P. Doyle, B. Siegfried, R. C. Elliot and J. F. Dellaria, J. Org. Chem. 42 (1977), 2431) by subjecting an aniline of the formula XVIII and a compound of the formula XIV to a Meerwein arylation reaction or modifications thereof.

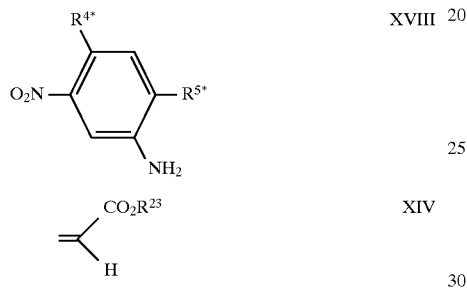

In this type of reaction, the amino compound is converted into a diazonium salt. The latter reacts with an olefin in the presence of a copper salt.

Advantageously, the phenyldiazonium salt is obtained in a conventional manner in aqueous acid solution, for example in hydrochloric acid, hydrobromic acid or sulfuric acid, by reacting an amino compound of the formula XVIII with a nitrite, eg. sodium nitrite, potassium nitrite, etc. The unsaturated component XIV in a suitable solvent, eg. $H_2O$, acetone, diethyl ketone, methyl ethyl ketone, acetonitrile, dioxane, tetrahydrofuran, methanol, ethanol, etc., in the presence of a copper halide, eg. CuCl, CuBr, $CuCl_2$ or $CuBr_2$, is then added. The reactions can be carried out at from −30° to +500° C. The components of the diazotization reaction are usually used in a stoichiometric ratio, but an excess of one or other component may be advantageous.

As a rule, compounds of the formula XIV are used in a large excess, but it may also be advantageous to employ them in a small excess, in a stoichiometric amount or less than the stoichiometric amount.

The copper halide is used, as a rule, in the stoichiometric ratio, but an excess or less than the stoichiometric amount may be advantageous.

Alternatively, the phenyldiazonium salt can be obtained in a conventional manner in anhydrous systems, for example hydrogen chloride-containing glacial acetic acid, dioxane, absolute alcohol, tetrahydrofuran, acetonitrile or acetone, with a nitrite, eg. tert-butyl nitrite, isopentyl nitrite, etc. The diazotization may take place in the presence of the olefin component XIV and of the copper halide or before the addition of two last-mentioned components.

Among the 3,4,5,6-tetrahydroisophthalimides III, novel ones are those of the formula IIIa

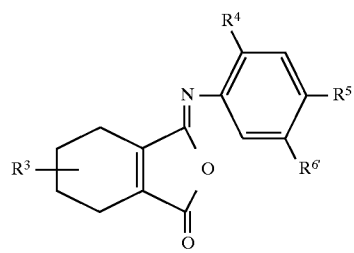

where $R^3$ is hydrogen or $C_1$–$C_6$-alkyl, $R^4$ is hydrogen or halogen, $R^5$ is hydrogen, halogen, nitro, cyano or trifluoromethyl, $R^6$ is a saturated or partially or completely unsaturated 3-membered to 8-membered heterocyclic group which may carry from one to four hetero atoms selected from the group consisting of from one to four nitrogen atoms, one or two oxygen atoms and one or two sulfur atoms, it being possible for one or two methylene groups of the heterocyclic group to be replaced by carbonyl and for the heterocyclic structure to carry one of the following groups on each substitutable carbon atom:

$C_1$–$C_6$-alkyl, $C_2$–$C_6$-alkenyl, $C_2$–$C_6$-alkynyl, $C_1$–$C_6$-alkoxy, $C_1$–$C_6$-alkylthio, $C_3$–$C_6$-alkenyloxy, $C_3$–$C_6$-alkynyloxy, $C_3$–$C_6$-alkenylthio, $C_3$–$C_6$-alkynylthio, $C_1$–$C_6$-alkoxycarbonyl, nitro, amino, halogen, Cl-$C_4$-alkylamino, di-Cl-$C_4$-alkylamino, cyano, $C_1$–$C_6$-cyanoalkyl, $C_1$–$C_6$-haloalkyl or $C_1$–$C_6$-haloalkoxy, or one of the following groups:

—A—CN or —A—CO—B, —$OR^{9'}$, —$C(R^{10})$=O, —$C(R^{10})$=S, —$C(R^{10})$=N—$R^{16}$, —$CHR^{10}$—$CHR^{11}$—CO—B, —$C(X^1R^{14})(X^2R^{15})$ $R^{10}$, —$P(R^{12})(R^{13})$=O, where A is a straight-chain $C_2$–$C_4$-alkenylene or $C_2$–$C_4$-alkynyl chain, both of which may be unsubstituted or may carry one or two radicals selected from the group consisting of halogen, cyano, $C_1$–$C_6$-alkyl, $C_1$–$C_1$–haloalkyl, hydroxy, $C_1$–$C_6$-alkoxy, $C_1$–$C_6$-alkylcarbonyloxy, $C_1$–$C_6$-alkoxycarbonyl and $C_1$–$C_6$-alkylcarbonyl, B is hydrogen, $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, —$OR^{17}$ or —$SR^{17}$, where $R^{17}$ is hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, phenyl which may be unsubstituted or may carry from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, $C_1$–$C_6$-cyanoalkylk, $C_3$–$C_6$-haloalkenyl, $C_1$–$C_6$-alkoxycarbonyl, $C_1$–$C_6$-alkoxy-$C_1$–$C_6$-alkyl, $C_1$–$C_6$-alkoxycarbonyl-$C_1$–$C_6$-alkyl or $C_1$–$C_6$-alkoximino-$C_1$–$C_6$-alkyl, phenyl which may be unsubstituted or may carry from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, $C_1$–$C_6$-alkoxy-$C_1$–$C_6$-alkyl, di-$C_1$–$C_6$-alkoxy-$C_1$–$C_6$-alkyl, $C_1$–$C_6$-alkylthio-$C_1$–$C_6$-alkyl or —$NR^{18}BR^{19}$, where $R^{18}$ and $R^{19}$, independently of one another, are each hydrogen, $C_1$–$C_6$-alkyl, $C_3$–$C_6$- alkenyl, $C_3$–$C_6$-alkynyl, $C_3$–$C_6$-cycloalkyl, $C_1$–$C_6$-haloalkyl, $C_1$–$C_6$-alkyl-carbonyl, $C_1$–$C_6$-alkoxycarbonyl, $C_1$–$C_1$-alkoxy-$C_1$–$C_6$-alkyl or phenyl which may be unsubstituted or may carry from one to three radicals selected from the group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl, or where $R^{18}$ and $R^{19}$, together with the common nitrogen atom, form a saturated or partially or completely unsaturated 4-membered to 7-membered ring which may also contain a further nitrogen atom or an oxygen or sulfur atom as a secondary member, $R^{19'}$ is $C_1$–$C_6$-cyanoalkyl, $C_1$–$C_6$-alkoxy-$C_1$–$C_6$-alkyl, $C_1$–$C_6$-haloalky, $C_3$–$C_6$-haloalkenyl or $C_3$–$C_6$-haloalkynyl, phenyl, phenyl-$C_1$–$C_6$-alkyl, 3-membered to 8-membered heterocyclyl or heterocyclyl-$C_1$–$C_6$-alkyl, where the heterocyclic structures may be saturated or partially or completely unsaturated and may carry from one to four hetero atoms selected from the group consisting of from one to four nitrogen atoms, one or two oxygen atoms and one or two sulfur atoms, and where the phenyl and heterocyclic radicals in turn may carry one of the following substituents on each substitutable carbon atom: $C_1$–$C_6$-alkyl, $C_2$–$C_6$-alkenyl, halogen, cyano, nitro, $C_1$–$C_6$-haloalkyl, $C_1$–$C_6$-alkoxy or $C_1$–$C_6$-alkoxycarbonyl, $C_1$–$C_6$-alkoxy-$C_1$–$C_6$-alkoxycarbonyl-$C_1$–$C_6$-alkyl or $C_1$–$C_6$-alkoximino-$C_1$–$C_6$-alkyl, $R^{10}$ is hydrogen or cyano, $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, $C_1$–$C_6$-alkoxycarbonyl or $C_1$–$C_6$-alkoxycarbonyl-$C_1$–$C_4$-alkyl or phenyl which may be unsubstituted or may carry from one to three radicals selected from the group consisting of halogen, nitro, cyano, $C_1$–$C_6$-alkyl, $C_2$–$C_6$-alkenyl, $C_1$–$C_6$-haloalkyl, $C_1$–$C_6$-alkoxy and $C_1$–$C_6$-alkoxycarbonyl, $R^{11}$ is halogen, trifluoromethyl, hydroxyl, $C_1$–$C_6$-alkoxy or $C_1$–$C_6$-alkylcarbonyloxy, $R^{12}$ and $R^{13}$ are each $C_1$–$C_6$-alkoxy or phenyl which may be unsubstituted or may carry from one to three radicals selected from the group consisting of $C_1$–$C_6$-alkyl, $C_1$–$C_6$-haloalkyl, $C_3$–$C_6$-alkenyl, halogen, cyano, nitro, $C_1$–$C_6$-alkoxy and $C_1$–$C_6$-alkoxycarbonyl, $X^1$ and $X^2$ are each oxygen or sulfur, $R^{14}$ and $R^{15}$ are each $C_1$–$C_6$-alkyl, $C_3$–$C_6$-alkenyl, $C_3$–$C_6$-alkynyl or $C_1$–$C_6$-alkoxy-$C_1$–$C_6$-alkyl or $R^{14}$ and $R^{15}$ together form a two-membered to four-membered carbon chain which may be unsaturated and, if desired, may contain a carbonyl group as a ring member, it being possible for the carbon chain to be unsubstituted or to carry from one to three radicals selected from the group consisting of $C_1$–$C_6$-alkyl, $C_2$–$C_6$-alkenyl, halogen, cyano, nitro, amino, $C_1$–$C_6$-alkoxy, $C_3$–$C_6$-alkenyloxy, $C_3$–$C_6$-alkynyloxy, carboxyl, $C_1$–$C_6$-alkoxycarbonyl, $C_1$–$C_6$-haloalkyl, $C_1$–$C_6$-alkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-hydroxyalkyl, $C_1$–$C_6$-thioalkyl, $C_1$–$C_6$-alkylthio-$C_1$–$C_6$-alkyl and $C_1$–$C_6$-cyanoalkyl, $R^{16}$ is hydrogen, $C_1$–$C_6$-alkyl, $C_3$–$C_6$-alkenyl, $C_3$–$C_6$-alkynyl, $C_3$–$C_6$-cycloalkyl, $C_3$–$C_6$-haloalkyl, phenyl which may be unsubstituted or may carry from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, $C_1$–$C_6$-alkoxy-$C_1$–$C_6$-alkyl, hydroxyl, $C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, $C_3$–$C_7$-cycloalkyl-$C_1$–$C_6$-alkoxy, $C_1$–$C_6$-alkylcarbonyloxy, $C_1$–$C_6$-cyanoalkoxy, $C_1$–$C_6$-alkoxy-$C_1$–$C_6$-alkoxy, $C_1$–$C_6$-alkoxycarbonyl-$C_1$–$C_6$-alkoxy, hydroxy-$C_1$–$C_6$-alkoxy, $C_1$–$C_6$-alkylthio-$C_1$–$C_6$-alkoxy, $C_1$–$C_6$-alkylamino-$C_3$–$C_6$-alkoxy, di($C_1$–$C_6$-alkyl)amino-$C_1$–$C_6$-alkoxy, phenyl-$C_1$–$C_6$-alkoxy, phenyl-$C_3$–$C_6$-alkenyloxy or phenyl-$C_2$–$C_6$-alkynyloxy, where in each case one or two methylene groups of the alkoxy, alkenyloxy and alkynyloxy chains may be replaced by oxygen, sulfur and/or a $C_1$–$C_6$-alkylamino chain, and where the phenyl ring in each case may be unsubstituted or may carry from one to three substituents selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl, —$NR^{16}R^{19}$, or $R^5$ and $R^{6'}$ together form a saturated or partially or completely unsaturated three-membered to five-membered carbon chain which, if desired, may contain one or two oxygen, sulfur or nitrogen atoms and/or one carbonyl or $C_1$–$C_6$-alkoximino group as a ring member, it being possible for the chain to be unsubstituted or in turn to carry one or two radicals selected from the group consisting of cyano, nitro, amino, halogen, $C_1$–$C_6$-alkyl, $C_1$–$C_6$-haloalkyl, $C_2$–$C_6$-alkenyl, $C_2$–$C_6$-alkynyl, $C_1$–$C_6$-cyanoalkyl, $C_1$–$C_6$-alkoxycarbonyl-$C_1$–$C_6$-alkyl, phenyl-$C_1$–$C_6$-alkyl and 3-membered to 8-membered heterocyclyl-$C_1$–$C_6$-alkyl, where the heterocyclic structure may be saturated or partially or completely unsaturated and may carry from one to four hetero atoms selected from the group consisting of from one to four nitrogen atoms, one or two oxygen atoms and one or two sulfur atoms, with the exception of those compounds at which $R^5$ and $R^{6'}$ together form one of the following chains:
a substituted di- or trimethyleneoxy group bonded to the bonding site $R^{6'}$ via the oxygen
a substituted di- or trimethylenecarbonyl group bonded to the bonding site $R^{6'}$ via the carbonyl group or
a substituted di- or trimethyleneoximino group bonded to the bonding site $R^{6'}$ via the oximino group.

Regarding the known 3,4,5,6-tetrahydroisophthalimides III, refer in particular to DE-A 27 33 115, EP-A 271 170, EP-A 275 131, EP-A 073 409, JO 59/070 682 and JO 59/204 181.

The 3,4,5,6-tetrahydroisophthalimides of the formula III are advantageously obtained by intramolecular condensation from compounds VIII:

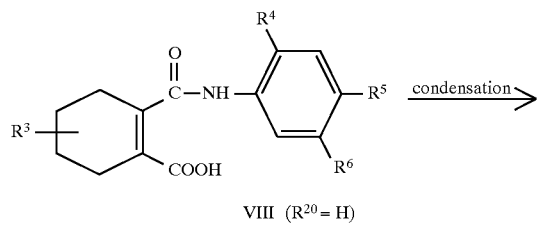

VIII ($R^{20}$ = H)

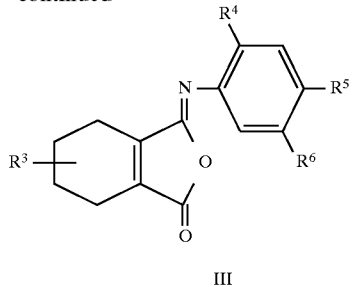

III

The condensation is carried out in an inert solvent in the presence of a condensing agent.

Examples of suitable solvents are aromatic hydrocarbons, such as toluene and xylene, aliphatic hydrocarbons, such as hexane, halohydrocarbons, such as dichloromethane or chlorobenzene, ketones, such as acetone and methyl ethyl ketone, ethers, such as diethyl ether, dioxane and tetrahydrofuran, esters, such as ethyl acetate, or nitriles, such as acetonitrile.

Suitable condensing agents are mainly carbodiimides derivatives, eg. dicyclohexylcarbodiimides or diethylcarbodiimide, or combinations of a base and an acylating agent or acyl chloride.

Examples of suitable bases for this purpose and aliphatic, aromatic or heterocyclic nitrogen compounds, such as triethylamine, dimethylaniline and pyridine, or inorganic bases, such as sodium carbonate, potassium carbonate and sodium bicarbonate.

Among the acyl chlorides, for example, thionyl chloride and phosphoryl chloride are suitable.

Examples of suitable acylating agents are acetic anhydride, methyl chloroformate, trifluoroacetic anhydride and acetyl chloride.

The amount of condensing agent is not critical. In order to achieve the maximum possible conversion, it is advisable to use from an equimolar amount to twice the amount, based on VIII, of condensing agent.

The reaction is carried out at from −20° to 100° C., preferably from 0° to 50° C.

The compounds VIII are obtained, for example, by reacting an aniline XI with a tetrahydrophthalic anhydride XII in an inert solvent (cf. U.S. Pat. No. 4,472,190 and the literature cited there) or a substituted 3,4,5,6-tetrahydrophthalimide II with a hydroxide or alcoholate $R^{20}$—$O^-M^+$, where $M^+$ is one equivalent of a metal ion, in particular of an alkali metal ion, such as lithium, sodium and potassium, and $R^{20}$ is hydrogen, $C_1$–$C_6$-alkyl, $C_3$–$C_6$-alkenyl or phenyl which may be unsubstituted or may carry from one to three radicals selected from the group consisting of halogen, cyano, nitro, $C_1$–$C_6$-alkyl, $C_1$–$C_4$-haloalkyl and $C_1$–$C_6$-alkoxy.

The reaction of an aniline derivative XI with a tetrahydrophthalic anhydride XII is carried out in an inert solvent or diluent, aromatic hydrocarbons, such as toluene and xylene, aliphatic hydrocarbons, such as hexane, halohydrocarbons, such as dichloromethane and chlorobenzene, ethers, such as diethyl ether, dioxane and tetrahydrofuran, alcohols, such as methanol and ethanol, or organic acids, such as acetic acid, being particularly suitable for this purpose.

The reaction of a substituted 3,4,5,6-tetrahydrophthalimide II with a hydroxide or alcoholate is likewise carried out in an inert solvent or diluent, for example aromatic hydrocarbons, such as toluene and xylene, aliphatic hydrocarbons, such as hexane, halohydrocarbons, such as dichloromethane or chlorobenzene, ethers, such as diethyl ether, dioxane and tetrahydrofuran, or alcohols, such as methanol and ethanol, being suitable for this purpose.

For both methods of preparation, the reactants are usually used in roughly equimolar amounts, unless an excess of up to about 10 mol % of one or other component is advisable.

The reaction temperature is usually from 0° to 100° C., preferably from 10° to 60° C.

The compounds X, XI and XII are known or can be prepared by methods known per se, as described, for example, in the abovementioned publications.

Among the tetrahydrophthalamic esters VIII, novel ones are those of the formula VIIIa

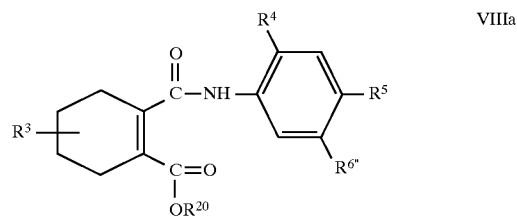

VIIIa provided that $R^5$ and $R^{6"}$ do not together form one of the following chains:

a substituted di- or trimethyleneoxy group bonded to the bonding site $R^{6"}$ via the oxygen, a substituted di- or trimethylenecarbonyl group bonded to the bonding site $R^{6"}$ via the carbonyl group or a substituted di- or trimethyleneoximino group bonded to the bonding site $R^{6"}$ via the oximino group.

$R^{6"}$ differs from $R^6$ only in the meaning $OR^{9"}$ instead of —$OR^9$, where $R^{9"}$ (in contrast to $R^9$) is not $C_1$–$C_6$-haloalkyl, $C_3$–$C_6$-haloalkenyl, $C_3$–$C_6$-haloalkynyl or $C_1$–$C_6$-alkoxycarbonyl-$C_2$–$C_6$-alkyl (cf. DE-A 27 33 115, EP-A 073 409, EP-A 271 170, EP-A 275 131, JO 59/070 682 and JO 59/204 181).

Both the substituted cyclohexene-1,2-dicarboxylic acid derivatives Ia and Ib and the tetrahydrophthalimides IIa and IIb, the tetrahydroisophthalimides III and the tetrahydrophthalamic esters VIII may be obtained as isomer mixtures in the preparation. However, all isomer mixtures can, if desired, be separated into the pure isomers by the conventional methods, for example by crystallization or chromatography, if necessary over an optically active absorbate.

Mixtures of the optically active isomers which contain an excess of one isomer can also be prepared, for example, using optically active starting materials.

The novel substituted cyclohexene-1,2-dicarboxylic acid derivatives Ia and Ib, tetrahydrophthalimides IIa and IIb, tetrahydroisophthalimides IIIa and tetrahydrophthalamic esters VIIIa are suitable, in the form of both isomer mixtures and the pure isomers, as herbicides and as defoliants/desiccants.

The substituted cyclohexene-1,2-dicarboxylic acid derivatives Ia and Ib, tetrahydrophthalimides IIa and IIb, tetrahydroisophthalimides IIIa and tetrahydrophthalamic esters IIIa are suitable, in the form of both isomer mixtures and the pure isomers, as herbicides, in particular for controlling dicotyledon weeds.

Particularly at low application rates, they are tolerated and therefore selective in crops such as wheat, rice, corn, soybean and cotton.

The substituted cyclohexene-1,2-dicarboxylic acid derivatives Ia and Ib, tetrahydrophthalimides IIa and IIb, tetrahydroisophthalimides IIIa and tetrahydrophthalamic esters VIIIa are also suitable as desiccants and defoliants, in particular for the defoliation of cotton, and as defoliants for drying out the above-ground plant parts in crops, for example potato, sunflower, soybean and rape. This permits completely mechanized harvesting of these important crops.

Also of economic interest is the facilitation of harvesting permitted by concentrated dropping at a particular time or reduction of the adhesion to the tree in the case of citrus fruits, olives or other species and varieties of pomes, drupes and hard-shelled fruit. They also lead to uniform ripening of the harvested fruits.

The same mechanism, ie. the promotion of the formation of abscission tissue between the fruit or leaf part and the shoot part of the plant is also essential for readily controllable defoliation of crops, in particular cotton. Furthermore, shortening the interval in which the individual cotton plants ripen leads to a higher fiber quality after harvesting.

The compounds Ia, Ib, IIa, IIb, IIIa and VIIIa and the herbicides or desiccants/defoliants containing them can be used, for example, in the form of directly sprayable aqueous solutions, powders, suspensions, including concentrated aqueous, oily or other suspensions or dispersions, emulsions, oil dispersions, pastes, dusts, broadcasting agents or granules, by spraying, nebulizing, dusting, broadcasting or pouring. The application forms depend on the intended uses; they should in any case ensure very fine distribution of the active ingredients.

The compounds Ia, Ib, IIa, IIb, IIIa and VIIIa are suitable in general for the prepration of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms may be prepared from emulsion concentrates, dispersions, pastes, wettable powders or water-dispersible granules by adding water. For the preparation of emulsions, pastes or oil dispersions, the substrates as such or dissolved in an oil or solvent can be homogenized in water by means of wetting agents, adherents, dispersants or emulsifiers. However, it is also possible to prepare concentrates which consist of active ingredient, wetting agents, adherents, dispersants and emulsifiers and possibly solvents or oil and which are suitable for dilution with water.

Suitable surfactants are alkali metal, alkaline earth metal and ammonium salts of aromatic sulfonic acids, for example lignin-, phenol-, naphthalene- and dibutylnaphthalene-sulfonic acid, and of fatty acids, alkylsulfonates and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ethers, ethoxylated isooctyl-, octyl- or nonyl-phenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylenealkyl ethers or polyoxypropylene, lauryl alcohol polyglycol ether acetal, sorbitol esters, ligninsulfite waste liquors or methylcellulose.

Powders, broadcasting agents and dusts can be prepared by mixing or milling the active ingredients together with a solid carrier.

Granules, for example coated, impregnated and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as cereal flour, bark meal, wood meal and nutshell meal, cellulosic powders and other solid carriers.

The formulations contain in general from 0.01 to 95, preferably from 0.5 to 90, % by weight of active ingredient. The active ingredients are used in a purity of from 90 to 100%, preferably from 95 to 100% (according to NMR spectrum).

Examples of such formulations are:

I. a mixture of 20 parts by weight of compound No. Ia.12, 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid, 5 parts by weight of the adduct of 40 mol of ethylene oxide with 1 mol of castor oil. By finely distributing the mixture in 100,000 parts by weight of water, an aqueous dispersion which contains 0.02% by weight of the active ingredient is obtained.

II. a dispersion of 20 parts by weight of compound No. Ia.09 in a mixture of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. The mixture of this dispersion with 100,000 parts by weight of water contains 0.02% by weight of the active ingredient.

III. a dispersion of 20 parts by weight of compound No. 010 in a mixture of 25 parts by weight of cyclohexanone, 65 parts by weight of a mineral oil fraction having a boiling point of from 210° to 280° C. and 10 parts by weight of the adduct of 40 mol of ethylene oxide with 1 mol of castor oil. The mixture of this dispersion with 100,000 parts by weight of water contains 0.02% of the active ingredient.

IV. a mixture, milled in a hammer mill, with 20 parts by weight of compound No. IIb.02, 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder. By finely distributing the mixture in 20,000 parts by weight of water, a spray liquor which contains 0.1% by weight of the active ingredient is obtained.

V. a mixture of 3 parts by weight of compound No. IIb.04 and 97 parts by weight of a finely divided kaolin. This dust contains 3% by weight of active ingredient.

VI. a stable oily dispersion of 20 parts by weight of compound No. IIIa.010, 2 parts by weight of the calcium salt of dodecylbenzenesulfonic acid, 8 parts by weight of a fatty alcohol polyglycol ether, 2 parts by weight of the sodium salt of a phenolsulfonic acid/urea/ formaldehyde condensate and 68 parts by weight of a paraffinic mineral oil.

The herbicides or the active ingredients can be applied by the preemergence or postemergence method. If the active ingredients are less well tolerated by certain crops, it is possible to use application methods in which the herbicides are sprayed with the aid of the sprayers in such a way that the leaves of the sensitive crops are as far as possible not affected, while the active ingredients reach the leaves of undesirable plants growing underneath or the uncovered soil surface (post-directed, lay-by).

The application rates of active ingredient are from 0.001 to 3.0, preferably from 0.01 to 1, kg/ha of active ingredient (a.i.), depending on the aim of control, the season, the target plants and the stage of growth.

In view of the versatility of the application methods, compounds Ia, Ib, IIa, IIb, IIIa and VIIIa and agents containing them may also be used in a further number of crops for eliminating undesirable plants. For example, the following crops are suitable:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica apa var. silvestris | beets |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroina cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To broaden the action spectrum and to achieve synergistic effects, compounds Ia, Ib, IIa, IIb, IIIa and VIIIa may be mixed with a large number of typical members of other groups of herbicidal or growth-regulating active ingredients and applied together with them. For example, suitable components of the mixture are diazines, 4H-3,1-benzoxazine derivatives, benzothiadiazinones, 2,6-dinitroaniline, N-phenylcarbamates, thiocarbamates, halocarboxylic acids, triazines, amides, ureas, diphenyl ethers, triazinones, uracils, benzofuran derivatives, cyclohexane-1,3-dione derivatives which may carry, for example, a carboxyl or carbimino group in the 2-position, quinolinecarboxylic acid derivatives, imidazolinones, sulfonamides, sulfonylureas, aryloxy- and hetaryloxyphenoxypropionic acids and the salts, esters and amides thereof and others.

It may also be useful to apply the compounds Ia, Ib, IIa, IIb, IIIa or VIIIa, alone or in combination with other herbicides, also mixed together with further crop protection agents, for example with pesticides or agents for controlling pests or phytopathogenic fungi or bacteria. The miscibility with mineral salt solutions which are used for eliminating nutrient and trace element deficiencies is also of interest. However, nonphytotoxic oils and oil concentrates may also be added.

PREPARATION EXAMPLES

Example 1

N-n-Propyl-N'-[4-chloro-3-(2-n-propylcarbamoylprop-1-en-1-yl)-phenyl]-3,4,5,6-tetrahydrophthalamide (compound Ia.01)

A solution of 10.9 g of N-[4-chloro-3-(2-chlorocarbonylprop-1-en-1-yl)-phenyl]-3,4,5,6-tetrahydrophthalimide in 200 ml of ethyl acetate was added dropwise to a solution of 5.9 g of n-propylamine in about 150 ml of ethyl acetate while cooling with ice. The mixture was stirred for 3 hours at about 20° C., after which the solid formed was separated off, washed twice with 5% by weight aqueous hydrochloric acid and then once with petroleum ether and then dried under reduced pressure at 40° C. The crude product was recrystallized from ethyl acetate. Mp.: 130°131° C.

Example 2

N,N-Dimethyl-N'-[4-chloro-3-(2-chloro-ethoxycarbonylethenyl)-phenyl]-3,4,5,6-tetrahydrophthalamide (compound Ia.09)

1.39 ml of a 40% strength by weight aqueous dimethylamine solution were added to a solution of 3.9 g of N-[4-chloro-3-(2-chloro-2-ethoxycarbonylethenyl)phenyl]-3,4,5,6-tetrahydrophthalimide in 100 ml of acetonitrile at about 20° C. The mixture obtained was stirred for a further 20 hours at 20°–25° C., after which the solid formed was separated off, washed with petroleum ether and finally dried. Mp.: 161°–164° C.

Example 3

N-[4–Chloro-3-(2-chloro-2-ethoxycarbonylethenyl)-phenyl]-3,4,5,6-tetrahydrophthalamide (compound (Ia.12)

Ammonia gas was passed into a solution of 5.9 g of N-[4-chloro-3-(2-chloro-2-ethoxycarbonylethenyl)-phenyl]-3,4,5,6-tetrahydrophthalimide in 150 ml of acetonitrile until saturation was reached. The reaction mixture obtained was then stirred for a further 19 hours at 20°–25° C., after which the solid formed was separated off and then washed with petroleum ether. Mp.: 185°–186° C.

Example 4

N-[4–Chloro-3-(2-chloro-2-ethoxycarbonylethenyl)-phenyl]-3,4,5,6-tetrahydroisophthalimide (compound IIIa.02)

1.85 g of dicyclohexylcarbodiimide were added to a suspension of 3.3 g of N-[4-chloro-3-(2-chloro-2-ethxoycarbonylethenyl)-phenyl]-3,4,5,6-terahydrophthalic acid monoamide in 40 ml of toluene at about 20° C. The reaction mixture obtained was then stirred for 3 hours at 20°–250° C. After the solid had been separated off, the clear solution obtained was evaporated down. The crude product was purified chromatographically over silica gel (mobile phase: 8:2 toluene/ethyl acetate). Yield: 0.9 g.

200 MHz-$^1$H-NMR (in CDCl$_3$; TMS as internal standard): d=1.4 ppm (t, 3H), 1.76–1.88 ppm (m, 4H), 2.35–2.62 ppm (m, 4H), 4.38 ppm (q, 2H), 7.14–7.56 ppm (m, 2H), 7.88 ppm (d, 1H), 8.12 ppm (s, 1H).

Example 5

N-[3-(2-Bromo-2-methoxycarbonylethenyl)-4-chlorophenyl]-2-cyanocyclohexenecarboxamide (compound Ib.02)

2.6 g of pyridine and then, at from 0° to 5° C., 4.6 g of trifluoroacetic anhydride in 10 ml of dichloromethane were added dropwise to a solution of 5 g of N-(3-(2-bromo-2-methoxycarbonylethenyl)-4-chlorophenyl]-cyclohexene-1,2-dicarboxamide in 80 ml of dichloromethane. Stirring was carried out for 1 hour at 5° C. and 2 hours at 25° C., after which 100 ml of water were added and stirring was carried out for a further 30 minutes. The organic phase was then separated off and dried. After removal of the solvent, the crude product was dissolved in 50 ml of diethyl ether. The product which had crystallized out was separated off from the cooled solution, the melting point of said product being 123°–125° C.

Example 6

N-[4–Chloro-3-(2-chloro-2-ethoxycarbonylethenyl)-phenyl]-3,4,5,6-tetrahydrophthalic acid monoamide (compound VIIIa.03)

10.8 g of N-[4-chloro-3-(2-chloro-2-ethoxycarbonylethenyl)-phenyl]-3,4,5,6-tetrahydrophthalimide were added to a solution of 1.2 g of sodium hydroxide in 200 ml of ethanol at about 20° C. The reaction mixture obtained was then stirred for 17 hours at 20°–25° C., after which the solvent was removed. The residue was dissolved in 100 ml of water. After acidification of the resulting aqueous phase with 10 mol % aqueous hydrochloric acid to a pH of 3, the solid formed was separated off. The crude product obtained was washed with water and petroleum ether and finally dried. Mp.: 131°–132° C.

Example 7

N-[4–Chloro-5-(2-chloro-2-ethoxycarbonyleth-1-yl)-2-fluorophenyl]-3,4,5,6-tetrahydrophthalimide (compound IIb.03)

3.5 g of N-(5-amino-4-chloro-2-fluorophenyl)-3,4,5,6-tetrahydrophthalimide in 5 ml of absolute acetonitrile were added dropwise to a suspension of 1.9 g of tert-butyl nitrite, 260 g of ethyl acrylate and 1.9 g of anhydrous copper(II) chloride in 200 ml of absolute acetonitrile at 0° C. The mixture was slowly warmed up to room temperature and was stirred at this temperature for 10 hours. 40 ml of dilute hydrochloric acid were then added, and the mixture was extracted three times with methyl tert-butyl ether. The combined organic phases were dried over sodium sulfate and evaporated down. The residue was chromatographed over silica gel (eluent: 2:1 petroleum ether/diethyl ether).

Yield: 1.3 g (26%); $^1$H-NMR (d$^6$-DMSO/TMS): δ=1.18 ppm (t, 3H); 1.74 (bs, 4H); 2.38 (bs, 4H); 3.30 (dd, 1H); 3.47 (dd, 1H); 4.17 (q, 2H); 4.82 (dd, 1H); 7.51 (d, 1H); 7.84 (d, 1H).

Example 8

N-[3-(2-Bromo-2-ethoxycarbonyleth-1-yl)-4-chlorophenyl]-3,4,5,6-tetrahydrophthalimide (compound IIb.08)

11.6 g of N-(3-amino-4-chlorophenyl)-3,4,5,6-tetrahydrophthalimide in 20 ml of absolute acetonitrile were added dropwise to a suspension of 6.2 g of tertbutyl nitrite, 400 ml of ethyl acrylate and 11.2 g of anhydrous copper(II) bromide in 200 ml of absolute acetonitrile at 0° C. The mixture was then slowly warmed up to room temperature and was stirred at this temperature for 10 hours. 300 ml of 20% strength hydrochloric acid were then added and the mixture was extracted three times with diethyl ether. The combined organic phases were dried over Na$_2$SO$_4$ and evaporated down. The residue was chromatographed over silica gel (eluent: 2:1 petroleum ether/diethyl ether). Yield: 5.0 g (27%); $^1$H-NMR (d$^6$-DMSO/TMS): δ=1.17 (t, 3H); 1.75 (bs, 4); 2.35 (bs, 4H); 3.38 (dd, 1H); 3.55 (dd, 1H); 4.18 (q, 2H); 4.75 (t, 1H); 7.30 (dd, 1H); 7.38 (d, 1H); 7.60 (d, 1H).

Example 9

N-[4-Chloro-3-(2-chloro-2-ethoxycarbonyleth-1-yl)-phenyl]-4-methyl-3,4,5,6-tetrahydrophthalimide (compound IIb.09)

1st stage (2-chloro-2-ethoxycarbonyleth-1-yl)-2-chloro-5-nitrobenzene)

7.2 g of 2-chloro-5-nitroaniline were added a little at a time to a suspension of 6.5 g of tert-butyl nitrite, 6.0 g of ethyl acrylate and 6.7 g of anhydrous copper(II) chloride in 150 ml of absolute acetonitrile at 20°–25° C. Stirring was carried out for 10 hours at 20°–25° C., after which 100 ml of 10% strength by weight hydrochloric acid were added dropwise. The reaction mixture obtained was finally extracted three time with methyl tert-butyl ether, dried over sodium sulfate and then evaporated down. The residue was purified by chromatography (over silica gel). Yield: 3.8 g (31%); $^1$H-NMR (in d$^6$-DMSO/TMS): δ [ppm]=1.28 (t, 3H), 3.36 (dd, 1H), 3.58 (dd; 1H), 4.24 (q, 2H), 4.56 (dd; 1H), 7.54 (d; 1H), 8.10 (dd; 1H), 8.18 (dd; 1H).

2nd stage (3-(2-chloro-ethoxycarbonyleth-1-yl)-4-chloroaniline)

2.92 g of (2-chloro-2-ethoxycarbonyleth-1-yl)-2-chloro-5-nitrobenzene were added a little at a time to a suspension of 1.8 g of iron powder in 17.5 ml of ethanol and 9 ml of glacia acetic acid at 65° C. The mixture was refluxed for 3 hours and then cooled to 20°–25° C., and ethyl acetate was added to the reaction mixture. The solid was then separated off. The precipitate was filtered off and the filtrate was evaporated down. The residue was again taken up in ethyl acetate and the solution was washed with water, dried over sodium sulfate and evaporated down. Yield: 2.0 g (76%); $^1$H-NMR (in d$^6$-DMSO/TMS): δ [ppm]=1.12 (t, 3H), 3.05 (dd, 1H), 3.22 (dd, 1H), 4.12 (dd, 1H), 4.62 (t, 2H), 5.25 (s, 2H), 6.48 (m, 2H), 7.01 (d, 1H).

3rd stage (N-(4-chloro-3-(2-chloro-2-ethoxycarbonyleth-1-yl)-phenyl]-4-methyl-3,4,5,6-tetrahydrophthalimide)

2.60 g of 3-(2-chloro-2-ethoxycarbonyleth-1-yl)-4-chloroaniline and 1.65 g of 4-methyl-3,4,5,6-tetrahydrophthalic anhydride were refluxed for 6 hours. After the mixture had been cooled and evaporated down, the residue was taken up in ethyl acetate and the solution was washed three times with water. The organic phase was dried over $Na_2SO_4$ and then evaporated down. Yield 3.0 g (75%); $^1$H-NMR (in d$^6$-DMSO/TMS): δ [ppm]=0.96 (d; 3H), 1.05 (t; 3H), 1.64–2.08 (m; 3H), 2.15–2.70 (m; 4H), 3.20–3.55 (m; 2H), 4.14 (q; 2H), 4.78 (dd; 1H), 7.26 (d; 1H), 7.34 (s; 1H), 7.55 (d; 1H).

Tables 23 and 24 below list particularly preferred substituted cyclohexene-1,2-dicarboxylic acid derivatives Ia and Ib, which were prepared according to Examples 1 to 3 and 4. The tetrahydrophthalimides IIa, tetrahydroisophthalimides IIIa and tetrahydrophthalamic esters VIIIa were obtained similarly to Examples 4 and 6.

Table 28 lists particularly preferred substituted tetrahydrophthalimides IIb, which were prepared similarly to Examples 7 and 8.

TABLE 23

Ia

| No. | R$^1$ | R$^2$ | R$^4$ | R$^5$ | R$^6$ | Mp. [°C.] |
|---|---|---|---|---|---|---|
| Ia.01 | n-C$_3$H$_7$ | H | H | Cl | CH=C(CH$_3$)—CO-n-C$_3$H$_7$ | 130–131 |
| Ia.02 | i-C$_4$H$_9$ | H | H | Cl | CH=Cl(CH$_3$)—CO-i-C$_4$H$_9$ | 152–153 |
| Ia.03 | n-C$_4$H$_9$ | H | H | Cl | CH=C(CH$_3$)—CO-n-C$_4$H$_9$ | 137–138 |
| Ia.04 | n-C$_5$H$_{11}$ | H | H | Cl | CH=Cl(CH$_3$)—CO-n-C$_5$—H$_{11}$ | 138–139 |
| Ia.05 | i-C$_3$H$_7$ | H | H | Cl | CH=CH—COOCH$_3$ | 208–211 |
| Ia.06 | CH$_2$C≡CH | H | H | Cl | CH=CCl—COOC$_2$H$_5$ | 175–177 |
| Ia.07 | n-C$_4$H$_9$ | H | H | Cl | CH=CCl—COOC$_2$H$_5$ | 150–153 |
| Ia.08 | Cyclopropyl | H | H | Cl | CH=CCl—COOC$_2$H$_5$ | 150–152 |
| Ia.09 | CH$_3$ | CH$_3$ | H | Cl | CH=CCl—COOC$_2$H$_5$ | 161–164 |
| Ia.10 | —(CH$_2$)$_4$— | | H | Cl | CH=CCl—COOC$_2$H$_5$ | 149–150 |
| Ia.11 | —(CH$_2$)$_2$—O—(CH$_2$)$_2$— | | H | Cl | CH=CCl—COOC$_2$H$_5$ | 158–160 |
| Ia.12 | H | H | H | Cl | CH=CCl—COOC$_2$H$_5$ | 185–186 |
| Ia.13 | CH$_2$C≡CH | H | H | Cl | CH=C(C$_2$H$_5$)—COOC$_2$H$_5$ | 153–154 |
| Ia.14 | —(CH$_2$)$_2$—O—(CH$_2$)$_2$— | | H | Cl | CH=C(C$_2$H$_5$)—COOC$_2$H$_5$ | 90–92 |
| Ia.15 | CH$_3$ | H | H | Cl | CH=CCl—COOC$_2$H$_5$ | 183–184 |
| Ia.16 | CH$_2$C≡CH | H | H | Cl | CH=CBr—COOCH$_3$ | 157–158 |
| Ia.17 | CH$_3$ | CH$_3$ | H | Cl | CH=CBr—COOCH$_3$ | 158–159 |
| Ia.18 | CH$_2$C≡CH | H | H | Cl | CH=CH—COOC$_2$H$_5$ | 172–173 |
| Ia.19 | CH$_3$ | CH$_3$ | H | Cl | CH=CH—COOC$_2$H$_5$ | 157–158 |
| Ia.20 | —(CH$_2$)—O—(CH$_2$)$_2$— | | H | Cl | CH=CH—COOC$_2$H$_5$ | 171–172 |
| Ia.21 | CH$_3$ | CH$_3$ | H | Cl | 1,3-dithiolan-2-yl | 184–186 |
| Ia.22 | —(CH$_2$)—O—(CH$_2$)$_2$— | | H | Cl | 1,3-dithiolan-3-yl | 194–196 |
| Ia.23 | (CH$_2$)$_2$—OCH$_3$ | H | H | Cl | 4-methyl-1,4-dithiolan-2-yl | 123–125 |
| Ia.24 | CH$_3$ | CH$_3$ | H | Cl | 4-methyl-1,4-dithiolan-2-yl | 157–158 |
| Ia.25 | —(CH$_2$)$_2$—O—(CH$_2$)$_2$— | | H | Cl | 4-methyl-1,4-dithiolan-2-yl | 180–181 |
| Ia.26 | —(CH$_2$)$_2$—O—CH(CH$_3$)—CH$_2$— | | H | Cl | 4-methyl-1,4-dithiolan-2-yl | 143–145 |
| Ia.27 | N-morpholino | | H | Cl | 4-methyl-1,4-dithiolan-2-yl | 180–181 |
| Ia.28 | i-C$_3$H$_7$ | H | H | Cl | O—CH$_2$-tetrahydro-2H-pyran-3-yl | 187–188 |
| Ia.29 | —(CH$_2$)$_2$—O—(CH$_2$)$_2$— | | H | Cl | O—CH$_2$-tetrahydro-2H-pyran-3-yl | 156–158 |
| Ia.30 | CH$_3$ | CH$_3$ | H | O—CH$_2$—CO—N(CH$_2$C≡CH)— | | 175–177 |
| Ia.31 | i-C$_3$H$_7$ | H | H | S—CH$_2$—CO—N(CH$_3$)— | | 195–196 |

TABLE 23-continued

Cyclohexene-1,2-dicarboxylic acid derivatives Ia structure Ia: cyclohexene ring with C(=O)–NH–aryl(R4,R5,R6) and C(=O)–NR1R2

| No. | $R^1$ | $R^2$ | $R^4$ | $R^5$ | $R^6$ | Mp. [°C.] |
|---|---|---|---|---|---|---|
| Ia.32 | i-$C_3H_7$ | H | H | Cl | O—$CH_2$-tetrahydrofuran-2-yl | 155–156 |
| Ia.33 | —$(CH_2)_2$—O—$(CH_2)_2$— | | H | Cl | O—$CH_2$-tetrahydrofuran-2-yl | 110–112 |
| Ia.34 | $CH_3$ | H | H | Cl | 4-methyl-1,3-dithiolan-2-yl | 152–153 |
| Ia.35 | —$CH_2$—C($CH_3$)$_2$—O—C($CH_3$)$_2$—$CH$— | | H | Cl | 4-methyl-1,3-dithiolan-2-yl | 169–171 |
| Ia.36 | H | H | H | Cl | CH=CBr—$COOCH_3$ | 217–219 |
| Ia.37 | —$(CH_2)_2$—O—$(CH_2)_2$— | | H | Cl | $OCH_2CN$ | 155 |
| Ia.38 | $CH_2C{\equiv}CH$ | H | H | Cl | $OCH_2CN$ | 151 |
| Ia.39 | H | H | H | Cl | CH=CH—$COOC_2H_5$ | 178–179 |
| Ia.40 | H | H | H | Cl | 4-methyl-1,4-dithiolan-2-yl | Öl |

TABLE 24

Cyclohexene-1,2-dicarboxylic acid derivatives Ib where $R^3$ = H structure Ib: cyclohexene with C(=O)NH-aryl and CN substituents

| No. | $R^4$ | $R^5$ | $R^6$ | Mp. [°C.] |
|---|---|---|---|---|
| Ib.001 | H | Cl | CH=CH—CN | |
| Ib.010 | H | Cl | CH=CCl—$COOC_2H_5$ (E:Z = 36:64) | 139–140 |
| Ib.011 | H | Cl | CH=CBr—$COOCH_3$ | 123–125 |
| Ib.024 | H | Cl | CH=C($CH_3$)-$COOCH_3$ | |
| Ib.025 | H | Cl | CH=N—$OC_2H_5$ | 93–95 |
| Ib.026 | H | Cl | CH=CCl—$COCH_3$ | |
| Ib.027 | H | Cl | CH=CH—$COCHCl_2$ | |
| Ib.028 | H | Cl | CH=CH—CON($CH_3$)$_2$ | |
| Ib.029 | H | Cl | CH($OCH_3$)$_2$ | |
| Ib.030 | H | Cl | CH($OC_2H_5$)$_2$ | |
| Ib.031 | H | Cl | 4-Methyl-1,3-dioxolan-2-yl | |
| Ib.032 | H | Cl | 1,3-Dithian-2-yl | |
| Ib.007 | H | Cl | CH=CH—$COOC_2H_5$ (E:Z = 58:42) | 123–125 |
| Ib.033 | H | Cl | CH=N—$OCH_3$ | |
| Ib.034 | H | Cl | CH=N—$OCH_2CH$=CHCl | |
| Ib.035 | H | Cl | CH=N—O—$CH_2CH_2$—[4-methyl-1,3-dioxolan-2-yl] | |
| Ib.036 | H | Cl | CH=N—OH | |
| Ib.037 | H | Cl | CH=N—OCH($CH_3$)$COOC_2H_5$ | |
| Ib.038 | H | Cl | CH=C(CN)$COOC_2H_5$ | |
| Ib.039 | H | Cl | $OCH_2CN$ | |
| Ib.040 | H | Cl | $OCH_2$—$C_6H_5$ | |
| Ib.041 | H | Cl | $OCH_2$-2,3-dihydro-6H-thiopyran-5-yl | |
| Ib.042 | H | Cl | $OCH_2$-tetrahydro-2H-pyran-3-yl | |
| Ib.043 | H | Cl | OCH($CH_3$)-$COOCH_3$ | |
| Ib.044 | H | Cl | $OCH_2$—$COOC_2H_5$ | |
| Ib.045 | H | Cl | CHO | |

TABLE 25

Tetrahydrophthalimides IIa where $R^3$ = $R^4$ = H structure IIa

| No. | $R^{6''}$ | Mp. [°C.] |
|---|---|---|
| IIa.01 | Thiazolidin-2-yl | 132–133 |
| IIa.02 | 4-Methoxycarbonyl-thiazolidin-2-yl | Oil |
| IIa.03 | 4-Ethoxycarbonyl-thiazolidin-2-yl | Oil |
| IIa.04 | 3-Acetyl-4-ethoxycarbonyl-thiazolidin-2-yl | 77–78 |
| IIa.05 | Oxazol-5-yl | 80–85 |
| IIa.06 | 2-Methyl-thiazol-4-yl | 165–167 |
| IIa.07 | 3,5-Dinitro-1,4-dihydro-pyridin-4-yl | 265–266 |
| IIa.08 | 4-Methyl-thiazol-2-yl | 91–93 |

TABLE 26

Tetrahydroisophthalimides IIIa where $R^3$ = H structure IIIa

| No. | $R^4$ | $R^5$ | $R^{6'}$ | Mp. [°C.] |
|---|---|---|---|---|
| IIIa.024 | H | Cl | CH=C($CH_3$)—$COOCH_3$ | 72–74 |
| IIIa.010 | H | Cl | CH=CCl—$COOC_2H_5$ | Oil |

TABLE 27

Tetrahydrophthalamic esters VIIIa where $R^3$ = H

VIIIa

| No. | $R^4$ | $R^5$ | $R^6$ | Mp. [°C.] |
|---|---|---|---|---|
| VIIIa.010 | H | Cl | CH=CCl—COOC$_2$H$_5$ | 131–132 |
| VIIIa.026 | H | Cl | 1,3-dithiolan-2-yl | 155–156 |
| VIIIa.016 | H | Cl | CH=C(CH$_3$)—COOH | 172–173 |
| VIIIa.035 | H | Cl | CH=CCl—COOH | 150–153 |

TABLE 28

Substituted 3,4,5,6-tetrahydrophthalimides IIb

| No. | $R^{3*}$ | $R^{4*}$ | $R^{5*}$ | $R^{22}$ | $R^{23}$ | Mp. [°C.] $^1$H-NMR δ [ppm] |
|---|---|---|---|---|---|---|
| IIb.01 | H | F | Cl | Cl | CH$_3$ | 1.74 (bs, 4H), 2.37 (bs, 4H), 3.32 (dd, 1H), 3.48 (dd, 1H), 3.75 (s, 3H), 4.83 (dd, 1H), 7.51 (d, 1H), 7.72 (d, 1H) |
| IIb.02 | H | H | Cl | Cl | CH$_3$ | 80–81 |
| IIb.03 | H | F | Cl | Cl | C$_2$H$_5$ | 1.18 (t, 3H), 1.74 (bs, 4H), 2.38 (bs, 4H), 3.30 (dd, 1H), 3.47 (dd, 1H), 4.17 (q, 2H), 4.82 (dd, 1H), 7.51 (d, 1H), 7.84 (d, 1H) |
| IIb.04 | H | H | Cl | Cl | C$_2$H$_5$ | 1.18 (t, 3H), 1.74 (bs, 4H), 23.5 (bs, 4H), 3.30 (dd, 1H), 3.50 (dd, 1H), 4.20 (q, 2H), 4.82 (dd, 1H), 7.28 (dd, 1H), 7.36 (d, 1H), 7.58 (d, 1H) |
| IIb.05 | H | F | Cl | Br | CH$_3$ | 1.73 (bs, 4H), 2.35 (bs, 4H), 3.27 (m, 1H), 3.49 (m, 1H) 3.70 (s, 3H), 4.75 (t, 1H), 7.50 (d, 1H), 7.75 (d, 1H) |
| IIb.06 | H | F | Cl | Br | C$_2$H$_5$ | 1.18 (t, 3H), 1.75 (bs, 4H), 2.34 (bs, 4H), 3.38 (m, 1H), 3.53 (m, 1H), 4.16 (q, 2H), 4.75 (t, 1H), 7.50 (d, 1H), 7.75 (d, 1H) |
| IIb.07 | H | H | Cl | Br | CH$_3$ | 80–82 |
| IIb.08 | H | H | Cl | Br | C$_2$H$_5$ | 1.17 (t, 3H), 1.75 (bs, 4H), 2.35 (bs, 4H), 3.38 (dd, 1H), 3.55 (dd, 1H), 4.18 (q, 2H), 4.75 (t, 1H), 7.30 (dd, 1H), 7.38 (d; 1H), 7.60 (d, 1H) |
| IIb.09 | CH$_3$ | H | Cl | Cl | C$_2$H$_5$ | 0.96 (d, 3H), 1.05 (t, 3H), 1.64–2.08 (m, 3H), 2.15–2.70 (m, 4H), 3.20–3.55 (m, 2H), 4.14 (q, 2H), 4.78 (dd, 1H), 7.26 (d, 1H), 7.34 (s, 1H), 7.55 (d, 1H) |

Use Examples (herbicidal activity)

The herbicidal action of the substituted cyclohexene-1,2-dicarboxylic acid derivatives I, tetrahydrophthalimides IIa and IIb, tetrahydroiosphthalimides IIIa and tetrahydrophthalamic esters VIIIa were demonstrated by means of greenhouse experiments:

The culture vessels used were plastic flower pots containing loamy sand with about 3.0% by weight of humus as a substrate. The seeds of the test plants were sown separately according to species.

In the preemergence treatment, the active ingredients suspended or emulsified in water were applied directly after sowing, by means of finely distributing nozzles. The vessels were lightly sprinkler-irrigated in order to promote germination and growth and were then covered with transparent plastic covers until the plants had begun to grow. This covering ensured more uniform germination of the test plants unless germination was adversely affected by the active ingredients.

For the postemergence treatment, the test plants were grown to a height of growth of from 3 to 15 cm, depending on the form of growth, before being treated with the active ingredients suspended or emulsified in water. The test plants were either sown and grown in the test vessels in which they were treated, or they were grown separately as seedlings and transplanted into the test vessels a few days before the treatment with the active ingredient formulations.

The application rate for the postemergence treatment was 0.5 kg/ha of a.i. (active ingredient).

The plants were kept at from 10° to 25° C. or from 20° to 35° C., depending on the species. The test period covered from 2 to 4 weeks. During this time, the plants were tended and their reaction to the individual treatments was evaluated.

The evaluation was based on a scale from 0 to 100. 100 means no emergence of the plants or complete destruction of at least the above-ground parts, and 0 means no damage or normal course of growth.

The plants used in the greenhouse experiments consisted of the following species:

| Botanical name | Common name |
|---|---|
| Amaranthus retroflexus | redroot pigweed |
| Centaurea cyanus | cornflower |
| Galium aparine | catchweed bedstraw |
| Ipomoea subspecies | morningglory |

The result showed that undesirable weeds can be very readily controlled with compounds No. Ia.12, Ia.09, Ia.06, Ia.08, Ia.07, Ia.10, Ia.11, Ib.010, IIb.02 to IIb.04 and IIIa.010.

We claim:

1. A substituted cyclohexene-1,2-dicarboxylic acid derivative of the formula Ia

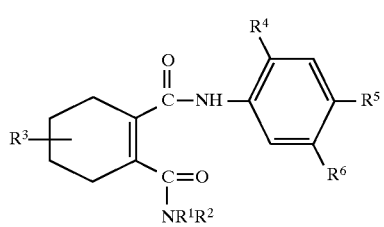

where
$R^1$ and $R^2$ are each
(i) hydrogen,
(ii) a $C_1$–$C_6$-alkyl, $C_3$–$C_6$-alkenyl or $C_3$–$C_6$-alkynyl group, each of which optionally carry from one to three radicals selected from the group consisting of halogen, cyano, amino, thio, hydroxyl, $C_1$–$C_6$-alkoxy, $C_1$–$C_6$-alkylsulfinyl, $C_1$–$C_6$-alkylsulfonyl, $C_1$–$C_6$-alkylcarbonyl, carboxyl, $C_1$–$C_6$-alkoxycarbonyl, $C_1$–$C_6$-alkylamino, $C_1$–$C_6$-dialkylamino, $C_1$–$C_6$-alkylaminocarbonyl, $C_1$–$C_6$-dialkylaminocarbonyl, $C_1$–$C_6$-alkylphosphono, $C_1$–$C_6$-dialkylphosphono, phenyl, where the phenyl radical optionally carries one of the following substituents on each substitutable carbon atom: hydroxyl, halogen, cyano, nitro, trifluoromethyl, $C_1$–$C_6$-alkyl or $C_1$–$C_6$-alkoxy;
(iii) a $C_3$–$C_8$-cycloalkyl group,
(iv) a phenyl group, which is unsubstituted or optionally carries one of the following radicals on each substitutable carbon atom: hydroxyl, halogen, cyano, nitro, trifluoromethyl, halogen or $C_1$–$C_6$-alkyl;

and, if $R^1$ is hydrogen or a $C_1$–$C_6$-alkyl group, $R^2$ may additionally be:

hydroxyl;
a $C_1$–$C_6$-alkoxy, $C_3$–$C_6$-alkenyloxy or $C_3$–$C_6$-alkynyloxy group;
a $C_3$–$C_7$-cycloalkoxy or $C_5$–$C_7$-cycloalkenyloxy group;
a $C_1$–$C_6$-haloalkoxy or $C_3$–$C_6$-haloalkenyloxy group;
a $C_3$–$C_7$-cycloalkyl-$C_1$–$C_6$-alkoxy group;
a $C_1$–$C_6$-alkylcarbonyloxy group;
a $C_1$–$C_6$-cyanoalkoxy group;
a hydroxy-$C_1$–$C_6$-alkoxy, $C_1$–$C_6$-alkoxy-$C_1$–$C_6$-alkoxy or $C_1$–$C_6$-alkoxycarbonyl-$C_1$–$C_6$-alkoxy group;
a $C_1$–$C_6$-alkylthio-$C_1$–$C_6$-alkoxy group;
a $C_1$–$C_6$-alkylamino-$C_1$–$C_6$-alkoxy or $C_1$–$C_6$-dialkylamino-$C_1$–$C_6$-alkoxy group;
a phenyl-$C_1$–$C_6$-alkoxy, phenyl-$C_3$–$C_6$-alkenyloxy or phenyl-$C_3$–$C_6$-alkynyloxy group; where in each case one or two methylene groups of the alkoxy, alkenyloxy or alkynyloxy chains optionally are replaced by oxygen, sulfur or a $C_1$–$C_6$-alkylamino chain; and each phenyl ring is unsubstituted or optionally carries from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl;
a group —$NR^7R^8$, where $R^7$ and $R^8$, independently of one another, are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl or phenyl which is unsubstituted or optionally carries from one to three radicals selected from the group consisting of $C_1$–$C_6$-alkyl, halogen, cyano, nitro, $C_1$–$C_6$-alkoxy and $C_1$–$C_6$-alkoxycarbonyl;

$R^3$ is hydrogen or a $C_1$–$C_6$-alkyl group;

$R^4$ is hydrogen or halogen;

$R^5$ is hydrogen, halogen, nitro, cyano or trifluoromethyl;

$R^6$ is —A—CO—B or —$CHR^{10}$—$CHR^{11}$—CO—B, where:
A is a straight-chain $C_2$–$C_4$-alkenylene or $C_2$–$C_4$-alkynylene chain, both of which are unsubstituted or optionally carry one or two radicals selected from the group consisting of halogen, cyano, $C_1$–$C_6$-alkyl, $C_1$–$C_6$-haloalkyl, hydroxyl, $C_1$–$C_6$-alkoxy, $C_1$–$C_6$-alkylcarbonyloxy, $C_1$–$C_6$-alkoxycarbonyl and $C_1$–$C_6$-alkylcarbonyl; and
B is hydrogen, $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, —$OR^{17}$ or —$SR^{17}$, where $R^{17}$ is:
hydrogen, $C_1$–$C_6$-alkyl, $C_3$–$C_6$-alkenyl, $C_3$–$C_6$-alkynyl, $C_3$–$C_6$-cycloalkyl or $C_1$–$C_6$-haloalkyl;
phenyl, which is unsubstituted or optionally carries from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl,
$C_1$–$C_6$-cyanoalkyl, $C_3$–$C_6$-haloalkenyl, $C_1$–$C_6$-alkoxycarbonyl,
$C_1$–$C_6$-alkoxy-$C_1$–$C_6$-alkyl, $C_1$–$C_6$-alkoxycarbonyl-$C_1$–$C_6$-alkyl or $C_1$–$C_6$-alkoximino-$C_1$–$C_6$-alkyl;
or B is phenyl, which is unsubstituted or optionally carries from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl;
or B is $C_1$–$C_6$-alkoxy-$C_1$–$C_6$-alkyl, di-($C_1$–$C_6$-alkoxy)-$C_1$–$C_6$-alkyl or $C_1$–$C_6$-alkylthio-$C_1$–$C_6$-alkyl;
or B is —$NR^{18}R^{19}$, where $R^{18}$ and $R^{19}$, independently of one another, are each hydrogen, $C_1$–$C_6$-alkyl, $C_3$–$C_6$- alkenyl, $C_3$–$C_6$-alkynyl, $C_3$–$C_6$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl or phenyl which is unsubstituted or optionally carries from one to three radicals selected from the group consisting of $C_1$–$C_6$-alkyl, $C_3$–$C_6$-alkenyl, halogen, cyano, nitro, $C_1$–$C_6$-alkoxy and $C_1$–$C_6$-alkoxycarbonyl;

$R^{10}$ is:
 hydrogen or cyano;
 $C_1$–$C_6$-alkyl, $C_3$–$C_6$-alkenyl, $C_3$–$C_6$-alkynyl;
 $C_1$–$C_6$-haloalkyl;
 $C_3$–$C_7$-cycloalkyl;
 $C_1$–$C_6$-alkoxycarbonyl or $C_1$–$C_6$-alkoxycarbonyl-$C_1$–$C_6$-alkyl;
 phenyl which is unsubstituted or optionally carries from one to three radicals selected from the group consisting of halogen, nitro, cyano, $C_1$–$C_6$-alkyl, $C_3$–$C_6$-alkenyl, $C_1$–$C_6$-haloalkyl, $C_1$–$C_6$-alkoxy and $C_1$–$C_6$-alkoxycarbonyl;

$R^{11}$ is:
 halogen, trifluoromethyl, hydroxyl, $C_1$–$C_6$-alkoxy or $C_1$–$C_6$-alkylcarbonyloxy;

or an agriculturally useful salt of the compound of formula Ia.

2. A substituted cyclohexene-1,2-dicarboxylic acid derivative of the formula Ib

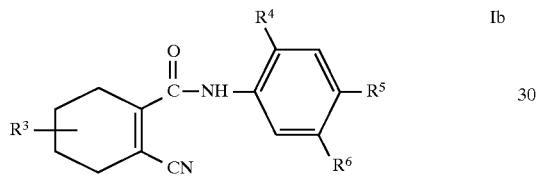

where:
$R^3$ is hydrogen or $C_1$–$C_6$-alkyl;
$R^4$ is hydrogen or halogen;
$R^5$ is hydrogen, halogen, nitro, cyano or trifluoromethyl;
$R^6$ is —A—CO—B or —CHR$^{10}$—CHR$^{11}$—CO—B, where:
 A is a straight-chain $C_2$–$C_4$-alkenylene or $C_2$–$C_4$-alkynylene chain, both of which are unsubstituted or optionally carry one or two radicals selected from the group consisting of halogen, cyano, $C_1$–$C_6$-alkyl, $C_1$–$C_6$-haloalkyl, hydroxyl, $C_1$–$C_6$-alkoxy, $C_1$–$C_6$-alkylcarbonyloxy, $C_1$–$C_6$-alkoxycarbonyl and $C_1$–$C_6$-alkylcarbonyl; and
 B is hydrogen, $C_1$–$C_6$-alkyl, $C_3$–$C_6$-alkenyl, $C_3$–$C_6$-alkynyl, $C_1$–$C_6$-haloalkyl, $C_3$–$C_7$-cycloalkyl, —OR$^{17}$ or —SR$^{17}$, where R$^{17}$ is:
  hydrogen, $C_1$–$C_6$-alkyl, $C_3$–$C_6$-alkenyl, $C_3$–$C_6$-alkynyl, $C_3$–$C_6$-cycloalkyl or $C_1$–$C_6$-haloalkyl;
  phenyl, which is unsubstituted or optionally carries from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl,
  $C_1$–$C_6$-cyanoalkyl, $C_3$–$C_6$-haloalkenyl, $C_1$–$C_6$-alkoxycarbonyl, $C_1$–$C_6$-alkoxy-$C_1$–$C_6$-alkyl, $C_1$–$C_6$-alkoxycarbonyl-$C_1$–$C_6$-alkyl or $C_1$–$C_6$-alkoximino-$C_1$–$C_6$-alkyl; or or B is phenyl, which is unsubstituted or optionally carries from one to three radicals selected from the group consisting of $C_1$–$C_6$-alkyl, $C_2$–$C_6$-alkenyl, halogen, cyano, nitro, $C_1$–$C_6$-haloalkyl, $C_1$–$C_6$-alkoxy and $C_1$–$C_6$-alkoxycarbonyl;
 or B is $C_1$–$C_6$-alkoxy-$C_1$–$C_6$-alkyl, di-($C_1$–$C_6$-alkoxy)-$C_1$–$C_6$-alkyl or $C_1$–$C_6$-alkylthio-$C_1$–$C_6$-alkyl;
 or B is —NR$^{18}$R$^{19}$, where R$^{18}$ and R$^{19}$, independently of one another, are each hydrogen, $C_1$–$C_6$-alkyl, $C_3$–$C_6$-alkenyl, $C_3$–$C_6$-alkynyl, $C_3$–$C_6$-cycloalkyl, $C_1$–$C_6$-haloalkyl, $C_1$–$C_6$-alkylcarbonyl, $C_1$–$C_6$-alkoxycarbonyl, $C_1$–$C_6$-alkoxy-$C_1$–$C_6$-alkyl or phenyl which is unsubstituted or optionally carries from one to three radicals selected from the group consisting of $C_1$–$C_6$-alkyl, $C_3$–$C_6$-alkenyl, halogen, cyano, nitro, $C_3$–$C_6$-alkoxy and $C_1$–$C_6$-alkoxycarbonyl;

$R^{10}$ is:
 hydrogen or cyano;
 $C_1$–$C_6$-alkyl, $C_3$–$C_6$-alkenyl, $C_3$–$C_6$-alkynyl;
 $C_1$–$C_6$-haloalkyl;
 $C_3$–$C_7$-cycloalkyl;
 $C_1$–$C_6$-alkoxycarbonyl or $C_1$–$C_6$-alkoxycarbonyl-$C_1$–$C_6$-alkyl; or
 phenyl which is unsubstituted or optionally carries from one to three radicals selected from the group consisting of halogen, nitro, cyano, $C_1$–$C_6$-alkyl, $C_3$–$C_6$-alkenyl, $C_1$–$C_6$-haloalkyl, $C_1$–$C_6$-alkoxy and $C_1$–$C_6$-alkoxycarbonyl;

$R^{11}$ is:
 halogen, trifluoromethyl, hydroxyl, $C_1$–$C_6$-alkoxy or $C_1$–$C_6$-alkylcarbonyloxy;

or an agriculturally useful salt of the compound of formula Ib.

3. A herbicide comprising an inert liquid or solid carrier and a herbicidal amount of at least one substituted cyclohexene-1,2-dicarboxylic acid derivative of the formula Ia, or an agriculturally useful salt of Ia, as claimed in claim 1.

4. A method for controlling undesirable plant growth, wherein a herbicidal amount of at least one substituted cyclohexene-1,2-dicarboxylic derivative of the formula Ia or an agriculturally useful salt of Ia as defined in claim 1 is allowed to act on undesirable plants or on their habitat or on seed.

5. A herbicide comprising an inert liquid or solid carrier and a herbicidal amount of at least one substituted cyclohexene-1,2-dicarboxylic acid derivative of the formula Ib, or an agriculturally useful salt of Ib, as defined in claim 2.

6. A method for controlling undesirable plant growth, wherein a herbicidal amount of at least one substituted cyclohexene-1,2-dicarboxylic derivative of the formula Ib, or an agriculturally useful salt of Ib, as defined in claim 2 is allowed to act on undesirable plants or on their habitat or on seed.

* * * * *

UNITED STATES PATENT AND TRADEMARK OFFICE
CERTIFICATE OF CORRECTION

PATENT NO.: 5,817,603

DATED: October 6, 1998

INVENTOR(S): KLINTZ et al.

It is certified that error appears in the above-identified patent and that said Letters Patent is hereby corrected as shown below:

Col. 72, claim 2, line 17, "$C_3$-$C_6$-alkoxy" should be --$C_1$-$C_6$-alkoxy--.

Col. 72, claim 3, line 40, "claimed" should be --defined--.

Signed and Sealed this

Nineteenth Day of January, 1999

*Attest:*

*Attesting Officer*

*Acting Commissioner of Patents and Trademarks*